(12) United States Patent
Ma et al.

(10) Patent No.: US 11,040,938 B2
(45) Date of Patent: Jun. 22, 2021

(54) CONTINUOUS FLOW PROCESS FOR THE SYNTHESIS OF PHENYLHYDRAZINE SALTS AND SUBSTITUTED PHENYLHYDRAZINE SALTS

(71) Applicant: SHANGHAI HYBRID—CHEM TECHNOLOGIES, Shanghai (CN)

(72) Inventors: Bing Ma, Shanghai (CN); Shuai Pan, Shanghai (CN)

(73) Assignee: Shanghai Hybrid-Chem Technologies, Shanghai (CN)

( * ) Notice: Subject to any disclaimer, the term of this patent is extended or adjusted under 35 U.S.C. 154(b) by 0 days.

(21) Appl. No.: 16/258,640

(22) Filed: Jan. 27, 2019

(65) Prior Publication Data

US 2019/0152896 A1    May 23, 2019

Related U.S. Application Data

(63) Continuation of application No. PCT/CN2017/094436, filed on Jul. 26, 2017.

(30) Foreign Application Priority Data

Jul. 27, 2016 (CN) .......................... 201610602290.6
Jul. 24, 2017 (CN) .......................... 201710608662.0

(51) Int. Cl.
*C07C 243/22* (2006.01)
*B01J 19/00* (2006.01)
(Continued)

(52) U.S. Cl.
CPC ......... *C07C 243/22* (2013.01); *B01J 19/0013* (2013.01); *B01J 19/0093* (2013.01);
(Continued)

(58) Field of Classification Search
None
See application file for complete search history.

(56) References Cited

FOREIGN PATENT DOCUMENTS

| CN | 104744295 | * | 3/2015 | ........... C07C 243/22 |
| CN | 102807505 | * | 4/2015 | ........... C07C 243/22 |

OTHER PUBLICATIONS

CN-104744295, 2020, Machine Translation from Google Patents.*
CN-102807505, 202, Machine Translation from Google Patents.*

* cited by examiner

*Primary Examiner* — Clinton A Brooks
(74) *Attorney, Agent, or Firm* — Zhihua Han; WEN IP LLC

(57) ABSTRACT

The present invention provided a continuous flow process for the synthesis of phenylhydrazine salts and substituted phenylhydrazine salts. Diazotization, reduction, acidic hydrolysis and salifying with acids are innovatively integrated together. Using acidic liquids of aniline or substituted aniline, diazotization reagents, reductants and acids as raw materials, phenylhydrazine derivative salts is obtained through the synthesis process, which is a three-step continuous tandem reaction including diazotization, reduction, acidic hydrolysis and salifying. The described synthesis process is a kind of integrated solutions, which is carried out in an integrated reactor. The feed inlets of the integrated reactor are continuously filled with raw materials. In the integrated reactor, diazotization, reduction, acidic hydrolysis and salifying are carried out continuously and orderly, and phenylhydrazine salts or substituted phenylhydrazine salts is obtained in the outlet of the integrated reactor without interruption. The total reaction time is no more than 20 min.

20 Claims, 1 Drawing Sheet

(51) Int. Cl.
  *B01J 19/24* (2006.01)
  *C07C 303/22* (2006.01)
  *C07C 241/02* (2006.01)
  *C07C 253/30* (2006.01)

(52) U.S. Cl.
  CPC ........... *B01J 19/242* (2013.01); *B01J 19/243* (2013.01); *B01J 19/245* (2013.01); *C07C 241/02* (2013.01); *C07C 253/30* (2013.01); *C07C 303/22* (2013.01); *B01J 2219/00033* (2013.01); *B01J 2219/00051* (2013.01); *B01J 2219/00159* (2013.01); *B01J 2219/00164* (2013.01); *B01J 2219/00792* (2013.01); *B01J 2219/00795* (2013.01); *B01J 2219/00867* (2013.01); *B01J 2219/00871* (2013.01); *B01J 2219/00873* (2013.01)

CONTINUOUS FLOW PROCESS FOR THE SYNTHESIS OF PHENYLHYDRAZINE SALTS AND SUBSTITUTED PHENYLHYDRAZINE SALTS

CROSS REFERENCES TO RELATED APPLICATION

This application is a national stage application of International application number PCT/CN20171094436, filed Jul. 26, 2017, titled "Continuous Flow Synthesis Process for Phenylhydrazine Salt and Substituted Phenylhydrazine salt," which claims the priority benefit of Chinese Patent Application Nos. 201610602290.6 and 201710608662,0, filed on Jul. 27, 2016 and Jul. 24, 2017, respectively, which is hereby incorporated by reference in its entirety.

FIELD OF THE INVENTION

The invention relates to the field of chemistry, in particular to a continuous flow synthesis process of phenylhydrazine salts and substituted phenylhydrazine salts.

BACKGROUND OF THE INVENTION

Phenylhydrazine was firstly synthesized by Hermann Emile Fischer in 1875 and is the first synthetic hydrazine derivative. With the deepening of the heterocyclic compounds research and expanding of application, substituted phenylhydrazine compounds have a wide range of applications, such as synthesizing antibacterial drugs, diabetes drugs, cancer drugs, antiviral drugs, antihypertensive drugs, etc. in health care, and synthesizing insecticide, bactericide and herbicide, etc. in crop protection. Also, substituted phenylhydrazine compounds are applied widely in the fuel industry, charge transfer materials, polymer materials and other industries.

The production processes of substituted phenylhydrazine series compounds are similar, mainly including diazotization reaction of aromatic amine, reduction by $Na_2SO_3$ or $SnCl_2$, and then all kinds of substituted phenylhydrazine compounds are obtained. A set of production equipment can produce a series of substituted phenylhydrazine products. Equipment investment is not large, and the products have high added value. The full utilization of equipment and maximum production capability release can be realized under the production intensification. Meanwhile, phenylhydrazine salts and substituted phenylhydrazine salts (such as p-chlorophenylhydrazine hydrochloride, etc.) are important intermediates for medicine and pesticide. But up to now, there has been no integrated synthesis process for these products of high purity in industrial production. With the booming development of pharmaceutical, pesticide and dye industries, there will be increasing demand for various substituted phenylhydrazine compounds. Therefore, the development of continuous synthesis process of substituted phenylhydrazine series compounds has realistic significance and broad prospect.

At present, the synthetic route of phenylhydrazine salts and substituted phenylhydrazine salts mainly takes phenylamine derivatives, diazotization reagents, reductants ($SnCl_2$ or $Na_2SO_3$, etc.) and acids as raw materials, and then goes through three steps of diazotization, reduction and acidic hydrolysis and salifying to get phenylhydrazine derivative salts. The specific reaction steps are as follows:

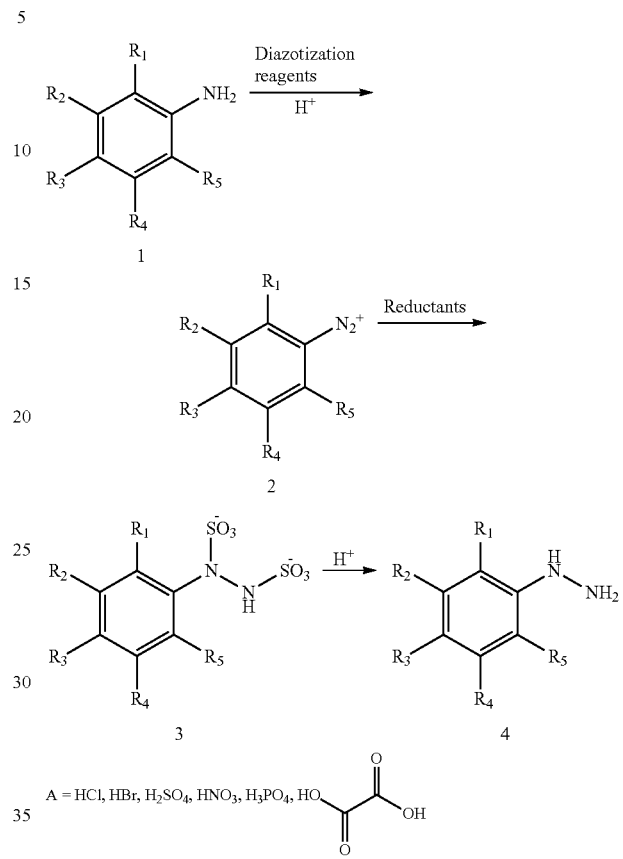

Where, $R_1, R_2, R_3, R_4, R_5$ are independently selected from —H, —F, —Cl, —Br, —CN, —$NO_2$, —$CF_3$, —$SO_3H$, —COOH, $C_1$-$C_4$ alkoxy groups, $C_1$-$C_4$ saturated or unsaturated alkyl; A is selected from HCl, HBr, $H_2SO_4$, $HNO_3$, $H_3PO_4$, HOOC—COOH (oxalic acid).

By-products (e.g., diazo amino compounds, reduction intermediates, reduction products, i.e., compound 3) are often produced in products after acidic hydrolysis and salifying and additional purification steps (e.g., extraction with organic solvents (e.g., toluene), washing (e.g., pickling or washing), recrystallization, etc.) are required to remove these by-products and improve the purity of the final product (phenylhydrazine salts and substituted phenylhydrazine salts). The by-products are referred to compounds 5, 6 and 7 as described below:

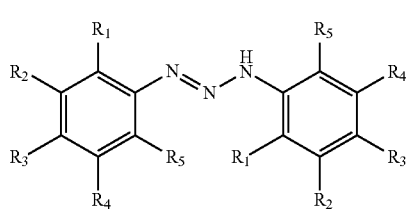

Diazo Amino Compounds

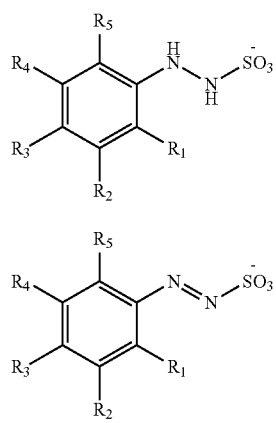

Reduction Intermediates

Currently, phenylhydrazine salts and substituted phenylhydrazine salts are mainly synthesized through batch processes. The first diazotization reaction is completed in the reaction kettle, and there will be a large amount of diazonium salt in the kettle during and after the diazotization reaction. Diazonium salt has poor thermal stability and is easy to decompose and explode, which results in great potential safety hazards in the production process, and also limits production capacity of phenylhydrazine salts and substituted phenylhydrazine salts, thus it's difficult to expand production further. In order to ensure the safety of production, most of the diazotization reactions in batch process are controlled at low temperatures (for example. 0~10° C.), which has increased the production energy consumption. The operation of raising and lowering temperature for many times not only makes the operation tedious, but also reduces the production efficiency. In addition, the synthetic route using $SnCl_2$ as reductant has some problems such as low yield, expensive reagent and serious pollution, and is mainly used for laboratory preparation, making little sense to industrial production. The synthesis route using $Na_2SO_3$ and other salts as reductant needs to adjust the pH value to 6~7 with sodium hydroxide. If the control is not good, bituminous by-products will be produced, which is difficult to operate.

The so-called batch process refers to the process of adding raw materials into the reactor and waiting for a certain time (including reaction time of each step, cooling time, heating time, temperature holding time, and interval waiting time of each operation, etc.). After the reaction reaches a certain requirement, the product is discharged at a time, that is, the production mode of the product is batch by batch, and each batch can only produce the limited and fixed amount of products (the amount depends on the volume of reactor). The total reaction time of batch process refers to the total time from raw materials to products, including the feeding time, reaction time, unloading time, material transfer time, cooling time, heating time, temperature holding time and the interval waiting time of each operation. In the process of batch process operation, the composition of materials (including intermediates and final products), temperature and other state parameters in the reactor will change with time, which is an unsteady process. The production process and product quality have great uncertainly, which directly leads to the unstable quality of downstream products and difficulty of control.

There are two most important characteristics of batch process, one is the presence of "stay" or "interruption" in the process, the other is the product production is spaced, that is, there are batches of products and a batch of production can only get a fixed amount of products. In other words, for each batch of production, a fixed amount of raw materials react according to the sequence of reaction steps, resulting in a limited and fixed amount of products; Then a fixed amount of raw materials are put in and the next batch of reactions are carried out in the same process to produce a limited and fixed amount of products.

A batch process is realized in two ways: 1) by using a number of reactors respectively (e.g., flasks, reaction kettles, etc.), in which each reaction step is carried out in one of the reactors; 2) by one reactor (e.g., flask, reaction kettle, etc.), in which each reaction step is completed successively in the reactor; and multiple raw materials need to be added successively according to the reaction procedure during the production, which in other word after each reaction step, there is "stay", and waiting for addition of raw materials for next reaction step. Some literatures also call way 2 as continuous, which is essentially batch, because there is a "stay" in the process, in order to wait for feeding, or to adjust the appropriate temperature for the next reaction step(for example, heating, cooling or temperature holding).

In recent years, there have also been some reports on the attempts of "continuous" reaction to produce phenylhydrazine salt and substituted phenylhydrazine salt. They are realized by modification of existing devices and process methods, or continuous operation in some steps. The processes above only solved some problems to some extent, such as the high risk of diazotization, tedious operation in some steps, etc., but not completely, which is because the whole process is still a batch process in essence not a complete continuous process (diazotization, reduction and acidic hydrolysis and salifying).

Chinese patent CN101209980A and CN101550091A respectively disclosed the methods that can be used for industrial production to prepare 4-trifluoromethylphenylhydrazine hydrochloride and 4-cyanphenylhydrazine hydrochloride by "one-pot" operation. Two steps of diazotization and reduction are continuously operated. Diazonium salt is prepared with sodium nitrite by diazotization reaction in hydrochloric acid solution, and then reduced by stannic chloride in solution. Corresponding substituted phenylhydrazine salt is obtained after filtration and washing, and yields can reach above 75%. However, each of the so-called "continuous" reactions is still used in a conventional batch reactor, and the "one-pot" is actually that two reaction steps are completed successively in the same reactor, avoiding the material transferation operation during cooperation with a number of reaction kettles. But because there is still a "stay" in the process, such as waiting for reaction completing, feeding time and so on, or adjusting to a suitable temperature for the next reaction (e. g., heating, cooling or temperature holding), which is in essence also batch-type, and still belongs to a batch process (way 2 of the batch process as described above).

Chinese patent CN106315879A disclosed a method for preparing phenylhydrazine hydrochloride in industrial production by the combination of continuous operation and batch operation with reaction kettle. Although the diazotization is continuous operation, the reaction kettle is still used in the reduction and acidic hydrolysis and salifying. The two steps of the process are batch-type, and the whole process of synthesizing phenylhydrazine hydrochloride is still batch process in essence. Although the diazotization is a continuous operation, which partly solves the safety risks of the diazotization reaction, in the process, the reduction and acidic hydrolysis and salifying need several hours in total, and after acidic hydrolysis and salifying, neutralization, distillation and other purification steps are required, which result in a long total reaction time in the process. Therefore, this process is a batch process, and it fails to fundamentally solve the problems of long reaction time, low production efficiency, low purity of product after acidic hydrolysis and salifying, high production energy consumption and high cost.

Org. Process Res. Dev. 2015, 19, 892 and China patent CN104744295A disclosed a method for preparing o-ethylphenylhydrazine hydrochloride in industrial production by the combination of continuous operation with pipes and batch operation with reaction kettles. Although both the diazotization and reduction are continuous operation, there are still the following problems: 1) the acidic hydrolysis and salifying of the above method still depends on the reaction kettle (acidification kettle); 2) the reaction time is too long, 1.5 to 3 hours are required before concentrated hydrochloric acid is added, and the time including hydrolysis will exceed 2 hours; 3) purification is still required after hydrolysis, and organic solvent extraction is used, which has potential environmental pollution and environmental protection risks. It can be seen that the whole process for the synthesis of o-ethylphenylhydrazine hydrochloride is still essentially a batch process, which cannot avoid the problems of long time, tedious operation, low production efficiency, low purity of product after acidic hydrolysis and salifying, large energy consumption and high cost.

The improvement of the existing device and process method, to a certain extent, has solved the high risk of the diazotization step in the production of phenylhydrazine salt and substituted phenylhydrazine salt, as well as the continuous operation problem of diazotization and reduction steps. But there are still the following problems:

1. Phenylhydrazine salts and substituted phenylhydrazine salts synthesis processes all contain one or more batch-type steps. It cannot be a whole complete continuous process. In addition, reduction and acidic hydrolysis and salifying steps are usually carried out at 100° C. and the reaction rate is slow, which lead to long whole process reaction time, low production efficiency, high energy consumption and cost in the production process.
2. Due to the long reaction time and many by-products in the existing process, the purity of phenylhydrazine salts and substituted phenylhydrazine salts after acidic hydrolysis and salifying is not high, generally around 90%. In production, additional purification steps extraction with organic solvents toluene), washing (e.g., pickling or washing), recrystallization, etc.) are often required to obtain phenylhydrazine salts and substituted phenylhydrazine salts of high purity. Although the purity of the product after purification can reach more than 98%, these steps further reduce the product yield (usually about 80%) and production efficiency, and increase production costs.
3. That only a reactor is used to complete the production of different phenylhydrazine salts and substituted phenylhydrazine salts with meeting the demands of high purity, high yield and high production efficiency, has not been seen in the existing process. In other words, the existing process and its corresponding reactor have poor flexibility, and cannot meet the requirements of high efficiency, high quality and wide applicability in the production of different phenylhydrazine salts and substituted phenylhydrazine salts at the same time.

The acidic hydrolysis and salifying step in existing process generally remains a batch process. The main reasons are as follows: First, the batch-type operation of adding acid and low reaction temperature (mostly no more than 100° C.) makes slow reaction rate, long reaction time, and causing a large number of compounds 6 and 7 accumulation; Second, the lower reaction temperature also reduces the solubility of compounds 6 and 7 and product phenylhydrazine salts and substituted phenylhydrazine salts in the reaction system. The above problems eventually lead to the large amount of compounds 6, 7 and phenylhydrazine salts and substituted phenylhydrazine salts separating out in the reaction system, and the large amount of solids in the reaction system poses the potential risk of blockage, making the continuous process unable to be applied.

In addition, it should be pointed out that even if the reaction conditions in existing process of acidic hydrolysis and salifying achieve continuous operation, because the reaction time is too long, the technical cost of continuous process equipment application rises, which hinders the practical industrial application of continuous process.

Although the production process of phenylhydrazine salts and substituted phenylhydrazine salts is similar to some extent, the reaction steps mainly contain diazotization of aniline or substituted aniline, reduction by sodium sulfite or stannous chloride and acidic hydrolysis and salifying to get phenylhydrazine salts and substituted phenylhydrazine salts. But, structural differences of phenylhydrazine salts and substituted phenylhydrazine salts (such as different types and sites of substituents on the benzene ring), may cause different physical and chemical properties (such as boiling point, solubility, reactivity and stability, etc.) of raw materials (such as compound 1), reaction intermediates (for example, compounds 2, 3, 5, 6 and 7) and product (for example, compound 4), leading to different synthetic routes and different process conditions of diazotization, reduction and acidic hydrolysis and salifying in production for different phenylhydrazine salts and substituted phenylhydrazine salts. It is difficult to learn from each other, and unable to transplant from each other. In addition, the whole process takes too long time, and the operation process is too tedious. These problems make it difficult to integrate into a highly integrated technical solution with making ends meet. In most of existing processes, process operations, conditions and parameters are specially designed and developed according to the physical and chemical properties of the specific compounds in the process, resulting low flexibility of production process and device (reactor). In other words, one reactor is hard to satisfy the requirements for synthesis of different phenylhydrazine salts and substituted phenylhydrazine salts with high efficiency, high yield and high purity at the same time.

In addition, due to the long reaction time, poor reaction selectivity and many by-products in the existing process of phenylhydrazine salts and substituted phenylhydrazine salts, the product purity after acidic hydrolysis and salifying is not high generally around 90%. Additional purification steps (e.g., extraction with organic solvents (e.g., toluene), washing (e.g., pickling or washing), recrystallization, etc.) are required in production to obtain phenylhydrazine salts and substituted phenylhydrazine salts of high purity. Although the purity of the product after purification can reach more than 98%, these steps further reduce the production efficiency and product yield (usually about 80%), and increase the cost.

Among the existing processes, there is no solution to the problems of continuous whole process, long process time and low production efficiency with meeting the demands of high purity and high yield of phenylhydrazine salts and substituted phenylhydrazine salts. Also, there is no process in which physical properties (such as melting and boiling point, thermal conductivity, heat capacity, solubility, etc.) and differences in reactivity of materials (raw materials, reaction intermediates and products) in the synthesis of different phenylhydrazine salts and substituted phenylhydrazine salts are considered to solve the problems of process selectivity and flexibility. Once all these problems are solved, the following advantages will be taken: high reaction efficiency (rapid reaction and high yield of target products), devices with good universality (the same reactor can be used to efficiently produce products with different substituent types and positions), better safety, simple operation and easy for large-scale in industrial production.

DETAILED DESCRIPTION OF THE INVENTION

In view of the shortcomings of existing processes, the technical problem to be solved in this invention is to provide a safe, flexible, easy to operate, efficient, easy for large-scale production and new whole-process continuous flow process for phenylhydrazine salts and substituted phenylhydrazine salts synthesis.

Continuous process refers to the production process in which each step of the production system is connected to each other to ensure continuous operation on the whole, but during each step operation, "stay" and "wait" are allowed. Continuous flow process, as a kind of fast, efficient and complete continuous process, has the characteristics of short time, high efficiency, easy operation, etc. During the whole process, raw materials are continuously added and products are continuously produced. During the whole process, the materials (that is the reaction mixture containing raw materials, intermediates, products, solvents, etc.) continuously flow, without interruption, without staying and waiting, that is, the products are continuously produced. It is a kind of "flow line" chemical production process. When the process operation reaches the steady state, the state parameters such as the composition and temperature of materials at any position in the reactor do not change with time and are a steady-state process, so the production process and product quality are both stable. In a process containing multi reaction steps, if some of the steps are continuous or steps hi the batch process are simply connected to each other, the process can be called a semi-continuous process; Only when all steps are continuous and the material flows continuously in the whole process, that is, continuously adding raw materials and continuously obtaining products, can it be called continuous flow process (or whole-process continuous process).

The production process of phenylhydrazine salts and substituted phenylhydrazine salts contains three steps of diazotization, reduction and acidic hydrolysis to salt. Only when these three steps all achieve the "flow line" type continuous reaction, can the production be the continuous flow process. That any one or two steps of the reaction are continuous, is just a semi-continuous process, rather than continuous flow process. It should be noted that it is more difficult to achieve the continuity for acidic hydrolysis and salifying than diazotization and reduction. According to the operations under the batch process conditions for acidic hydrolysis and salifying, the reaction time is long and a large number of solids separate out in the reaction posing the potential blockage risk, which are huge obstacles to the continuous flow process application.

To solve the problems existing in the existing process, the present invention provides a kind of phenylhydrazine salts and substituted phenylhydrazine salts continuous flow synthesis process. Acidic liquids of aniline or substituted aniline, diazotization reagents, reductants and acids are used as raw materials, and diazotization, reduction and acidic hydrolysis and salifying are successively carried out to obtain phenylhydrazine salts and substituted phenylhydrazine salts. Reaction route is as follows:

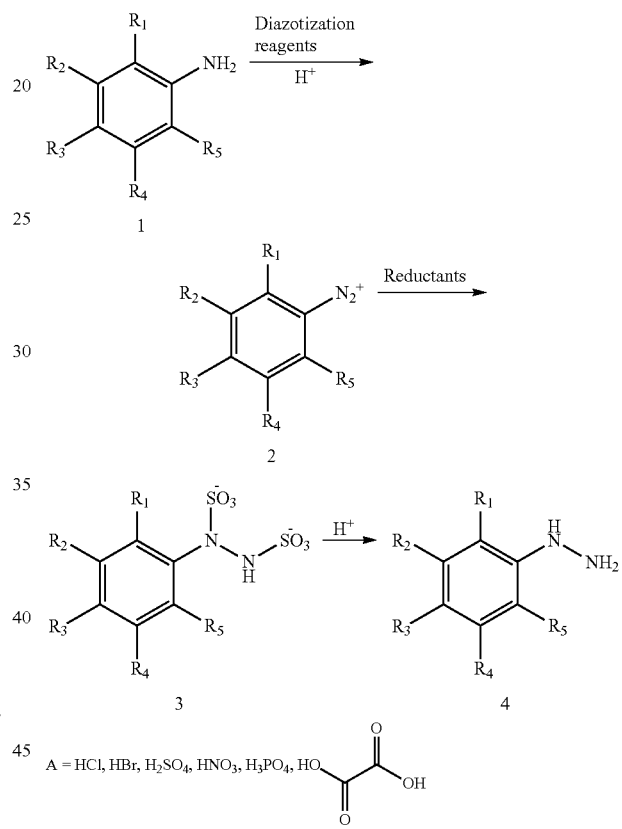

Where:
  $R_1$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;
  $R_2$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;
  $R_3$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;
  $R_4$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;
  $R_5$ is selected from —H, —F, —Cl, —Br, —CN, —$NO_2$, —$CF_3$, —COOH, $C_1$-$C_4$ alkoxy, $C_1$-$C_4$ saturated or unsaturated alkyl;
  A is selected from HCl, HBr, $H_2SO_4$, $HNO_3$, $H_3PO_4$, HOOC—COOH (oxalic acid).

The phenylhydrazine salts and the substituted phenylhydrazine salts are selected from phenylhydrazine hydrochloride, 4-hydrazinylbenzoic acid hydrochloride, 4-hydrazinylbenzenesulfonic acid hydrochloride, (2-fluorophenyl)hydrazine hydrochloride, (3-fluorophenyl)hydrazine hydrochloride, (4-fluorophenyl)hydrazine hydrochloride, (2,3-difluorophenyl)hydrazine hydrochloride, (2,4-difluorophenyl)hydrazine hydrochloride, (2,5-difluorophenyl)hydrazine hydrochloride, (2,6-difluorophenyl)hydrazine hydrochloride, (2,3,4-trifluorophenyl)hydrazine hydrochloride, (2,3,5-trifluorophenyl)hydrazine hydrochloride, (2,3,6-trifluorophenyl)hydrazine hydrochloride, (2,4,5-trifluorophenyl)hydrazine hydrochloride, (2,4,6-trifluorophenyl)hydrazine hydrochloride, (2,3,4,5-tetrafluorophenyl)hydrazine hydrochloride, (2,3,4,6-tetrafluorophenyl)hydrazine hydrochloride, (2,3,5,6-tetrafluorophenyl)hydrazine hydrochloride, (2-chlorophenyl)hydrazine hydrochloride, (3-chlorophenyl)hydrazine hydrochloride, (2,3-dichlorophenyl)hydrazine hydrochloride, (2,4-dichlorophenyl)hydrazine hydrochloride, (2,5-dichlorophenyl)hydrazine hydrochloride, (2,6-dichlorophenyl)hydrazine hydrochloride, (2,3,4-trichlorophenyl)hydrazine hydrochloride, (2,3,5-trichlorophenyl)hydrazine hydrochloride, (2,3,6-trichlorophenyl)hydrazine hydrochloride, (2,4,5-trichlorophenyl)hydrazine hydrochloride, (2,4,6-trichlorophenyl)hydrazine hydrochloride, (2,3,4,5-tetrachlorophenyl)hydrazine hydrochloride, (2,3,4,6-tetrachlorophenyl)hydrazine hydrochloride, (2,3,5,6-tetrachlorophenyl)hydrazine hydrochloride, (2-bromophenyl)hydrazine hydrochloride, (3-bromophenyl)hydrazine hydrochloride, (4-bromophenyl)hydrazine hydrochloride, (2,3-dibromophenyl)hydrazine hydrochloride, (2,4-dibromophenyl)hydrazine hydrochloride, (2,5-dibromophenyl)hydrazine hydrochloride, (2,6-dibromophenyl)hydrazine hydrochloride, (2,3,4-tribromophenyl)hydrazine hydrochloride, (2,3,5-tribromophenyl)hydrazine hydrochloride, (2,3,6-tribromophenyl)hydrazine hydrochloride, (2,4,5-tribromophenyl)hydrazine hydrochloride, (2,4,6-tribromophenyl)hydrazine hydrochloride, (2,3,4,5-tetrabromophenyl)hydrazine hydrochloride, (2,3,4,6-tetrabromophenyl)hydrazine hydrochloride, (2,3,5,6-tetrabromophenyl)hydrazine hydrochloride, (2-methoxyphenyl)hydrazine hydrochloride, (3-methoxyphenyl)hydrazine hydrochloride, (4-methoxyphenyl)hydrazine hydrochloride, (2,3-dimethoxyphenyl)hydrazine hydrochloride, (2,4-dimethoxyphenyl)hydrazine hydrochloride, (2,5-dimethoxyphenyl)hydrazine hydrochloride, (2,6-dimethoxyphenyl)hydrazine hydrochloride, (3,4-dimethoxyphenyl)hydrazine hydrochloride, (3,5-dimethoxyphenyl)hydrazine hydrochloride, (2-ethylphenyl)hydrazine hydrochloride, (3-ethylphenyl)hydrazine hydrochloride, (4-ethylphenyl)hydrazine hydrochloride, (2,3-diethylphenyl)hydrazine hydrochloride, (2,4-diethylphenyl)hydrazine hydrochloride, (2,5-diethylphenyl)hydrazine hydrochloride, (2,6-diethylphenyl)hydrazine hydrochloride, (2-(trifluoromethyl)phenyl)hydrazine hydrochloride, (3-(trifluoromethyl)phenyl)hydrazine hydrochloride, (4-(trifluoromethyl)phenyl)hydrazine hydrochloride, (2,3-bis(trifluoromethyl)phenyl)hydrazine hydrochloride, (2,4-bis(trifluoromethyl)phenyl)hydrazine hydrochloride, (2,5-bis(trifluoromethyl)phenyl)hydrazine hydrochloride, (2,6-bis(trifluoromethyl)phenyl)hydrazine hydrochloride, (2,4,6-tris(trifluoromethyl)phenyl)hydrazine hydrochloride, 2-hydrazinylbenzonitrile hydrochloride, 3-hydrazinylbenzonitrile hydrochloride, 4-hydrazinylbenzonitrile hydrochloride, 3-hydrazinylphthalonitrile hydrochloride, 4-hydrazinylisophthalonitrile hydrochloride, 2-hydrazinylterephthalonitrile hydrochloride, 2-hydrazinylisophtalonitrile hydrochloride, (2-fluoro-3-methoxyphenyl)hydrazine hydrochloride, (2-fluoro-4-methoxyphenyl)hydrazine hydrochloride, (2-fluoro-5-methoxyphenyl)hydrazine hydrochloride, (2-fluoro-6-methoxyphenyl)hydrazine hydrochloride, (3-fluoro-2-methoxyphenyl)hydrazine hydrochloride, (3-fluoro-4-methoxyphenyl)hydrazine hydrochloride, (3-fluoro-5-methoxyphenyl)hydrazine hydrochloride, (5-fluoro-2-methoxyphenyl)hydrazine hydrochloride, (4-fluoro-2-methoxyphenyl)hydrazine hydrochloride, (4-fluoro-3-methoxyphenyl)hydrazine hydrochloride, (2-choloro-3-methoxyphenyl)hydrazine hydrochloride, (2-choloro-4-methoxyphenyl)hydrazine hydrochloride, (2-choloro-5-methoxyphenyl)hydrazine hydrochloride, (2-choloro-6-methoxyphenyl)hydrazine hydrochloride, (3-choloro-2-methoxyphenyl)hydrazine hydrochloride, (3-choloro-4-methoxyphenyl)hydrazine hydrochloride, (3-choloro-5-methoxyphenyl)hydrazine hydrochloride, (5-choloro-2-methoxyphenyl)hydrazine hydrochloride, (4-choloro-2-methoxyphenyl)hydrazine hydrochloride, (4-choloro-3-methoxyphenyl)hydrazine hydrochloride, (2-nitrophenyl)hydrazine hydrochloride, (3-nitrophenyl)hydrazine hydrochloride, (4-nitrophenyl)hydrazine hydrochloride, (2-methoxy-3-nitrophenyl)hydrazine hydrochloride, (2-methoxy-4-nitrophenyl)hydrazine hydrochloride, (2-methoxy-5-nitrophenyl)hydrazine hydrochloride, (2-methoxy-6-nitrophenyl)hydrazine hydrochloride, (3-methoxy-2-nitrophenyl)hydrazine hydrochloride, (4-methoxy-2-nitrophenyl)hydrazine hydrochloride, (5-methoxy-2-nitrophenyl)hydrazine hydrochloride, (3-methoxy-5-nitrophenyl)hydrazine hydrochloride, (3-methoxy-4-nitrophenyl)hydrazine hydrochloride, (4-methoxy-3-nitrophenyl)hydrazine hydrochloride, (4-bromo-2-fluorophenyl)hydrazine hydrochloride, 2-hydrazinylbenzoic acid hydrochloride, 3-hydrazinylbenzoic acid hydrochloride, (4-chloro-2-fluorophenyl)hydrazine hydrochloride, 3-fluoro-4-hydrazinylbenzonitrile hydrochloride, (4-ethoxyphenyl)hydrazine hydrochloride, (4-propoxyphenyl)hydrazine hydrochloride, (4-butoxyphenyl)hydrazine hydrochloride, (3-isopropylphenyl)hydrazine hydrochloride, (4-propylphenyl)hydrazine hydrochloride, (4-vinylphenyl)hydrazine hydrochloride, (4-allylphenyl)hydrazine hydrochloride, (4-(but-3-en-1-yl)phenyl)hydrazine hydrochloride; phenylhydrazine hydrobromide, 4-hydrazinylbenzoic acid hydrobromide, 4-hydrazinylbenzenesulfonic acid hydrobromide, (2-fluorophenyl)hydrazine hydrobromide, (3-fluorophenyl)hydrazine hydrobromide, (4-fluorophenyl)hydrazine hydrobromide, (2,3-difluorophenyl)hydrazine hydrobromide, (2,4-difluorophenyl)hydrazine hydrobromide, (2,5-difluorophenyl)hydrazine hydrobromide, (2,6-difluorophenyl)hydrazine hydrobromide, (2,3,4-trifluorophenyl)hydrazine hydrobromide, (2,3,5-trifluorophenyl)hydrazine hydrobromide, (2,3,6-trifluorophenyl)hydrazine hydrobromide, (2,4,5-trifluorophenyl)hydrazine hydrobromide, (2,4,6-trifluorophenyl)hydrazine hydrobromide, (2,3,4,5-tetrafluorophenyl)hydrazine hydrobromide, (2,3,4,6-tetrafluorophenyl)hydrazine hydrobromide, (2,3,5,6-tetrafluorophenyl)hydrazine hydrobromide, (2-chlorophenyl)hydrazine hydrobromide, (3-chlorophenyl)hydrazine hydrobromide, (2,3-dichlorophenyl)hydrazine hydrobromide, (2,4-dichlorophenyl)hydrazine hydrobromide, (2,5-dichlorophenyl)hydrazine hydrobromide, (2,6-dichlorophenyl)hydrazine hydrobromide, (2,3,4-trichlorophenyl)hydrazine hydrobromide, (2,3,5-trichlorophenyl)hydrazine hydrobromide, (2,3,6-trichlorophenyl)hydrazine hydrobromide, (2,4,5-trichlorophenyl)hydrazine hydrobromide, (2,4,6-trichlorophenyl)hydrazine hydrobromide, (2,3,4,5-tetrachlorophenyl)hydrazine hydrobromide, (2,3,4,6- tetrachlorophenyl)hydrazine hydrobromide, (2,3,5,6-tetrachlorophenyl)hydrazine hydrobromide, (2-bromophenyl)hydrazine hydrobromide, (3-bromophenyl)hydrazine hydrobromide, (4-bromophenyl)hydrazine hydrobromide, (2,3-dibromophenyl)hydrazine hydrobromide, (2,4-dibromophenyl)hydrazine hydrobromide, (2,5-dibromophenyl)hydrazine hydrobromide, (2,6-dibromophenyl)hydrazine hydrobromide, (2,3,4-tribromophenyl)hydrazine hydrobromide, (2,3,5-tribromophenyl)hydrazine hydrobromide, (2,3,6-tribromophenyl)hydrazine hydrobromide, (2,4,5-tribromophenyl)hydrazine hydrobromide, (2,4,6-tribromophenyl)hydrazine hydrobromide, (2,3,4,5-tetrabromophenyl)hydrazine hydrobromide, (2,3,4,6-tetrabromophenyl)hydrazine hydrobromide, (2,3,5,6-tetrabromophenyl)hydrazine hydrobromide, (2-methoxyphenyl)hydrazine hydrobromide, (3-methoxyphenyl)hydrazine hydrobromide, (4-methoxyphenyl)hydrazine hydrobromide, (2,3-dimethoxyphenyl)hydrazine hydrobromide, (2,4-dimethoxyphenyl)hydrazine hydrobromide, (2,5-dimethoxyphenyl)hydrazine hydrobromide, (2,6-dimethoxyphenyl)hydrazine hydrobromide, (3,4-dimethoxyphenyl)hydrazine hydrobromide, (3,5-dimethoxyphenyl)hydrazine hydrobromide, (2-ethylphenyl)hydrazine hydrobromide, (3-ethylphenyl)hydrazine hydrobromide, (4-ethylphenyl)hydrazine hydrobromide, (2,3-diethylphenyl)hydrazine hydrobromide, (2,4-diethylphenyl)hydrazine hydrobromide, (2,5-diethylphenyl)hydrazine hydrobromide, (2,6-diethylphenyl)hydrazine hydrobromide, (2-(trifluoromethyl)phenyl)hydrazine hydrobromide, (3-(trifluoromethyl)phenyl)hydrazine hydrobromide, (4-(trifluoromethyl)phenyl)hydrazine hydrobromide, (2,3-bis(trifluoromethyl)phenyl)hydrazine hydrobromide, (2,4-bis(trifluoromethyl)phenyl)hydrazine hydrobromide, (2,5-bis(trifluoromethyl)phenyl)hydrazine hydrobromide, (2,6-bis(trifluoromethyl)phenyl)hydrazine hydrobromide, (2,4,6-tris(trifluoromethyl)phenyl)hydrazine hydrobromide, 2-hydrazinylbenzonitrile hydrobromide, 3-hydrazinylbenzonitrile hydrobromide, 4-hydrazinylbenzonitrile hydrobromide, 3-hydrazinylphthalonitrile hydrobromide, 4-hydrazinylisophthalonitrile hydrobromide, 2-hydrazinylterephthalonitrile hydrobromide, 2-hydrazinylisophthalonitrile hydrobromide, (2-fluoro-3-methoxyphenyl)hydrazine hydrobromide, (2-fluoro-4-methoxyphenyl)hydrazine hydrobromide, (2-fluoro-5-methoxyphenyl)hydrazine hydrobromide, (2-fluoro-6-methoxyphenyl)hydrazine hydrobromide, (3-fluoro-2-methoxyphenyl)hydrazine hydrobromide, (3-fluoro-4-methoxyphenyl)hydrazine hydrobromide, (3-fluoro-5-methoxyphenyl)hydrazine hydrobromide, (5-fluoro-2-methoxyphenyl)hydrazine hydrobromide, (4-fluoro-2-methoxyphenyl)hydrazine hydrobromide, (4-fluoro-3-methoxyphenyl)hydrazine hydrobromide, (2-choloro-3-methoxyphenyl)hydrazine hydrobromide, (2-choloro-4-methoxyphenyl)hydrazine hydrobromide, (2-choloro-5-methoxyphenyl)hydrazine hydrobromide, (2-choloro-6-methoxyphenyl)hydrazine hydrobromide, (3-choloro-2-methoxyphenyl)hydrazine hydrobromide, (3-choloro-4-methoxyphenyl)hydrazine hydrobromide, (3-choloro-5-methoxyphenyl)hydrazine hydrobromide, (5-choloro-2-methoxyphenyl)hydrazine hydrobromide, (4-choloro-2-methoxyphenyl)hydrazine hydrobromide, (4-choloro-3-methoxyphenyl)hydrazine hydrobromide, (2-nitrophenyl)hydrazine hydrobromide, (3-nitrophenyl)hydrazine hydrobromide, (4-nitrophenyl)hydrazine hydrobromide, (2-methoxy-3-nitrophenyl)hydrazine hydrobromide, (2-methoxy-4-nitrophenyl)hydrazine hydrobromide, (2-methoxy-5-nitrophenyl)hydrazine hydrobromide, (2-methoxy-6-nitrophenyl)hydrazine hydrobromide, (3-methoxy-2-nitrophenyl)hydrazine hydrobromide, (4-methoxy-2-nitrophenyl)hydrazine hydrobromide, (5-methoxy-2-nitrophenyl)hydrazine hydrobromide, (3-methoxy-5-nitrophenyl)hydrazine hydrobromide, (3-methoxy-4-nitrophenyl)hydrazine hydrobromide, (4-methoxy-3-nitrophenyl)hydrazine hydrobromide, (4-bromo-2-fluorophenyl)hydrazine hydrobromide, 2-hydrazinylbenzoic acid hydrobromide, 3-hydrazinylbenzoic acid hydrobromide, (4-chloro-2-fluorophenyl)hydrazine hydrobromide, 3-fluoro-4-hydrazinylbenzonitrile hydrobromide, (4-ethoxyphenyl)hydrazine hydrobromide, (4-propoxyphenyl)hydrazine hydrobromide, (4-butoxyphenyl)hydrazine hydrobromide, (3-isopropylphenyl)hydrazine hydrobromide, (4-propylphenyl)hydrazine hydrobromide, (4-vinylphenyl)hydrazine hydrobromide, (4-allylphenyl)hydrazine hydrobromide, (4-(but-3-en-1-yl)phenyl)hydrazine hydrobromide; phenylhydrazine sulfate, 4-hydrazinylbenzoic acid sulfate, 4-hydrazinylbenzenesulfonic acid sulfate, (2-fluorophenyl)hydrazine sulfate, (3-fluorophenyl)hydrazine sulfate, (4-fluorophenyl)hydrazine sulfate, (2,3-difluorophenyl)hydrazine sulfate, (2,4-difluorophenyl)hydrazine sulfate, (2,5-difluorophenyl)hydrazine sulfate, (2,6-difluorophenyl)hydrazine sulfate, (2,3,4-trifluorophenyl)hydrazine sulfate, (2,3,5-trifluorophenyl)hydrazine sulfate, (2,3,6-trifluorophenyl)hydrazine sulfate, (2,4,5-trifluorophenyl)hydrazine sulfate, (2,4,6-trifluorophenyl)hydrazine sulfate, (2,3,4,5-tetrafluorophenyl)hydrazine sulfate, (2,3,4,6-tetrafluorophenyl)hydrazine sulfate, (2,3,5,6-tetrafluorophenyl)hydrazine sulfate, (2-chlorophenyl)hydrazine sulfate, (3-chlorophenyl)hydrazine sulfate, (2,3-dichlorophenyl)hydrazine sulfate, (2,4-dichlorophenyl)hydrazine sulfate, (2,5-dichlorophenyl)hydrazine sulfate, (2,6-dichlorophenyl)hydrazine sulfate, (2,3,4-trichlorophenyl)hydrazine sulfate, (2,3,5-trichlorophenyl)hydrazine sulfate, (2,3,6-trichlorophenyl)hydrazine sulfate, (2,4,5-trichlorophenyl)hydrazine sulfate, (2,4,6-trichlorophenyl)hydrazine sulfate, (2,3,4,5-tetrachlorophenyl)hydrazine sulfate, (2,3,4,6-tetrachlorophenyl)hydrazine sulfate, (2,3,5,6-tetrachlorophenyl)hydrazine sulfate, (2-bromophenyl)hydrazine sulfate, (3-bromophenyl)hydrazine sulfate, (4-bromophenyl)hydrazine sulfate, (2,3-dibromophenyl)hydrazine sulfate, (2,4-dibromophenyl)hydrazine sulfate, (2,5-dibromophenyl)hydrazine sulfate, (2,6-dibromophenyl)hydrazine sulfate, (2,3,4-tribromophenyl)hydrazine sulfate, (2,3,5-tribromophenyl)hydrazine sulfate, (2,3,6-tribromophenyl)hydrazine sulfate, (2,4,5-tribromophenyl)hydrazine sulfate, (2,4,6-tribromophenyl)hydrazine sulfate, (2,3,4,5-tetrabromophenyl)hydrazine sulfate, (2,3,4,6-tetrabromophenyl)hydrazine sulfate, (2,3,5,6-tetrabromophenyl)hydrazine sulfate, (2-methoxyphenyl)hydrazine sulfate, (3-methoxyphenyl)hydrazine sulfate, (4-methoxyphenyl)hydrazine sulfate, (2,3-dimethoxyphenyl)hydrazine sulfate, (2,4-dimethoxyphenyl)hydrazine sulfate, (2,5-dimethoxyphenyl)hydrazine sulfate, (2,6-dimethoxyphenyl)hydrazine sulfate, (3,4-dimethoxyphenyl)hydrazine sulfate, (3,5-dimethoxyphenyl)hydrazine sulfate, (2-ethylphenyl)hydrazine sulfate, (3-ethylphenyl)hydrazine sulfate, (4-ethylphenyl)hydrazine sulfate, (2,3-diethylphenyl)hydrazine sulfate, (2,4-diethylphenyl)hydrazine sulfate, (2,5-diethylphenyl)hydrazine sulfate, (2,6-diethylphenyl)hydrazine sulfate, (2-(trifluoromethyl)phenyl)hydrazine sulfate, (3-(trifluoromethyl)phenyl)hydrazine sulfate, (4-(trifluoromethyl)phenyl)hydrazine sulfate, (2,3-bis(trifluoromethyl)phenyl)hydrazine sulfate, (2,4-bis(trifluoromethyl)phenyl)hydrazine sulfate, (2,5-bis(trifluoromethyl)phenyl)hydrazine sulfate, (2,6-bis(trifluoromethyl)phenyl)hydrazine sulfate, (2,4,6-tris(trifluoromethyl)phenyl)hydrazine sulfate, 2-hydrazinylbenzonitrile sulfate, 3-hydrazinylbenzonitrile sulfate, 4-hydrazinylbenzonitrile sulfate, 3-hydrazinylphthalonitrile sulfate, 4-hydrazinylisophthalonitrile sulfate, 2-hydrazinylterephthalonitrile sulfate, 2-hydrazinylisophthalonitrile sulfate, (2-fluoro-3-methoxyphenyl)hydrazine sulfate, (2-fluoro-4-methoxyphenyl)hydrazine sulfate, (2-fluoro-5-methoxyphenyl)hydrazine sulfate, (2-fluoro-6-methoxyphenyl)hydrazine sulfate, (3-fluoro-2-methoxyphenyl)hydrazine sulfate, (3-fluoro-4-methoxyphenyl)hydrazine sulfate, (3-fluoro-5-methoxyphenyl)hydrazine sulfate, (5-fluoro-2-methoxyphenyl)hydrazine sulfate, (4-fluoro-2-methoxyphenyl)hydrazine sulfate, (4-fluoro-3-methoxyphenyl)hydrazine sulfate, (2-choloro-3-methoxyphenyl)hydrazine sulfate, (2-choloro-4-methoxyphenyl)hydrazine sulfate, (2-choloro-5-methoxyphenyl)hydrazine sulfate, (2-choloro-6-methoxyphenyl)hydrazine sulfate, (3-choloro-2-methoxyphenyl)hydrazine sulfate, (3-choloro-4-methoxyphenyl)hydrazine sulfate, (3-choloro-5-methoxyphenyl)hydrazine sulfate, (5-choloro-2-methoxyphenyl)hydrazine sulfate, (4-choloro-2-methoxyphenyl)hydrazine sulfate, (4-choloro-3-methoxyphenyl)hydrazine sulfate, (2-nitrophenyl)hydrazine sulfate, (3-nitrophenyl)hydrazine sulfate, (4-nitrophenyl)hydrazine sulfate, (2-methoxy-3-nitrophenyl)hydrazine sulfate, (2-methoxy-4-nitrophenyl)hydrazine sulfate, (2-methoxy-5-nitrophenyl)hydrazine sulfate, (2-methoxy-6-nitrophenyl)hydrazine sulfate, (3-methoxy-2-nitrophenyl)hydrazine sulfate, (4-methoxy-2-nitrophenyl)hydrazine sulfate, (5-methoxy-2-nitrophenyl)hydrazine sulfate, (3-methoxy-5-nitrophenyl)hydrazine sulfate, (3-methoxy-4-nitrophenyl)hydrazine sulfate, (4-methoxy-3-nitrophenyl)hydrazine sulfate, (4-bromo-2-fluorophenyl)hydrazine sulfate, 2-hydrazinylbenzoic acid sulfate, 3-hydrazinylbenzoic acid sulfate, (4-chloro-2-fluorophenyl)hydrazine sulfate, 3-fluoro-4-hydrazinylbenzonitrile sulfate, (4-ethoxyphenyl)hydrazine sulfate, (4-propoxyphenyl)hydrazine sulfate, (4-butoxyphenyl)hydrazine sulfate, (3-isopropylphenyl)hydrazine sulfate, (4-propylphenyl)hydrazine sulfate, (4-vinylphenyl)hydrazine sulfate, (4-allylphenyl)hydrazine sulfate, (4-(but-3-en-1-yl)phenyl)hydrazine sulfate; phenylhydrazine oxalate, 4-hydrazinylbenzoic acid oxalate, 4-hydrazinylbenzenesulfonic acid oxalate, (2-fluorophenyl)hydrazine oxalate, (3-fluorophenyl)hydrazine oxalate, (4-fluorophenyl)hydrazine oxalate, (2,3-difluorophenyl)hydrazine oxalate, (2,4-difluorophenyl)hydrazine oxalate, (2,5-difluorophenyl)hydrazine oxalate, (2,6-difluorophenyl)hydrazine oxalate, (2,3,4-trifluorophenyl)hydrazine oxalate, (2,3,5-trifluorophenyl)hydrazine oxalate, (2,3,6-trifluorophenyl)hydrazine oxalate, (2,4,5-trifluorophenyl)hydrazine oxalate, (2,4,6-trifluorophenyl)hydrazine oxalate, (2,3,4,5-tetrafluorophenyl)hydrazine oxalate, (2,3,4,6-tetrafluorophenyl)hydrazine oxalate, (2,3,5,6-tetrafluorophenyl)hydrazine oxalate, (2-chlorophenyl)hydrazine oxalate, (3-chlorophenyl)hydrazine oxalate, (2,3-dichlorophenyl)hydrazine oxalate, (2,4-dichlorophenyl)hydrazine oxalate, (2,5-dichlorophenyl)hydrazine oxalate, (2,6-dichlorophenyl)hydrazine oxalate, (2,3,4-trichlorophenyl)hydrazine oxalate, (2,3,5-trichlorophenyl)hydrazine oxalate, (2,3,6-trichlorophenyl)hydrazine oxalate, (2,4,5-trichlorophenyl)hydrazine oxalate, (2,4,6-trichlorophenyl)hydrazine oxalate, (2,3,4,5-tetrachlorophenyl)hydrazine oxalate, (2,3,4,6-tetrachlorophenyl)hydrazine oxalate, (2,3,5,6-tetrachlorophenyl)hydrazine oxalate, (2-bromophenyl)hydrazine oxalate, (3-bromophenyl)hydrazine oxalate, (4-bromophenyl)hydrazine oxalate, (2,3-dibromophenyl)hydrazine oxalate, (2,4-dibromophenyl)hydrazine oxalate, (2,5-dibromophenyl)hydrazine oxalate, (2,6-dibromophenyl)hydrazine oxalate, (2,3,4-tribromophenyl)hydrazine oxalate, (2,3,5-tribromophenyl)hydrazine oxalate, (2,3,6-tribromophenyl)hydrazine oxalate, (2,4,5-tribromophenyl)hydrazine oxalate, (2,4,6-tribromophenyl)hydrazine oxalate, (2,3,4,5-tetrabromophenyl)hydrazine oxalate, (2,3,4,6-tetrabromophenyl)hydrazine oxalate, (2,3,5,6-tetrabromophenyl)hydrazine oxalate, (2-methoxyphenyl)hydrazine oxalate, (3-methoxyphenyl)hydrazine oxalate, (4-methoxyphenyl)hydrazine oxalate, (2,3-dimethoxyphenyl)hydrazine oxalate, (2,4-dimethoxyphenyl)hydrazine oxalate, (2,5-dimethoxyphenyl)hydrazine oxalate, (2,6-dimethoxyphenyl)hydrazine oxalate, (3,4-dimethoxyphenyl)hydrazine oxalate, (3,5-dimethoxyphenyl)hydrazine oxalate, (2-ethylphenyl)hydrazine oxalate, (3-ethylphenyl)hydrazine oxalate, (4-ethylphenyl)hydrazine oxalate, (2,3-diethylphenyl)hydrazine oxalate, (2,4-diethylphenyl)hydrazine oxalate, (2,5-diethylphenyl)hydrazine oxalate, (2,6-diethylphenyl)hydrazine oxalate, (2-(trifluoromethyl)phenyl)hydrazine oxalate, (3-(trifluoromethyl)phenyl)hydrazine oxalate, (4-(trifluoromethyl)phenyl)hydrazine oxalate, (2,3-bis(trifluoromethyl)phenyl)hydrazine oxalate, (2,4-bis(trifluoromethyl)phenyl)hydrazine oxalate, (2,5-bis(trifluoromethyl)phenyl)hydrazine oxalate, (2,6-bis(trifluoromethyl)phenyl)hydrazine oxalate, (2,4,6-tris(trifluoromethyl)phenyl)hydrazine oxalate, 2-hydrazinylbenzonitrile oxalate, 3-hydrazinylbenzonitrile oxalate, 4-hydrazinylbenzonitrile oxalate, 3-hydrazinylphthalonitrile oxalate, 4-hydrazinylisophthalonitrile oxalate, 2-hydrazinylterephthalonitrile oxalate, 2-hydrazinylisophthalonitrile oxalate, (2-fluoro-3-methoxyphenyl)hydrazine oxalate, (2-fluoro-4-methoxyphenyl)hydrazine oxalate, (2-fluoro-5-methoxyphenyl)hydrazine oxalate, (2-fluoro-6-methoxyphenyl)hydrazine oxalate, (3-fluoro-2-methoxyphenyl)hydrazine oxalate, (3-fluoro-4-methoxyphenyl)hydrazine oxalate, (3-fluoro-5-methoxyphenyl)hydrazine oxalate, (5-fluoro-2-methoxyphenyl)hydrazine oxalate, (4-fluoro-2-methoxyphenyl)hydrazine oxalate, (4-fluoro-3-methoxyphenyl)hydrazine oxalate, (2-choloro-3-methoxyphenyl)hydrazine oxalate, (2-choloro-4-methoxyphenyl)hydrazine oxalate, (2-choloro-5-methoxyphenyl)hydrazine oxalate, (2-choloro-6-methoxyphenyl)hydrazine oxalate, (3-choloro-2-methoxyphenyl)hydrazine oxalate, (3-choloro-4-methoxyphenyl)hydrazine oxalate, (3-choloro-5-methoxyphenyl)hydrazine oxalate, (5-choloro-2-methoxyphenyl)hydrazine oxalate, (4-choloro-2-methoxyphenyl)hydrazine oxalate, (4-choloro-3-methoxyphenyl)hydrazine oxalate, (2-nitrophenyl)hydrazine oxalate, (3-nitrophenyl)hydrazine oxalate, (4-nitrophenyl)hydrazine oxalate, (2-methoxy-3-nitrophenyl)hydrazine oxalate, (2-methoxy-4-nitrophenyl)hydrazine oxalate, (2-methoxy-5-nitrophenyl)hydrazine oxalate (2-methoxy-6-nitrophenyl)hydrazine oxalate, (3-methoxy-2-nitrophenyl)hydrazine oxalate, (4-methoxy-2-nitrophenyl)hydrazine oxalate, (5-methoxy-2-nitrophenyl)hydrazine oxalate, (3-methoxy-5-nitrophenyl)hydrazine oxalate, (3-methoxy-4-nitrophenyl)hydrazine oxalate, (4-methoxy-3-nitrophenyl)hydrazine oxalate, (4-bromo-2-fluorophenyl)hydrazine oxalate, 2-hydrazinylbenzoic acid oxalate, 3-hydrazinylbenzoic acid oxalate, (4-chloro-2-fluorophenyl)hydrazine oxalate, 3-fluoro-4-hydrazinylbenzonitrile oxalate, (4-ethoxyphenyl)hydrazine oxalate, (4-propoxyphenyl)hydrazine oxalate, (4-butoxyphenyl)hydrazine oxalate, (3-isopropylphenyl)hydrazine oxalate, (4-propylphenyl)hydrazine oxalate, (4-vinylphenyl)hydrazine oxalate, (4-allylphenyl)hydrazine oxalate, (4-(but-3-en-1-yl)phenyl)hydrazine oxalate; phenylhydrazine nitrate, 4-hydrazinylbenzoic acid nitrate, 4-hydrazinylbenzenesulfonic acid nitrate, (2-fluorophenyl)hydrazine nitrate, (3-fluorophenyl)hydrazine nitrate, (4-fluorophenyl)hydrazine nitrate, (2,3-difluorophenyl)hydrazine nitrate, (2,4-difluorophenyl)hydrazine nitrate, (2,5-difluorophenyl)hydrazine nitrate, (2,6-difluorophenyl)hydrazine nitrate, (2,3,4-trifluorophenyl)hydrazine nitrate, (2,3,5-trifluorophenyl)hydrazine nitrate, (2,3,6-trifluorophenyl)hydrazine nitrate, (2,4,5-trifluorophenyl)hydrazine nitrate, (2,4,6-trifluorophenyl)hydrazine nitrate, (2,3,4,5-tetrafluorophenyl)hydrazine nitrate, (2,3,4,6-tetrafluorophenyl)hydrazine nitrate, (2,3,5,6-tetrafluorophenyl)hydrazine nitrate, (2-chlorophenyl)hydrazine nitrate, (3-chlorophenyl)hydrazine nitrate, (2,3-dichlorophenyl)hydrazine nitrate, (2,4-dichlorophenyl)hydrazine nitrate, (2,5-dichlorophenyl)hydrazine nitrate, (2,6-dichlorophenyl)hydrazine nitrate, (2,3,4-trichlorophenyl)hydrazine nitrate, (2,3,5-trichlorophenyl)hydrazine nitrate, (2,3,6-trichlorophenyl)hydrazine nitrate, (2,4,5-trichlorophenyl)hydrazine nitrate, (2,4,6-trichlorophenyl)hydrazine nitrate, (2,3,4,5-tetrachlorophenyl)hydrazine nitrate, (2,3,4,6-tetrachlorophenyl)hydrazine nitrate, (2,3,5,6-tetrachlorophenyl)hydrazine nitrate, (2-bromophenyl)hydrazine nitrate, (3-bromophenyl)hydrazine nitrate, (4-bromophenyl)hydrazine nitrate, (2,3-dibromophenyl)hydrazine nitrate, (2,4-dibromophenyl)hydrazine nitrate, (2,5-dibromophenyl)hydrazine nitrate, (2,6-dibromophenyl)hydrazine nitrate, (2,3,4-tribromophenyl)hydrazine nitrate, (2,3,5-tribromophenyl)hydrazine nitrate, (2,3,6-tribromophenyl)hydrazine nitrate, (2,4,5-tribromophenyl)hydrazine nitrate, (2,4,6-tribromophenyl)hydrazine nitrate, (2,3,4,5-tetrabromophenyl)hydrazine nitrate, (2,3,4,6-tetrabromophenyl)hydrazine nitrate, (2,3,5,6-tetrabromophenyl)hydrazine nitrate, (2-methoxyphenyl)hydrazine nitrate, (3-methoxyphenyl)hydrazine nitrate, (4-methoxyphenyl)hydrazine nitrate, (2,3-dimethoxyphenyl)hydrazine nitrate, (2,4-dimethoxyphenyl)hydrazine nitrate, (2,5-dimethoxyphenyl)hydrazine nitrate, (2,6-dimethoxyphenyl)hydrazine nitrate, (3,4-dimethoxyphenyl)hydrazine nitrate, (3,5-dimethoxyphenyl)hydrazine nitrate, (2-ethylphenyl)hydrazine nitrate, (3-ethylphenyl)hydrazine nitrate, (4-ethylphenyl)hydrazine nitrate, (2,3-diethylphenyl)hydrazine nitrate, (2,4-diethylphenyl)hydrazine nitrate, (2,5-diethylphenyl)hydrazine nitrate, (2,6-diethylphenyl)hydrazine nitrate, (2-(trifluoromethyl)phenyl)hydrazine nitrate, (3-(trifluoromethyl)phenyl)hydrazine nitrate, (4-(trifluoromethyl)phenyl)hydrazine nitrate, (2,3-bis(trifluoromethyl)phenyl)hydrazine nitrate, (2,4-bis(trifluoromethyl)phenyl)hydrazine nitrate, (2,5-bis(trifluoromethyl)phenyl)hydrazine nitrate, (2,6-bis(trifluoromethyl)phenyl)hydrazine nitrate, (2,4,6-tris(trifluoromethyl)phenyl)hydrazine nitrate, 2-hydrazinylbenzonitrile nitrate, 3-hydrazinylbenzonitrile nitrate, 4-hydrazinylbenzonitrile nitrate, 3-hydrazinylphthalonitrile nitrate, 4-hydrazinylisophthalonitrile nitrate, 2-hydrazinylterephthalonitrile nitrate, 2-hydrazinylisophthalonitrile nitrate, (2-fluoro-3-methoxyphenyl)hydrazine nitrate, (2-fluoro-4-methoxyphenyl)hydrazine nitrate, (2-fluoro-5-methoxyphenyl)hydrazine nitrate, (2-fluoro-6-methoxyphenyl)hydrazine nitrate, (3-fluoro-2-methoxyphenyl)hydrazine nitrate, (3-fluoro-4-methoxyphenyl)hydrazine nitrate, (3-fluoro-5-methoxyphenyl)hydrazine nitrate, (5-fluoro-2-methoxyphenyl)hydrazine nitrate, (4-fluoro-2-methoxyphenyl)hydrazine nitrate, (4-fluoro-3-methoxyphenyl)hydrazine nitrate, (2-choloro-3-methoxyphenyl)hydrazine nitrate, (2-choloro-4-methoxyphenyl)hydrazine nitrate, (2-choloro-5-methoxyphenyl)hydrazine nitrate, (2-choloro-6-methoxyphenyl)hydrazine nitrate, (3-choloro-2-methoxyphenyl)hydrazine nitrate, (3-choloro-4-methoxyphenyl)hydrazine nitrate, (3-choloro-5-methoxyphenyl)hydrazine nitrate, (5-choloro-2-methoxyphenyl)hydrazine nitrate, (4-choloro-2-methoxyphenyl)hydrazine nitrate, (4-choloro-3-methoxyphenyl)hydrazine nitrate, (2-nitrophenyl)hydrazine nitrate, (3-nitrophenyl)hydrazine nitrate, (4-nitrophenyl)hydrazine nitrate, (2-methoxy-3-nitrophenyl)hydrazine nitrate, (2-methoxy-4-nitrophenyl)hydrazine nitrate, (2-methoxy-5-nitrophenyl)hydrazine nitrate, (2-methoxy-6-nitrophenyl)hydrazine nitrate, (3-methoxy-2-nitrophenyl)hydrazine nitrate, (4-methoxy-2-nitrophenyl)hydrazine nitrate, (5-methoxy-2-nitrophenyl)hydrazine nitrate, (3-methoxy-5-nitrophenyl)hydrazine nitrate, (3-methoxy-4-nitrophenyl)hydrazine nitrate, (4-methoxy-3-nitrophenyl)hydrazine nitrate, (4-bromo-2-fluorophenyl)hydrazine nitrate, 2-hydrazinylbenzoic acid nitrate, 3-hydrazinylbenzoic acid nitrate, (4-chloro-2-fluorophenyl)hydrazine nitrate, 3-fluoro-4-hydrazinylbenzonitrile nitrate, (4-ethoxyphenyl)hydrazine nitrate, (4-propoxyphenyl)hydrazine nitrate, (4-butoxyphenyl)hydrazine nitrate, (3-isopropylphenyl)hydrazine nitrate, (4-propylphenyl)hydrazine nitrate, (4-vinylphenyl)hydrazine nitrate, (4-allylphenyl)hydrazine nitrate, (4-(but-3-en-1-yl)phenyl)hydrazine nitrate; phenylhydrazine phosphate, 4-hydrazinylbenzoic acid phosphate, 4-hydrazinylbenzenesulfonic acid phosphate, (2-fluorophenyl)hydrazine phosphate, (3-fluorophenyl)hydrazine phosphate, (4-fluorophenyl)hydrazine phosphate, (2,3-difluorophenyl)hydrazine phosphate, (2,4-difluorophenyl)hydrazine phosphate, (2,5-difluorophenyl)hydrazine phosphate, (2,6-difluorophenyl)hydrazine phosphate, (2,3,4-trifluorophenyl)hydrazine phosphate, (2,3,5-trifluorophenyl)hydrazine phosphate, (2,3,6-trifluorophenyl)hydrazine phosphate, (2,4,5-trifluorophenyl)hydrazine phosphate, (2,4,6-trifluorophenyl)hydrazine phosphate, (2,3,4,5-tetrafluorophenyl)hydrazine phosphate, (2,3,4,6-tetrafluorophenyl)hydrazine phosphate, (2,3,5,6-tetrafluorophenyl)hydrazine phosphate, (2-chlorophenyl)hydrazine phosphate, (3-chlorophenyl)hydrazine phosphate, (2,3-dichlorophenyl)hydrazine phosphate, (2,4-dichlorophenyl)hydrazine phosphate, (2,5-dichlorophenyl)hydrazine phosphate, (2,6-dichlorophenyl)hydrazine phosphate, (2,3,4-trichlorophenyl)hydrazine phosphate, (2,3,5-trichlorophenyl)hydrazine phosphate, (2,3,6-trichlorophenyl)hydrazine phosphate, (2,4,5-trichlorophenyl)hydrazine phosphate, (2,4,6-trichlorophenyl)hydrazine phosphate, (2,3,4,5-tetrachlorophenyl)hydrazine phosphate, (2,3,4,6-tetrachlorophenyl)hydrazine phosphate, (2,3,5,6-tetrachlorophenyl)hydrazine phosphate, (2-bromophenyl)hydrazine phosphate, (3-bromophenyl)hydrazine phosphate, (4-bromophenyl)hydrazine phosphate, (2,3-dibromophenyl)hydrazine phosphate, (2,4-dibromophenyl)hydrazine phosphate, (2,5-dibromophenyl)hydrazine phosphate, (2,6-dibromophenyl)hydrazine phosphate, (2,3,4-tribromophenyl)hydrazine phosphate, (2,3,5-tribromophenyl)hydrazine phosphate, (2,3,6-tribromophenyl)hydrazine phosphate, (2,4,5-tribromophenyl)hydrazine phosphate, (2,4,6-tribromophenyl)hydrazine phosphate, (2,3,4,5-tetrabromophenyl)hydrazine phosphate, (2,3,4,6-tetrabromophenyl)hydrazine phosphate, (2,3,5,6-tetrabromophenyl)hydrazine phosphate, (2-methoxyphenyl)hydrazine phosphate, (3-methoxyphenyl)hydrazine phosphate, (4-methoxyphenyl)hydrazine phosphate, (2,3-dimethoxyphenyl)hydrazine phosphate, (2,4-dimethoxyphenyl)hydrazine phosphate, (2,5-dimethoxyphenyl)hydrazine phosphate, (2,6-dimethoxyphenyl)hydrazine phosphate, (3,4-dimethoxyphenyl)hydrazine phosphate, (3,5-dimethoxyphenyl)hydrazine phosphate, (2-ethylphenyl)hydrazine phosphate, (3-ethylphenyl)hydrazine phosphate, (4-ethylphenyl)hydrazine phosphate, (2,3-diethylphenyl)

hydrazine phosphate, (2,4-diethylphenyl)hydrazine phosphate, (2,5-diethylphenyl)hydrazine phosphate, (2,6-diethylphenyl)hydrazine phosphate, (2-(trifluoromethyl)phenyl)hydrazine phosphate, (3-(trifluoromethyl)phenyl)hydrazine phosphate, (4-(trifluoromethyl)phenyl)hydrazine phosphate, (2,3-bis(trifluoromethyl)phenyl)hydrazine phosphate, (2,4-bis(trifluoromethyl)phenyl)hydrazine phosphate, (2,5-bis(trifluoromethyl)phenyl)hydrazine phosphate, (2,6-bis(trifluoromethyl)phenyl)hydrazine phosphate, (2,4,6-tris(trifluoromethyl)phenyl)hydrazine phosphate, 2-hydrazinylbenzonitrile phosphate, 3-hydrazinylbenzonitrile phosphate, 4-hydrazinylbenzonitrile phosphate, 3-hydrazinylphthalonitrile phosphate, 4-hydrazinylisophthalonitrile phosphate, 2-hydrazinylterephthalonitrile phosphate, 2-hydrazinylisophthalonitrile phosphate, (2-fluoro-3-methoxyphenyl)hydrazine phosphate, (2-fluoro-4-methoxyphenyl)hydrazine phosphate, (2-fluoro-5-methoxyphenyl)hydrazine phosphate, (2-fluoro-6-methoxyphenyl)hydrazine phosphate, (3-fluoro-2-methoxyphenyl)hydrazine phosphate, (3-fluoro-4-methoxyphenyl)hydrazine phosphate, (3-fluoro-5-methoxyphenyl)hydrazine phosphate, (5-fluoro-2-methoxyphenyl)hydrazine phosphate, (4-fluoro-2-methoxyphenyl)hydrazine phosphate, (4-fluoro-3-methoxyphenyl)hydrazine phosphate, (2-choloro-3-methoxyphenyl)hydrazine phosphate, (2-choloro-4-methoxyphenyl)hydrazine phosphate, (2-choloro-5-methoxyphenyl)hydrazine phosphate, (2-choloro-6-methoxyphenyl)hydrazine phosphate, (3-choloro-2-methoxyphenyl)hydrazine phosphate, (3-choloro-4-methoxyphenyl)hydrazine phosphate, (3-choloro-5-methoxyphenyl)hydrazine phosphate, (5-choloro-2-methoxyphenyl)hydrazine phosphate, (4-choloro-2-methoxyphenyl)hydrazine phosphate, (4-choloro-3-methoxyphenyl)hydrazine phosphate, (2-nitrophenyl)hydrazine phosphate, (3-nitrophenyl)hydrazine phosphate, (4-nitrophenyl)hydrazine phosphate, (2-methoxy-3-nitrophenyl)hydrazine phosphate, (2-methoxy-4-nitrophenyl)hydrazine phosphate, (2-methoxy-5-nitrophenyl)hydrazine phosphate, (2-methoxy-6-nitrophenyl)hydrazine phosphate, (3-methoxy-2-nitrophenyl)hydrazine phosphate, (4-methoxy-2-nitrophenyl)hydrazine phosphate, (5-methoxy-2-nitrophenyl)hydrazine phosphate, (3-methoxy-5-nitrophenyl)hydrazine phosphate, (3-methoxy-4-nitrophenyl)hydrazine phosphate, (4-methoxy-3-nitrophenyl)hydrazine phosphate, (4-bromo-2-fluorophenyl)hydrazine phosphate, 2-hydrazinylbenzoic acid phosphate, 3-hydrazinylbenzoic acid phosphate, (4-chloro-2-fluorophenyl)hydrazine phosphate, 3-fluoro-4-hydrazinylbenzonitrile phosphate, (4-ethoxyphenyl)hydrazine phosphate, (4-propoxyphenyl)hydrazine phosphate, (4-butoxyphenyl)hydrazine phosphate, (3-isopropylphenyl)hydrazine phosphate, (4-propylphenyl)hydrazine phosphate, (4-vinylphenyl)hydrazine phosphate, (4-allylphenyl)hydrazine phosphate, (4-(but-3-en-1-yl)phenyl)hydrazine phosphate.

The invention innovatively provides a new continuous flow process for the synthesis of phenylhydrazine salts and substituted phenylhydrazine salts. In other words, it organically integrates the three steps of diazotization, reduction and acidic hydrolysis and salifying, in which acidic liquids of aniline or substituted aniline, diazotization reagents, reductants and acids as raw materials produce phenylhydrazine salts and substituted phenylhydrazine salts as product undergoing diazotization, reduction and acidic hydrolysis and salifying successively. The said synthesis process is carried out in an integrated reactor, which is an integrated solution. For the first time, the three-step reaction of diazotization, reduction and acidic hydrolysis and salifying was carried out in a reactor, which greatly shortened the reaction time and improved the reaction efficiency and product quality. In other words, the reaction raw materials (acidic liquids of aniline or substituted aniline, diazotization reagents, reductants and acids) are continuously added at the feed inlets of the integrated reactor, undergoing the diazotization, reduction and acidic hydrolysis and salifying successively in the integrated reactor, and the phenylhydrazine salts and substituted phenylhydrazine salts are obtained continuously at the outlets of the integrated reactor, of which the total reaction time is no more than 20 min. Compared with the traditional production process, the total reaction time is greatly shortened and the safely is greatly improved. In addition, the synthesis reaction process does not produce diazo-amino compounds, and the outlet products do not contain diazo-amino compounds, reduction reaction intermediates and reduction reaction products. The continuous flow process does not include additional purification steps, meant that no removal steps of by-products (for example, organic solvent extraction, washing or recrystallization steps) are included in the reaction process and the treatment of the reaction product. The structural formula of the diazo amino compound is as follows:

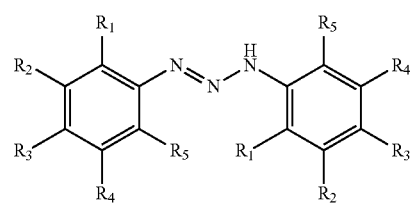

5

The mentioned structural formula of the reduction reaction intermediate anion is:

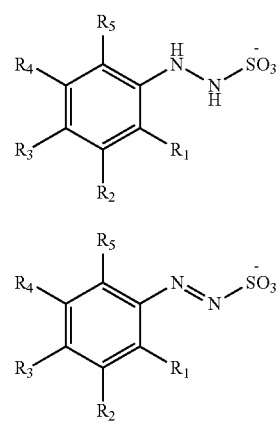

The mentioned structural formula of anion of the reduction reaction product is:

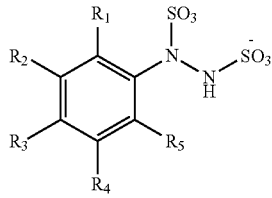

Where, the cations are selected from any metal cation or $NH_4^+$;

$R_1$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;

$R_2$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;

$R_3$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;

$R_4$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl;

$R_5$ is selected from —H, —F, —Cl, —Br, —CN, —$NO_2$, —$CF_3$, —$SO_3H$, —COOH, $C_1$-$C_4$ alkoxy, $C_1$-$C_4$ saturated or unsaturated alkyl.

The purity of the phenylhydrazine salts and the substituted phenylhydrazine salts directly prepared by the process without purification steps is no less than 95%. Further, the purity of the said phenylhydrazine salts and the substituted phenylhydrazine salts is no less than 98%. Further, the purity of the said phenylhydrazine salts and the substituted phenylhydrazine salts is no less than 99% and even no less than 99.9%. In the production, the purity of the said liquid of phenylhydrazine salts and substituted phenylhydrazine salts obtained at the outlet of the integrated reactor is no less than 95% determined by high performance liquid chromatography (HPLC). Further, the purity of the said liquid of phenylhydrazine salts and the substituted phenylhydrazine salts liquid is no less than 98%. Further, the purity of the said liquid of phenylhydrazine salts and the substituted phenylhydrazine salts is no less than 99% and even no less than 99.9%. After the steps of crystallization by cooling, filtration and drying, solid products of phenylhydrazine salts and substituted phenylhydrazine salts for sale can be obtained. Correspondingly, the purity of the solid product of phenylhydrazine salts and substituted phenylhydrazine salts is no less than 95%. Furthermore, the purity of the solid product of phenylhydrazine salt and substituted phenylhydrazine salt is no less than 98%. Furthermore, the purity of the solid product o phenylhydrazine salt and substituted phenylhydrazine salt is no less than 99% and even no less than 99.9%.

Further, the yield of the synthetic process is no less than 94%; Preferably, the ld is no less than 97%.

Further, the total reaction time mentioned above refers to the time from raw material entering the reactor to product outputting the reactor. In continuous flow process, it is also called residence time. Preferably, the total reaction time is 2~20 min; Preferably, the total reaction time is 3~17 min; Preferably, the total reaction time is 4~16 min; Preferably, the total reaction time is 5~13 min; Preferably, the total reaction time is 6~12 min; Preferably, the total reaction time is 7~11 min.

Further, the diazotization reagent is selected from nitrites, nitrosylsulfuric acid and nitrite esters. The nitrite can be selected from lithium nitrite, sodium nitrite, potassium nitrite, ammonium nitrite, magnesium nitrite, barium nitrite, calcium nitrite; Nitrite ester can be iso-amyl nitrite, n-butyl nitrite.

Further, the liquid concentration of the diazotization reagent is 10 wt %~95 wt %, preferably 20 wt %~40 wt %. The feed liquid of diazotization reagents may be liquid diazotization reagents, slurry or pulp of diazotization reagents, suspension, emulsion or solution of diazotization reagents.

Further, the mentioned reductants is selected from any one or any kinds of sulfates, bisulfates, thiosulfates, dithionites, pyrosulfates, ammonium hydroxide; preferably, the mentioned sulfate is selected from lithium sulfite, sodium sulfite, potassium sulfite, ammonium sulfite; Bisulfite is selected from lithium bisulfite, sodium bisulfite, potassium bisulfite, ammonium bisulfite, thiosulfate is selected from lithium thiosulfate, sodium thiosulfate, potassium thiosulfate and ammonium thiosulfate; dithionite is selected from lithium dithionite, sodium dithionite, potassium dithionite, ammonium dithionite; pyrosulfite is selected from lithium pyrosulfite, sodium pyrosulfite, potassium pyrosulfite and ammonium pyrosulfite.

Further, the concentration of the mentioned reductant feed liquid is 10 wt %~75%, preferably 15 wt %~30 wt %. The mentioned reductant feed liquid is selected from liquid reductants, slurry or pulp of reductants, suspension, emulsion or solution of reductants.

Further, the mentioned acid is selected from hydrochloric acid. hydrobromic acid, sulfuric acid, phosphoric acid, nitric acid, oxalic acid; preferably, the concentration of hydrochloric acid is 10 wt %~37 wt %, hydrobromic acid is 10 wt %~47 wt %, sulfuric acid is 10 wt %~98 wt %, phosphoric acid is 10 wt %~98 wt %, nitric acid is 10 wt %~68 wt %, and oxalic acid is 10 wt %~40 wt %; preferably, the concentration of hydrochloric acid is 15 wt %~36 wt %.

Further, the temperature of the diazotization reaction is 2~80° C., preferably 5~65° C., preferably 10~55° C., preferably 15~45° C., preferably 20~35° C. preferably 25~33° C., preferably 28~30° C.

Further, the temperature of the reduction reaction 40~130° C., preferably 50~125° C., preferably 70~120° C., preferably 90~120° C., preferably 95~118° C. preferably 105~115° C., preferably 110~115° C.

Further, the temperature of acidic hydrolysis and salifying is 40~130° C., preferably 70~130° C., preferably 90~130° C., preferably 95~125° C. preferably 100~125° C. preferably 105~125° C., preferably 110~125° C., preferably 115~120° C.

Further, the molar ratio of aniline or substituted aniline to diazotization reagent is 1:0.9~1.2; preferably 1:1.01~1.05.

Further, the molar ratio of aniline or substituted aniline to reductant is 1:2.0~8.0, preferably 1:2.5~3.0.

Further, the molar ratio of aniline or substituted aniline to acid is 1:3.0~10.0, preferably 1:4.0~4.9.

Structural differences of phenylhydrazine salts and substituted phenylhydrazine salts (such as different types and sites of substituents on the benzene ring), may cause different physical and chemical properties (such as boiling point, solubility, reactivity and stability, etc.) of raw materials (for example, compound 1), reaction intermediates (for example, compounds 2, 3, 5, 6 and 7) and product (for example, compound 4). Considering the differences in physical properties (e.g., melting and boiling points, thermal conductivity, heat capacity, solubility, etc.) and reactivity of materials (raw materials, reaction intermediates and products) involved in the synthesis of different phenylhydrazine salts and substituted phenylhydrazine salts, the applicant developed an integrated reactor with high integration. The reactor can be a modular structure, of which the modular design includes the module organization mode, the module number, and the modules contained in each temperature zone. The reactor is used for the synthesis of different phenylhydrazine salts and substituted phenylhydrazine salts. Only the specific adjustment of the process conditions and parameters, including the division and temperature setting of each temperature zone, the material concentration, the material ratio and the material flow rate, are needed to make them play a coordinated role and match with the reaction procedure so that the continuous flow process of corresponding phenylhydrazine salts and substituted phenylhydrazine salts could be realized. In other words, the integrated reactor has a flexible applicability for the synthesis of different phenylhydrazine salts and substituted phenylhydrazine salts. The material concentration includes the concentration of each raw material and the concentration of each intermediate product, the material ratio includes the ratio of each raw material and the ratio of each intermediate product, and the material flow rate includes the flow rate of each raw material and the flow rate of each intermediate product.

Further, the number of the inlets of the integrated reactor is one or more, the number of the outlets of the integrated reactor is one or more. The continuous addition may be raw materials added simultaneously.

Further, in order to match the phenylhydrazine salts and the substituted phenylhydrazine salts continuous flow process, the mentioned integrated reactor adopts modular structure, and contains multiple temperature zones, each of which independently contains more than one module or reactor module group, and is connected to each other. The reactor module group is composed of multiple reactor modules in series or in parallel. The reactor modules, the reactor module groups, each reactor module and reactor module groups are connected in series or parallel to each other. Among them, each reactor module has a large specific surface area and excellent mass and heat transfer performance, and is shaped to create well mixing of materials along the entire length of the channel in the whole process. In addition, each reactor module can achieve mixing, heat transfer and reaction independently. The integrated reactor may be one reactor or multiple reactors.

The acidic hydrolysis and salifying step in existing process generally remains a batch process. The main reasons are as follows: First, the batch-type operation of adding acid and low reaction temperature (mostly no more than 100° C.) makes slow reaction rate, long reaction time, and causing a large number of compounds 6 and 7 accumulation; Second, the lower reaction temperature also reduces the solubility of compounds 6 and 7 and product phenylhydrazine salts and substituted phenylhydrazine salts in the reaction system. The above problems eventually lead to the large amount of compounds 6, 7 and phenylhydrazine salts and substituted phenylhydrazine salts separating out in the reaction system, and the large amount of solids in the reaction system poses the potential risk of blockage, making the continuous process unable to be applied.

Based on the integrated reactor mentioned above, the invention optimizes the reaction procedure and improves the material fluidity, by combining different temperature zone division and temperature setting, and matching temperature with material concentration, ratio and flow rate, to solve the solid blockage problem in the acidic hydrolysis and salifying step completely and realize the continuous flow process of diazotization, reduction and acidic hydrolysis and salifying in the whole three-step process successfully. In addition, the high purity and high yield of the product were achieved while the continuity of the whole process realized. With the process of the invention, the purity of phenylhydrazine salts and substituted phenylhydrazine salts obtained after acidic hydrolysis and salifying without purification is more than 95% and the yield of it is more than 94%, and further the purity is even more than 99% and the yield is even more than 97%. The production efficiency is improved, and the high purity and yield of the products are realized at the same time.

Further, the mentioned integrated reactor adopts modular structure, and contains multiple temperature zones, each of which independently contains more than one reactor module or reactor module group. The reactor module group is composed of multiple reactor modules in series or in parallel, and each temperature zone is connected to each other.

Further, the temperature zones are connected in series or in parallel.

Further, the reactor modules, the reactor module groups, each reactor module and reactor module groups are connected in series or parallel to each other.

Further, the reactor module is any reactor that can realize continuous flow process; the mentioned reactor is any one or any kinds of micro-reactor, series coil reactor, tubular reactor. The said micro-reactor, also known as micro-structure reactor or micro-channel reactor, is a kind of equipment in which chemical reaction occurs in a limited area with a general lateral size of 1 mm or less, and the most typical form of such a limited area is the micro-size channel. A series coil reactor is a reactor composed of a coil reactor in series by means of a pipe, and a coil reactor is a reactor with coil pipes. Tubular reactor is a continuous operation reactor with tubular shape and large aspect ratio. This reactor can be very long: can be a single tube or multi-tube in parallel; can be empty or filled.

Further, each temperature zone may contain any one of the above reactors or a combination of any kinds of the above reactors Preferably, each temperature zone also further contains buffer vessel, which is a vessel with a certain volume, and is mainly used to buffer pressure fluctuations and balance flow differences of the system, making the system work more stable.

Further, channel length of the reactor module is 0.5~5 m.

Further, the channel diameter of the reactor shall be more than 0.5 mm, preferably the channel diameter of the reactor could be 0.5~1 mm, 1~3 mm, 3~5 mm, 5~6.35 mm, 6.35~12.7 mm, 12.7~25.4 mm, 25.4~55 mm.

Further, the material of the reactor can be metal, alloy, glass, silicon material, ceramic, carbon fiber, polymer, etc.

Further, the continuous flow process is carried out in an integrated reactor with four temperature zones, continuous flow process consists of the following steps:

(a) Under acidic conditions, aniline or substituted phenylamine is transported into temperature zone I, mixing with liquid of diazotization reagent, where diazotization reaction is completed to generate diazoate salt;

(b) The reductants aqueous solution is transported to the temperature zone II for pre-heating, and then mixes with the diazoate salt solution generated by the temperature zone I in the temperature zone III, and flows through the temperature zone III until the reaction is complete;

(c) The reaction liquid flowing out of zone III mixes with acid enters zone IV and flows through zone IV until the reaction is complete and phenylhydrazine salt or substituted phenylhydrazine salt is obtained.

Further, the temperature of the zone I is 2~80° C., preferably 5~65° C., preferably 10~55° C., preferably 15~45° C., preferably 20~35° C., preferably 25~33° C., preferably 28~30° C.

Further, the temperature of the zone II is 30~120° C., preferably 50~110° C., preferably 70~110° C., preferably 90~110° C., preferably 95~110° C., preferably 100~108° C., preferably 105~108° C.

Further, the temperature of the zones III is 40~130° C., preferably 50~125° C., preferably 70~120° C., preferably 90~120° C., preferably 95~118° C., preferably 105~115° C., preferably 110~115° C.

Further, the temperature of the zones IV is 40~130° C., preferably 70~130° C., preferably 90~130° C., preferably 95~125° C., preferably 100~125° C., preferably 105~125° C., preferably 110~125° C., preferably 115~120° C.

There will be a plus or minus 3° C. temperature deviation between the actual synthesis temperature and the mentioned temperature.

Preferably, the diazotization reagent mentioned in step (a) is selected from nitrite, nitrosylsulfuric acid, nitrite ester; Preferably, the nitrite is selected from lithium nitrite, sodium nitrite, potassium nitrite, ammonium nitrite, magnesium nitrite, barium nitrite and calcium nitrite; Nitrite ester can be isoamyl nitrite, n-butyl nitrite.

Further, the concentration of diazotization reagent feed liquid is 10 wt %~95 wt %, preferably 20 wt %~40 wt %. The diazotization reagent feed liquid is selected from liquid diazotization reagents, slurry or pulp of diazotization reagents, diazotization reagent suspension, emulsion and solution.

Further, the reductant mentioned in step (b) is any one or any kinds of sulfite, bisulfite, thiosulfate, bisulfite, pyrosulfite, ammonia water; preferably, the mentioned sulfite is selected from lithium sulfite, sodium sulfite, potassium sulfite, ammonium sulfite; bisulfite is selected from lithium bisulfite, sodium bisulfite, potassium bisulfite and ammonium bisulfite; thiosulfate is selected from lithium thiosulfate, sodium thiosulfate, potassium thiosulfate and ammonium thiosulfate; dithionite is selected from lithium disulfite, sodium disulfite, potassium disulfite, ammonium disulfite; pyrosulfite is selected from lithium pyrosulfite, sodium pyrosulfite, potassium pyrosulfite, and ammonium pyrosulfite.

Further, the concentration of the mentioned reductant feed liquid is 10 wt %~75 wt %, preferably 15 wt~30 wt %. The mentioned reductant feed liquid is selected from liquid reductants, slurry or pulp of reductants, suspension, emulsion and solution of reductants.

Further, the mentioned acid is selected from hydrochloric acid, hydrobromic acid, sulfuric acid, phosphoric acid, nitric acid, oxalic acid; preferably, the concentration of hydrochloric acid is 10 wt %~37 wt %, hydrobromic acid is 10 wt %~47 wt %, sulfuric acid is 10 wt %~98 wt %, phosphoric acid is 10 wt %~98 wt %, nitric acid is 10 wt %~68 wt %, and oxalic acid is 10 wt %~40 wt %; preferably, the concentration of hydrochloric acid is 15 wt %~36 wt %.

Further, the temperature of the diazotization reaction is 2~80° C., preferably 5~65° C., preferably 10~55° C., preferably 15~45° C., preferably 20~35° C., preferably 25~33° C., preferably 28~30° C.

Further, the temperature of the reduction reaction 40~130° C., preferably 50~125° C., preferably 70~120° C. preferably 90~120° C., preferably 95~118° C., preferably 105~115° C., preferably 110~115° C.

Further, the temperature of acidic hydrolysis and salifying is 40~130° C., preferably 70~130° C. preferably 90~130° C., preferably 95~125° C., preferably 100~125° C., preferably 105~125° C., preferably 110~125° C., preferably 115~120° C.

Further, the molar ratio of aniline or substituted phenylamine to diazotization reagent is 1:0.9~1.2; preferably 1:1.01~1.05.

Further, the molar ratio of aniline or substituted phenylamine to reductant is 1:2.0~8.0, preferably 1:2.5~3.0.

Further, the molar ratio of aniline or substituted phenylamine to acid is 1:3.0~10.0, preferably 1:4.0~4.9.

Further, the materials of the reactor are metal, alloy, glass, silicon, ceramic, carbon fiber and polymer, etc.

It should be noted that the concentration of raw materials used in the actual synthesis (including laboratory, pilot test and actual production process) will have a deviation of 5 percentage points of the mass concentration; In practical synthesis temperature zones will have +/−5° C. temperature deviation; The channel length of the reactor module characteristic used in the actual synthesis will have a deviation of 0.5 m, and the channel diameter will have a deviation of 0.5 mm; The total reaction time in the actual synthesis will have a deviation of 15 s.

In this continuous flow process, under acidic conditions, aniline or substituted aniline reacts with diazotization reagent in the modularization temperature zone to generate diazonium salt rapidly, and then the diazonium salt is reduced by reductant, that is, diazonium salt is continuously produced and consumed, and large quantities of explosive diazonium salts are not retained during the process.

The second purpose of the invention is to provide an integrated reactor for continuous flow synthesis of different phenylhydrazine salts and substituted phenylhydrazine salts, wherein the mentioned integrated reactor adopts modular structure, and contains multiple temperature zones, each of which independently contains more than one reactor module or reactor module group. The reactor module group is composed of multiple reactor modules in series or in parallel, and each temperature zone is connected to each other.

Further, the number of the inlets of the integrated reactor is one or more, the number of the outlets of the integrated reactor is one or more.

Further, the temperature zones are connected in series or in parallel.

Further, the reactor modules, the reactor module groups, each reactor module and reactor module groups are connected in series or parallel to each other.

Further, the reactor module is any reactor that can realize continuous flow process; the mentioned reactor is any one or any kinds of micro-reactor, series coil reactor, tubular reactor. The said micro-reactor, also known as micro-structure reactor or micro-channel reactor, is a kind of equipment in which chemical reaction occurs in a limited area with a general lateral size of 1 mm or less, and the most typical than of such a limited area is the micro-size channel. A series coil reactor is a reactor composed of a coil reactor in series by means of a pipe, and a coil reactor is a reactor with coil pipes. Tubular reactor is a continuous operation reactor with tubular shape and large aspect ratio. This reactor can be very long; can be a single tube or multi-tube in parallel; can be empty or filled.

Further, each temperature zone may contain any one of the above reactors or a combination of any kinds of the above reactors.

Preferably, each temperature zone also further contains buffer vessel, which is a vessel with a certain volume, and is mainly used to buffer pressure fluctuations and balance flow differences of the system, making the system work more stable.

Further, channel length of the reactor module is 0.5~5 m.

Further, the channel diameter of the reactor shall be more than 0.5 mm, preferably the channel diameter of the reactor could be 0.5~1 mm, 1~3 mm, 3~5 mm, 5~6.35 mm, 6.35~12.7 mm, 12.7~25.4 mm, 25.4~55 mm.

Further, the material of the reactor can be metal, alloy, glass, silicon material, ceramic, carbon fiber, polymer, etc.

Preferably, the integrated reactor comprises four temperature zones.

Further, the temperature of the zones I is 2~80° C., preferably 5~65° C., preferably 10~55° C., preferably 15~45° C., preferably 20~35° C., preferably 25~33° C., preferably 28~30° C.

Further, the temperature of the zones II is 30~120° C., preferably 50~110° C., preferably 70~110° C., preferably 90~110° C., preferably 95~110° C., preferably 100~108° C., preferably 105~108° C.

Further, the temperature of the zones III is 40~130° C., preferably 50~125° C., preferably 70~120° C., preferably 90~120° C., preferably 95~118° C., preferably 105~115° C., preferably 110~115° C.

Further, the temperature of the zones IV is 40~130° C., preferably 70~130° C., preferably 90~130° C., preferably 95~125° C., preferably 100~125° C., preferably 105~125° C., preferably 110~125° C., preferably 115~120° C.

There will be a plus or minus 3° C. temperature deviation between the actual synthesis temperature and the mentioned temperature.

Compared with the prior art, the beneficial effects of the invention are as follows:

1. The invention innovatively breaks through the limitation of traditional technology and develops an integrated reactor with high integration to realize the whole-process continuous flow synthesis of substituted phenylhydrazine salts. That is, four reaction raw materials (acid liquid of aniline or substituted aniline, diazotization reagent, reductant and acid) are added to the reactor continuously, and the reaction products are collected continuously. Only one compact equipment is needed to solve the three-step reaction. At the same time, because the mass and heat transfer effect are greatly improved, there is no need to add dropwise slowly in this device, which greatly improves the process efficiency and solves the technical problem of whole process continuous production of phenylhydrazine salts and substituted phenylhydrazine salts.
2. The process of the invention realizes production of phenylhydrazine salts and substituted phenylhydrazine salts both on a large-scale and with high efficiency, high quality and high yield. The reaction time of the process is no more than 20 min, while that of existing process is at least several hours. The product made by the process does not contain by-products (for example, diazoamino compounds, reduction reaction intermediates, reduction reaction products). The process does not include additional purification steps. That is, in the reaction process and the treatment of the reaction products, there is no removal step for the by-products (for example, by organic solvents, such as toluene extraction, washing (such as pickling or washing), recrystallization etc.). The purity of the obtained product can be more than 99%, even can reach more than 99.9%. It saves the equipment, reagent and time comparing with the traditional purifying process.
3. The invention develops an integrated reactor with high integration and flexible applicability for the synthesis of different phenylhydrazine salts and substituted phenylhydrazine salts. By using the integrated reactor, only specific adjustment of process conditions and parameters is required, including division and temperature setting of each temperature zone, material concentration, ratio and flow rate, so as to make them play a coordinated role and match with the reaction procedure, and then the continuous flow process of corresponding phenylhydrazine salt and substituted phenylhydrazine salt can be realized. The same reactor can be used to efficiently produce phenylhydrazine salts with different types and sites of substituents on the benzene ring.
4. The temperature zones division of the integrated reactor and temperature settings of each temperature zone in this invention, combining with the excellent mass and heat transfer characteristics of the reactor module, realize the precise control of temperature, avoid the safety risk brought by the explosion caused by diazonium salt decomposition due to the sudden jump of local temperature, and greatly improve the safety of the device operation and production process. At the same time, the problem of solid blockage in the process of reduction reaction and acidic hydrolysis and salifying was solved, and the continuous flow process of three steps of diazotization, reduction and acidic hydrolysis and salifying was successfully realized.
5. As it is a continuous flow process, diazonium salt is continuously produced and consumed. In addition, the liquid-holding capacity of the continuous flow reactor is often very small. Generally, the liquid-holding capacity of the same annual production is only 1/1000 of that of the traditional reaction kettle. There is no explosive diazonium salt retained in the process, so the process safety is greatly improved. The liquid-holding capacity of the reactor refers to the total volume of materials stored in the reactor at any time when the operation reaches a steady state.
6. Compared with the traditional reaction kettle, the reactor has a smaller liquid-holding capacity, smaller device size and smaller occupation area, so the land cost and construction cost of the plant workshop are greatly saved.
7. Because continuous flow process has better production safety and process stability than traditional batch process, it can achieve larger production scale than batch process.

EXAMPLES

The following examples, illustrating the invention further, are not to be constructed as being limitations thereon. It will be appreciated that all kinds of improvements, modifications and alternatives based on the invention by person skilled in the art after reading the descriptions of the invention, which are all equivalents of the invention, do not depart from the broad inventive concept thereof. The examples selected here cover the comprehensive effect of two kinds of substituents or multiple different substituents on the benzene ring: electron-drawing effect and electron-donating effect. Electron-drawing group usually contains: halogen group, trifluoromethyl group (—$CF_3$), —$NO_2$, —CN, —COOH, —$SO_3H$, etc.; Electron-donating group usually contains: alkoxy, alkyl, —$NR^1R^2$, etc. The temperatures of the diazotization for different kinds of groups may be a little different, but are all within the limitation of the right belonging to the invention.

Concentrations are given by mass concentration, and purity of products are determined by high performance liquid chromatography (HPLC). The diazoamino compounds are not determined in the reaction process by HPLC, and the diazoamino compounds, reduction reaction intermediates and reduction reaction products are not determined in the outlet products by HPLC.

The structural formula of the diazoamino compounds is:

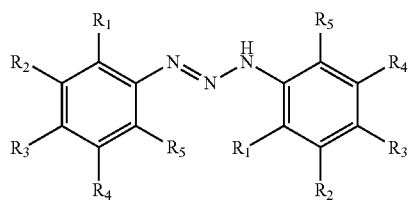

5

The mentioned structural formula of the reduction reaction intermediates anions are:

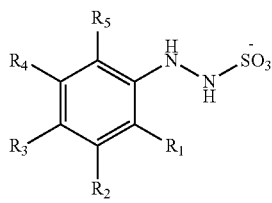

6

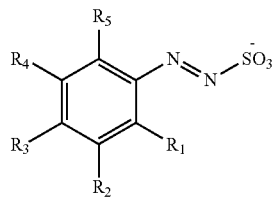

7

The mentioned structural formula of anions of the reduction reaction products are:

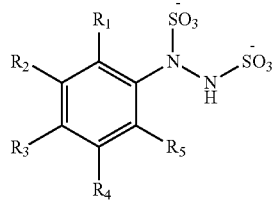

3

Where, the cations are selected from any metal cation or $NH_4^+$: R1, R2, R3, R4, R5 are independently selected from —H, —Cl, —Br, —CN, —$NO_2$, —$CF_3$, —$SO_3H$, —COOH, C1-C4 alkoxy groups, C1-C4 saturated or unsaturated alkyl; A is selected from HCl, HBr, $H_2SO_4$, $HNO_3$, $H_3PO_4$, HOOC—COOH (oxalic acid).

Examples 1~20

Figure 1:
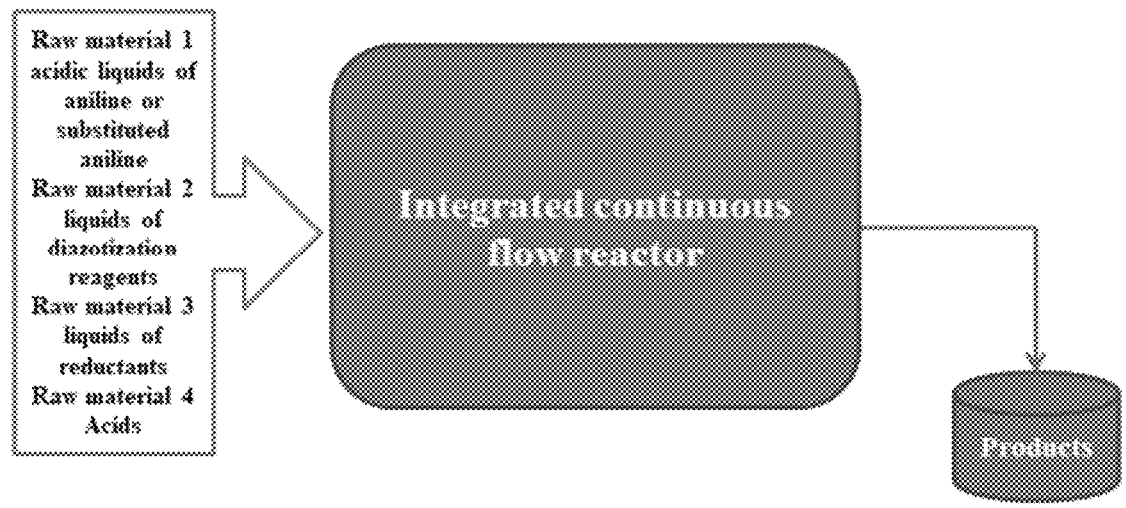
FIG. 1 provide an illustration of process diagram of continuous synthesis method in the invention.
Figure 2:
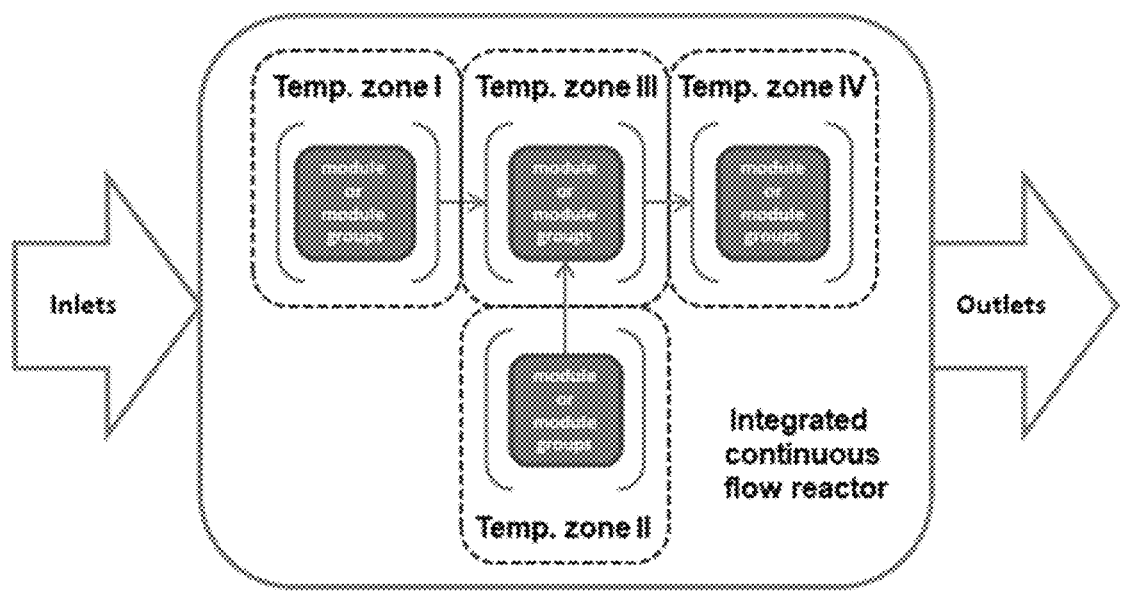
FIG. 2 is a schematic diagram of the integrated reactor described in the invention. Where T1 is the temperature of the temperature zone I; T2 is the temperature of the temperature zone II; T3 is the temperature of the temperature zone III; T4 is the temperature of the temperature zone IV.

As shown in FIG. 1, the raw material 1 (acidic liquids of aniline) and raw material 2 ($NaNO_2$ aqueous solution with mass concentration of 20%) were fed to temperature section 1 with constant-flow pump, and the diazotization of aniline completed while the materials flowed past the temperature section 1. The raw material 3 ($Na_2SO_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flow through temperature section 4. The reaction mixture was collected, crystallization by cooling the temperature, after filtration and drying to get the phenylhydrazine salts product. Reaction parameters and results were as follows:

TABLE 1

| | Raw material ratio*: | | | | |
|---|---|---|---|---|---|
| | Raw material flow rate** (g/min) | | | | Raw material molar ratio |
| Example | Raw material 1 (acidic liquids of aniline) | Raw material 2 (20% conc. aqueous solution of $NaNO_2$) | Raw material 3 (19% conc. aqueous solution of $Na_2SO_3$) | Raw material 4 | Raw material 1/ Raw materia l2/ Raw material 3/ Raw material 4 |
| 1 | 35.0 | 13.0 | 95.5 | 13.7 (37% HCl) | 1.0:1.04:3.5:4.0 |
| 2 | 35.0 | 13.0 | 95.6 | 131.8(10% $H_2SO_4$) | 1.0:1.04:3.5:4.0 |
| 3 | 35.0 | 13.0 | 95.6 | 142.6 (10% H3PO4) | 1.0:1.04:3.5:4.0 |
| 4 | 35.0 | 12.2 | 95.6 | 137.1 (10% oxalic acid) | 1.0:0.96:3.5:4.0 |

TABLE 1-continued

| | Raw material ratio*: | | | | |
|---|---|---|---|---|---|
| | Raw material flow rate** (g/min) | | | | |
| Example | Raw material 1 (acidic liquids of aniline) | Raw material 2 (20% conc. aqueous solution of NaNO$_2$) | Raw material 3 (19% conc. aqueous solution of Na$_2$SO$_3$) | Raw material 4 | Raw material molar ratio Raw material 1/ Raw materia l2/ Raw material 3/ Raw material 4 |
| 5 | 35.0 | 12.4 | 95.6 | 114.3 (10% HBr) | 1.0:0.98:3.5:4.0 |
| 6 | 35.0 | 13.0 | 95.6 | 91.6 (10% HNO3) | 1.0:1.04:3.5:4.0 |
| 7 | 35.0 | 13.0 | 95.6 | 15.3 (98% H3PO4) | 1.0:1.04:3.5:4.0 |
| 8 | 35.0 | 12.6 | 95.5 | 34.5 (40% oxalic acid) | 1.0:1.00:3.5:4.0 |
| 9 | 35.0 | 13.0 | 95.6 | 23.6 (47% HBr) | 1.0:1.04:3.5:4.0 |
| 10 | 35.0 | 13.0 | 95.6 | 14.6 (98% H$_2$SO$_4$) | 1.0:1.04:3.5:4.0 |
| 11 | 35.0 | 13.0 | 95.6 | 13.8 (68% HNO3) | 1.0:1.04:3.5:4.0 |
| 12 | 35.0 | 13.0 | 95.6 | 13.7 (37% HCl) | 1.0:1.05:3.5:4.0 |
| 13 | 35.0 | 13.0 | 95.6 | 13.7 (37% HCl) | 1.0:1.04:3.5:4.0 |
| 14 | 35.0 | 13.0 | 95.6 | 13.7 (37% HCl) | 1.0:1.04:3.5:4.0 |
| 15 | 35.0 | 13.0 | 95.6 | 13.7 (37% HCl) | 1.0:1.04:3.5:4.0 |
| 16 | 35.0 | 13.0 | 95.6 | 13.7 (37% HCl) | 1.0:1.04:3.5:4.0 |
| 17 | 35.0 | 13.0 | 95.6 | 13.7 (37% HCl) | 1.0:1.04:3.5:4.0 |
| 18 | 35.0 | 13.0 | 95.6 | 13.7 (37% HCl) | 1.0:1.04:3.5:4.0 |
| 19 | 35.0 | 13.0 | 95.5 | 13.7 (37% HCl) | 1.0:1.04:3.5:4.0 |
| 20 | 35.0 | 13.0 | 95.6 | 13.7 (37% HCl) | 1.0:1.04:3.5:4.0 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 2

| | Reaction temperature and results* | | | | | | | |
|---|---|---|---|---|---|---|---|---|
| Example | T1 (° C.) | T2 (° C.) | T3 (° C.) | T4 (° C.) | Reaction module features** | Total reaction time*** (min) | Purity (%) | Yield (%) |
| 1 | 20 | 90 | 120 | 130 | 0.5~1.5 m, 0.5~1.5 mm | 5.5 | 97.1 | 94.3 |
| 2 | 10 | 85 | 110 | 125 | 0.5~1.5 m, 0.5~1.5 mm | 16 | 97 | 95.1 |
| 3 | 5 | 80 | 105 | 120 | 0.5~1.5 m, 0.5~1.5 mm | 16.5 | 97.2 | 94 |
| 4 | 2 | 70 | 100 | 115 | 0.5~1.5 m, 0.5~1.5 mm | 20 | 96 | 94.4 |
| 5 | 5 | 88 | 90 | 110 | 0.5~1.5 m, 0.5~1.5 mm | 19 | 96.5 | 94.2 |
| 6 | 15 | 90 | 100 | 105 | 0.5~1.5 m, 0.5~1.5 mm | 17 | 96.2 | 94.6 |
| 7 | 30 | 90 | 95 | 100 | 0.5~1.5 m, 0.5~1.5 mm | 2.5 | 98 | 96.5 |
| 8 | 28 | 85 | 105 | 95 | 0.5~1.5 m, 0.5~1.5 mm | 4.5 | 97.4 | 95.2 |
| 9 | 25 | 100 | 105 | 90 | 0.5~1.5 m, 0.5~1.5 mm | 3.5 | 97.6 | 95 |
| 10 | 35 | 110 | 120 | 130 | 0.5~1.5 m, 0.5~1.5 mm | 2 | 97.9 | 95.9 |
| 11 | 30 | 120 | 130 | 130 | 0.5~1.5 m, 0.5~1.5 mm | 6 | 97.7 | 95.7 |
| 12 | 40 | 30 | 40 | 40 | 0.5~1.5 m, 0.5~1.5 mm | 20 | 96.1 | 96.1 |
| 13 | 45 | 40 | 50 | 50 | 0.5~1.5 m, 0.5~1.5 mm | 19.5 | 95.7 | 96.7 |
| 14 | 50 | 50 | 60 | 60 | 0.5~1.5 m, 0.5~1.5 mm | 19 | 95.6 | 95.3 |
| 15 | 55 | 60 | 70 | 70 | 0.5~1.5 m, 0.5~1.5 mm | 18.5 | 95.2 | 99.1 |
| 16 | 60 | 70 | 80 | 80 | 0.5~1.5 m, 0.5~1.5 mm | 18 | 95.4 | 97.1 |
| 17 | 65 | 80 | 90 | 90 | 0.5~1.5 m, 0.5~1.5 mm | 17.5 | 98.2 | 97.2 |
| 18 | 70 | 90 | 100 | 110 | 0.5~1.5 m, 0.5~1.5 mm | 15 | 98.5 | 98.1 |
| 19 | 75 | 100 | 110 | 120 | 0.5~1.5 m, 0.5~1.5 mm | 4 | 95.8 | 98.2 |
| 20 | 80 | 110 | 175 | 130 | 0.5~1.5 m, 0.5~1.5 mm | 3 | 98.8 | 98.8 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Examples 21-31

As shown in FIG. 1, the raw material 1 (acidic liquids of 2-fluoroaniline) and raw material 2 (NaNO$_2$ aqueous solution with mass concentration of 20%) were fed to temperature section 1 with constant-flow pump, and the diazotization of aniline completed while the materials flowed past the temperature section 1. The raw material 3 (Na$_2$SO$_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the (2-fluorophenyl)hydrazine salts product. Reaction parameters and results were as follows:

TABLE 3

Raw material ratio*

Raw material flow rate** (g/min)

| Example | Raw material1 (acidic liquids of 2-fluoroaniline) | Raw material2 (20% conc. aqueous solution of NaNO$_2$) | Raw material3 (19% conc. aqueous solution of Na$_2$SO$_3$) | Raw material4 | Raw material molar ratio Raw material1/Raw material2/Raw material3/Raw material4 |
|---|---|---|---|---|---|
| 21 | 35.0 | 13.0 | 95.6 | 13.7 (37% HCl) | 1.0:1.04:3.5:4.0 |
| 22 | 35.0 | 13.0 | 95.6 | 131.8 (10% H2SO4) | 1.0:1.04:3.5:4.0 |
| 23 | 35.0 | 13.0 | 95.6 | 142.6 (10% H3PO4) | 1.0:1.04:3.5:4.0 |
| 24 | 35.0 | 13.0 | 95.6 | 137.1 (10% oxalic acid) | 1.0:0.90:3.5:4.0 |
| 25 | 35.0 | 12.8 | 95.6 | 114.3 (10% HBr) | 1.0:0.95:3.5:4.0 |
| 26 | 35.0 | 13.0 | 95.6 | 91.6 (10% HNO3) | 1.0:1.04:3.5:4.0 |
| 27 | 35.0 | 13.0 | 95.6 | 15.3 (98% H3PO4) | 1.0:1.04:3.5:4.0 |
| 28 | 35.0 | 12.6 | 95.6 | 34.5 (40% oxalic acid) | 1.0:1.00:3.5:4.0 |
| 29 | 35.0 | 13.0 | 95.6 | 23.6 (47% HBr) | 1.0:1.04:3.5:4.0 |
| 30 | 35.0 | 13.0 | 95.6 | 14.6 (98% H2SO4) | 1.0:1.04:3.5:4.0 |
| 31 | 35.0 | 13.0 | 95.6 | 13.8 (68% HNO3) | 1.0:1.04:3.5:4.0 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 4

Reaction temperature and results*

| Example | T1 (° C.) | T2 (° C.) | T3 (° C.) | T4 (° C.) | Reaction module features | Total reaction time*** (min) | Purity (%) | Yield (%) |
|---|---|---|---|---|---|---|---|---|
| 21 | 20 | 90 | 120 | 130 | 0.5~1.5 m, 0.5~1.5 mm | 4 | 97.1 | 95.1 |
| 22 | 10 | 85 | 110 | 125 | 0.5~1.5 m, 0.5~1.5 mm | 16 | 99.5 | 95.1 |
| 23 | 5 | 80 | 105 | 120 | 0.5~1.5 m, 0.5~1.5 mm | 16.5 | 99 | 96.5 |
| 24 | 2 | 70 | 100 | 115 | 0.5~1.5 m, 0.5~1.5 mm | 20 | 96 | 96 |
| 25 | 5 | 88 | 90 | 110 | 0.5~1.5 m, 0.5~1.5 mm | 19 | 96.5 | 94.2 |
| 26 | 15 | 90 | 100 | 105 | 0.5~1.5 m, 0.5~1.5 mm | 17 | 96.2 | 95.7 |
| 27 | 30 | 90 | 95 | 100 | 0.5~1.5 m, 0.5~1.5 mm | 2.5 | 98.7 | 96.5 |
| 28 | 28 | 85 | 105 | 95 | 0.5~1.5 m, 0.5~1.5 mm | 4.5 | 98.9 | 95.2 |
| 29 | 24 | 100 | 105 | 90 | 0.5~1.5 m, 0.5~1.5 mm | 3.5 | 97 | 95.8 |
| 30 | 35 | 110 | 120 | 130 | 0.5~1.5 m, 0.5~1.5 mm | 2 | 99.9 | 95.9 |
| 31 | 30 | 120 | 130 | 130 | 0.5~1.5 m, 0.5~1.5 mm | 3 | 97.7 | 95.7 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 32-42

As shown in FIG. 1, the raw material 1 (acidic liquids of p-toluidine) arid raw material 2 (NaNO$_2$ aqueous solution with mass concentration of 20%) were fed to temperature section 1 with constant-flow pump, and the diazotization of aniline completed while the materials flowed past the temperature section 1. The raw material 3 (NH$_4$HSO$_3$ aqueous solution with mass concentration of 20%) was fed to temperature section 2 with constant-flow pump far preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the (4-methylphenyl)hydrazine salts product. Reaction parameters and results were as follows:

TABLE 5

Raw material ratio*:

Raw material flow rate** (g/min)

| Example | Raw material1 (acidic liquids of p-toluidine) | Raw material2 (20% conc. aqueous solution of NaNO$_2$) | Raw material3 (20% conc. aqueous solution of NH$_4$HSO$_3$) | Raw material4 | Raw material molar ratio Raw material1/Raw material2/Raw material3/Raw material4 |
|---|---|---|---|---|---|
| 32 | 35.0 | 13.0 | 83.5 | 13.7 (37% HCl) | 1.0:1.04:3.5:4.0 |
| 33 | 35.0 | 12.8 | 83.5 | 131.8 (10% H2SO4) | 1.0:1.02:3.5:4.0 |
| 34 | 35.0 | 12.6 | 83.5 | 142.6 (10% H3PO4) | 1.0:1.00:3.5:4.0 |

TABLE 5-continued

Raw material ratio*:

Raw material flow rate** (g/min)

| Example | Raw material1 (acidic liquids of p-toluidine) | Raw material2 (20% conc. aqueous solution of NaNO$_2$) | Raw material3 (20% conc. aqueous solution of NH$_4$HSO$_3$) | Raw material4 | Raw material molar ratio Raw material1/Raw material2/Raw material3/Raw material4 |
|---|---|---|---|---|---|
| 35 | 35.0 | 12.6 | 83.5 | 137.1 (10% oxalic acid) | 1.0:1.00:3.5:4.0 |
| 36 | 35.0 | 12.8 | 83.5 | 114.3 (10% HBr) | 1.0:1.02:3.5:4.0 |
| 37 | 35.0 | 13.0 | 83.5 | 91.6 (10% HNO3) | 1.0:1.04:3.5:4.0 |
| 38 | 35.0 | 13.0 | 83.5 | 15.3 (98% H3PO4) | 1.0:1.04:3.5:4.0 |
| 39 | 35.0 | 13.0 | 83.5 | 34.5 (40% oxalic acid) | 1.0:1.04:3.5:4.0 |
| 40 | 35.0 | 13.0 | 83.5 | 23.6 (47% HBr) | 1.0:1.04:3.5:4.0 |
| 41 | 35.0 | 13.0 | 83.5 | 14.6 (98% H2SO4) | 1.0:1.04:3.5:4.0 |
| 42 | 35.0 | 13.0 | 83.5 | 13.8 (68% HNO3) | 1.0:1.04:3.5:4.0 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 6

Reaction temperature and results*

| Example | T1 (° C.) | T2 (° C.) | T3 (° C.) | T4 (° C.) | Reaction module features | Total reaction time*** (min) | Purity (%) | Yield (%) |
|---|---|---|---|---|---|---|---|---|
| 32 | 20 | 105 | 115 | 130 | 0.5~1.5 m, 0.5~1.5 mm | 5 | 97.6 | 95.4 |
| 33 | 10 | 95 | 100 | 130 | 0.5~1.5 m, 0.5~1.5 mm | 16 | 96 | 94.8 |
| 34 | 12 | 40 | 90 | 130 | 0.5~1.5 m, 0.5~1.5 mm | 16.5 | 97 | 94.5 |
| 35 | 5 | 100 | 120 | 130 | 0.5~1.5 m, 0.5~1.5 mm | 20 | 97 | 94 |
| 36 | 5 | 107 | 40 | 130 | 0.5~1.5 m, 0.5~1.5 mm | 19 | 96.8 | 94.7 |
| 37 | 10 | 80 | 50 | 130 | 0.5~1.5 m, 0.5~1.5 mm | 17 | 96.7 | 96.3 |
| 38 | 30 | 110 | 110 | 130 | 0.5~1.5 m, 0.5~1.5 mm | 2.5 | 98.5 | 96.8 |
| 39 | 30 | 30 | 50 | 130 | 0.5~1.5 m, 0.5~1.5 mm | 5.5 | 97.3 | 95.5 |
| 40 | 30 | 85 | 70 | 130 | 0.5~1.5 m, 0.5~1.5 mm | 3.5 | 98 | 96.9 |
| 41 | 35 | 90 | 95 | 130 | 0.5~1.5 m, 0.5~1.5 mm | 2 | 97.1 | 95.2 |
| 42 | 28 | 105 | 80 | 130 | 0.5~1.5 m, 0.5~1.5 mm | 4 | 97.9 | 95.3 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 43-53

As shown in FIG. 1, the raw material 1 (acidic liquids of 2,4-dimethoxyaniline) and raw material 2 (Mg(NO$_2$)$_2$ aqueous solution with mass concentration of 10%) were fed to temperature section 1 with constant-flow pump, and the diazotization of aniline completed while the materials flowed past the temperature section 1. The raw material 3 (Na$_2$SO$_3$/NaHSO$_3$ aqueous solution with mass concentration of 20%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the (2,4-dimethoxyphenyl) hydrazine salts product. Reaction parameters and results were as follows:

TABLE 7

Raw material ratio*:

Raw material flow rate** (g/min)

| Example | Raw material1 ((acidic liquids of 2,4-dimethoxyaniline) | Raw material2 (10% conc. aqueous solution of Mg(NO$_2$)$_2$) | Raw material3 (20% conc. aqueous solution of Na$_2$SO$_3$/NaHSO$_3$) | Raw material4 | Raw material molar ratio Raw material1/Raw material2/Raw material3/Raw material4 |
|---|---|---|---|---|---|
| 43 | 35.0 | 88.8 | 110 | 13.7 (37% HCl) | 1.0:1.04:3.5:4.0 |
| 44 | 35.0 | 88.8 | 110 | 131.8 (10% H2SO4) | 1.0:1.04:3.5:4.0 |

TABLE 7-continued

| | Raw material ratio*: | | | | |
|---|---|---|---|---|---|
| | Raw material flow rate** (g/min) | | | | |
| Example | Raw material1 ((acidic liquids of 2,4-dimeth-oxyaniline) | Raw material2 (10% conc. aqueous solution of Mg(NO$_2$)$_2$) | Raw material3 (20% conc. aqueous solution of Na$_2$SO$_3$/ NaHSO$_3$) | Raw material4 | Raw material molar ratio Raw material1/Raw material2/Raw material3/Raw material4 |
| 45 | 35.0 | 88.8 | 110 | 142.6 (10% H3PO4) | 1.0:1.04:3.5:4.0 |
| 46 | 35.0 | 88.8 | 110 | 137.1 (10% oxalic acid) | 1.0:1.04:3.5:4.0 |
| 47 | 35.0 | 88.8 | 110 | 114.3 (10% HBr) | 1.0:1.04:3.5:4.0 |
| 48 | 35.0 | 88.8 | 110 | 91.6 (10% HNO3) | 1.0:1.04:3.5:4.0 |
| 49 | 35.0 | 88.8 | 110 | 15.3 (98% H3PO4) | 1.0:1.04:3.5:4.0 |
| 50 | 35.0 | 88.8 | 110 | 34.5 (40% oxalic acid) | 1.0:1.00:3.5:4.0 |
| 51 | 35.0 | 88.8 | 110 | 23.6 (47% HBr) | 1.0:1.04:3.5:4.0 |
| 52 | 35.0 | 88.8 | 110 | 14.6 (98% H2SO4) | 1.0:1.04:3.5:4.0 |
| 53 | 35.0 | 88.8 | 110 | 13.8 (68% HNO3) | 1.0:1.04:3.5:4.0 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 8

| | Reaction temperature and results* | | | | | | | |
|---|---|---|---|---|---|---|---|---|
| Example | T1 (° C.) | T2 (° C.) | T3 (° C.) | T4 (° C.) | Reaction module features | Total reaction time*** (min) | Purity (%) | Yield (%) |
| 43 | 20 | 90 | 85 | 115 | 0.5~1.5 m, 0.5~1.5 mm | 4.5 | 97.6 | 95.4 |
| 44 | 10 | 90 | 95 | 110 | 0.5~1.5 m, 0.5~1.5 mm | 16 | 96.6 | 94.8 |
| 45 | 12 | 90 | 105 | 100 | 0.5~1.5 m, 0.5~1.5 mm | 16.5 | 98.6 | 94.5 |
| 46 | 5 | 90 | 85 | 120 | 0.5~1.5 m, 0.5~1.5 mm | 20 | 98.4 | 94 |
| 47 | 5 | 90 | 105 | 50 | 0.5~1.5 m, 0.5~1.5 mm | 19 | 96.8 | 94.7 |
| 48 | 10 | 90 | 105 | 70 | 0.5~1.5 m, 0.5~1.5 mm | 17 | 96.7 | 97 |
| 49 | 30 | 90 | 120 | 125 | 0.5~1.5 m, 0.5~1.5 mm | 2.5 | 98.5 | 96.8 |
| 50 | 30 | 90 | 115 | 40 | 0.5~1.5 m, 0.5~1.5 mm | 4.5 | 97.3 | 95.5 |
| 51 | 30 | 90 | 100 | 60 | 0.5~1.5 m, 0.5~1.5 mm | 3.5 | 98 | 96 |
| 52 | 35 | 90 | 90 | 105 | 0.5~1.5 m, 0.5~1.5 mm | 2 | 97.1 | 99.5 |
| 53 | 28 | 90 | 120 | 95 | 0.5~1.5 m, 0.5~1.5 mm | 3 | 97.9 | 95.2 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 54-55

As shown in FIG. 1, the raw material 1 (acidic liquids of 4-bromoaniline) and raw material 2 (liquids of nitrosylsulfuric acid with mass concentration of 15%) were fed to temperature section 1 with constant-flow pump, and the diazotization of aniline completed while the materials flowed past the temperature section 1. The raw material 3 (Na$_2$S$_2$O$_4$ aqueous solution with mass concentration of 20%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the (4-bromophenyl)hydrazine salts product. Reaction parameters and results were as follows:

TABLE 9

| | Raw material ratio*: | | | | |
|---|---|---|---|---|---|
| | Raw material flow rate** (g/min) | | | | |
| Example | Raw material1 (acidic liquids of 4-bromoaniline) | Raw material2 (liquids of nitrosylsulfuric acid with mass concentration of 15%) | Raw material3 (Na$_2$S$_2$O$_4$ aqueous solution with mass concentration of 20%) | Raw material4 | Raw material molar ratio Raw material1/Raw material2/Raw material3/Raw material4 |
| 54 | 44 | 50.8 | 165.3 | 29.4 (36% H2SO4) | 1:1.04:3.2:4.9 |
| 55 | 44 | 50.8 | 165.3 | 15.8 (36% HCl) | 1:1.04:3.2:4.3 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 10

| | Reaction temperature and results* | | | | | | | |
|---|---|---|---|---|---|---|---|---|
| Example | T1 (° C.) | T2 (° C.) | T3 (° C.) | T4 (° C.) | Reaction module features** | Total reaction time*** (min) | Purity (%) | Yield (%) |
| 54 | 30 | 80 | 110 | 120 | 0.5~1.5 m, 0.5~1.5 mm | 7 | 97 | 95 |
| 55 | 30 | 80 | 120 | 130 | 0.5~1.5 m, 0.5~1.5 mm | 7 | 98 | 96 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 56-57

As shown in FIG. 1, the raw material 1 (acidic liquids of 4-bromo-2-fluoroaniline) and raw material 2 (15% conc. liquids of isoamyl nitrite) were fed to temperature section 1 with constant-flow pump, and the diazotization of aniline completed while the materials flowed past the temperature section 1. The raw material 3 (K$_2$S$_2$O$_3$ aqueous solution with mass concentration of 20%) was fed to temperature section 2 with constant-flow pump far preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the (4-bromo-2-fluorophenyl)hydrazine salts product. Reaction parameters and results were as follows:

TABLE 11

| | Raw material ratio*: | | | | |
|---|---|---|---|---|---|
| | Raw material flow rate** (g/min) | | | | |
| Example | Raw material1 (acidic liquids of 4-bromo-2-fluoroaniline) | Raw material2 (15% conc. liquids of isoamyl nitrite) | Raw material3 (K$_2$S$_2$O$_3$ aqueous solution with mass concentration of 20%) | Raw material4 (acid) | Raw material molar ratio Raw material1/Raw material2/Raw material3/Raw material4 |
| 56 | 46 | 46.8 | 199.5 | 17.26 (36% HCl) | 1:1.04:3.78:4.6 |
| 57 | 46 | 46.8 | 199.5 | 35.48 (30% oxalic acid) | 1:1.08:3.78:6.26 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 12

Reaction temperature and results*

| Example | T1 (° C.) | T2 (° C.) | T3 (° C.) | T4 (° C.) | Reaction module features** | Total reaction time*** (min) | Purity (%) | Yield (%) |
|---|---|---|---|---|---|---|---|---|
| 56 | 30 | 100 | 120 | 130 | 0.5~1.5 m, 0.5~1.5 mm | 6.5 | 98 | 95 |
| 57 | 30 | 100 | 120 | 130 | 0.5~1.5 m, 0.5~1.5 mm | 7.5 | 99 | 98 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 58-59

As shown in FIG. 1, the raw material 1 (acidic liquids of 2-aminobenzoic acid) and raw material 2 (20% conc. aqueous solution of $NaNO_2$) were fed to temperature section 1 with constant-flow pump, and the diazotization of aniline completed while the materials flowed past the temperature section 1. The raw material 3 ($Na_2SO_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected crystallization by cooling the temperature, after filtration and drying to get the 2-hydrazinobenzoic acid salts product. Reaction parameters and results were as follows:

Example 60-61

As shown in FIG. 1, the raw material 1 (acidic liquids of 3-aminobenzoic acid) and raw material 2 (20% conc. aqueous solution of $NaNO_2$) were fed to temperature section 1 with constant-flow pump, and the diazotization of aniline completed while the materials flowed past the temperature section 1. The raw material 3 ($Na_2SO_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the 3-hydrazinobenzoic acid salts product. Reaction parameters and results were as follows:

TABLE 13

Raw material ratio*:

| | Raw material flow rate** (g/min) | | | | Raw materialmolar ratio Raw material1/Raw material2/Raw material3/Raw material4 |
|---|---|---|---|---|---|
| Example | Raw material1 (acidic liquids of 2-aminobenzoic acid) | Raw material2 (20% conc. aqueous solution of $NaNO_2$) | Raw material3 ($Na_2SO_3$ aqueous solution with mass concentration of 19%) | Raw material4 | |
| 58 | 40 | 17.6 | 127.9 | 22.8 (36% HCl) | 1:1.04:3.78:4.6 |
| 59 | 40 | 17.6 | 127.9 | 76.6 (30% H2SO4) | 1:1.04:3.78:4.6 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 14

Reaction temperature and results*

| Example | T1 (° C.) | T2 (° C.) | T3 (° C.) | T4 (° C.) | Reaction module features** | Total reaction time*** (min) | Purity (%) | Yield (%) |
|---|---|---|---|---|---|---|---|---|
| 58 | 30 | 100 | 120 | 130 | 0.5~1.5 m, 0.5~1.5 mm | 8 | 98 | 95 |
| 59 | 30 | 100 | 120 | 130 | 0.5~1.5 m, 0.5~1.5 mm | 8.5 | 99 | 99.1 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

TABLE 15

Raw material ratio*:

| | Raw material flow rate** (g/min) | | | | Raw material molar ratio |
|---|---|---|---|---|---|
| Example | Raw material1 (acidic liquids of 3-aminobenzoic acid) | Raw material2 (20% conc. aqueous solution of NaNO$_2$) | Raw material3 (Na$_2$SO$_3$ aqueous solution with mass concentration of 19%) | Raw material4 | Raw material1/Raw material2/Raw material3/Raw material4 |
| 60 | 40 | 17.6 | 127.9 | 22.8 (36% HCl) | 1:1.04:3.78:4.6 |
| 61 | 40 | 17.6 | 127.9 | 76.6 (30% H2SO4) | 1:1.04:3.78:4.6 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 16

Reaction temperature and results*

| Example | T1 (° C.) | T2 (° C.) | T3 (° C.) | T4 (° C.) | Reaction module features** | Total reaction time*** (min) | Purity (%) | Yield (%) |
|---|---|---|---|---|---|---|---|---|
| 60 | 30 | 90 | 110 | 120 | 0.5~1.5 m, 0.5~1.5 mm | 9 | 97 | 94 |
| 61 | 30 | 100 | 120 | 125 | 0.5~1.5 m, 0.5~1.5 mm | 9.5 | 96 | 98.2 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 62-63

As shown in FIG. 1, the raw material 1 (acidic liquids of 2-aminobenzenesulfonic acid) and raw material 2 (20% conc. aqueous solution of NaNO$_2$) were fed to temperature section 1 with constant-flow pump, and the diazotization of aniline completed while the materials flowed past the temperature section 1. The raw material 3 (Na$_2$SO$_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected crystallization by cooling the temperature, after filtration and drying to get the 2-hydrazinobenzenesulfonic acid salts product. Reaction parameters and results were as follows:

TABLE 17

Raw material ratio*:

| | Raw material flow rate** (g/min) | | | | Raw material molar ratio |
|---|---|---|---|---|---|
| Example | Raw material1 ((acidic liquids of 2-aminobenzenesulfonic acid) | Raw material2 (20% conc. aqueous solution of NaNO$_2$) | Raw material3 (Na$_2$SO$_3$ aqueous solution with mass concentration of 19%) | Raw material4 | Raw material1/Raw material2/Raw material3/Raw material4 |
| 62 | 60 | 32.6 | 187.9 | 44.1 (36% HCl) | 1:1.04:3.0:4.6 |
| 63 | 60 | 32.6 | 187.9 | 141 (30% H2SO4) | 1:1.04:3.0:4.6 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 18

Reaction temperature and results*

| Example | T1 (° C.) | T2 (° C.) | T3 (° C.) | T4 (° C.) | Reaction module features** | Total reaction time*** (min) | Purity (%) | Yield (%) |
|---|---|---|---|---|---|---|---|---|
| 62 | 30 | 95 | 110 | 120 | 0.5~1.5 m, 0.5~1.5 mm | 10 | 97 | 99.1 |
| 63 | 30 | 100 | 120 | 130 | 0.5~1.5 m, 0.5~1.5 mm | 10.5 | 98 | 99.2 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 64-65

As shown in FIG. 1, the raw material 1 (acidic liquids of 3-aminobenzenesulfonic acid) and raw material 2 (20% conc. aqueous solution of NaNO$_2$) were fed to temperature section 1 with constant-flow pump, and the diazotization of aniline completed while the materials flowed past the temperature section 1. The raw material 3 (Na$_2$SO$_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the 3-hydrazinobenzenesulfonic acid salts product. Reaction parameters and results were as follows:

Example 66-67

As shown in FIG. 1, the raw material 1 (acidic liquids of 3-aminobenzenesulfonic acid) and raw material 2 (20% conc. aqueous solution of NaNO$_2$) were fed to temperature section 1 with constant-flow pump, and the diazotization of aniline completed while the materials flowed past the temperature section 1. The raw material 3 (Na$_2$SO$_3$ aqueous solution with mass concentration of 19%) was fed to temperature section 2 with constant-flow pump for preheating, then mixed with diazonium salt formed through temperature section 1 in temperature section 3, flowed through temperature section 3 until the reaction was completed. The reaction solution from temperature section 3 flowed into temperature section 4 after mixed with raw material 4 (acid), and the reaction completed while flowing through temperature section 4. The reaction mixture was collected, crystallization by cooling the temperature, after filtration and drying to get the hydrazinobenzenesulfonic acid salts product. Reaction parameters and results were as follows:

TABLE 19

Raw material ratio*:

| | Raw material flow rate** (g/min) | | | | |
|---|---|---|---|---|---|
| Example | Raw material1 (acidic liquids of 3-aminobenzene-sulfonic acid) | Raw material2 (20% conc. aqueous solution of NaNO$_2$) | Raw material3 (Na$_2$SO$_3$ aqueous solution with mass concentration of 19%) | Raw material4 | Raw material molar ratio Raw material1/Raw material2/Raw material3/Raw material4 |
| 64 | 60 | 32.6 | 187.9 | 44.1 (36% HCl) | 1:1.04:3.0:4.6 |
| 65 | 60 | 32.6 | 187.9 | 141 (30% H2SO4) | 1:1.04:3.0:4.6 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 20

Reaction temperature and results*

| Example | T1 (° C.) | T2 (° C.) | T3 (° C.) | T4 (° C.) | Reaction module features** | Total reaction time*** (min) | Purity (%) | Yield (%) |
|---|---|---|---|---|---|---|---|---|
| 64 | 30 | 90 | 110 | 120 | 0.5~1.5 m, 0.5~1.5 mm | 11 | 97 | 94.9 |
| 65 | 30 | 100 | 120 | 125 | 0.5~1.5 m, 0.5~1.5 mm | 11.5 | 96 | 95.2 |

*The temperature in the actual synthesis temperature section will vary by ±3° C. from the temperature listed in the table
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

TABLE 21

Raw material ratio*:

Raw material flow rate** (g/min)

| Example | Raw material1 (acidic liquids of 3-aminobenzene-sulfonic acid) | Raw material2 (20% conc. aqueous solution of NaNO$_2$) | Raw material3 (Na$_2$SO$_3$ aqueous solution with mass concentration of 19%) | Raw material4 | Raw material molar ratio Raw material1/Raw material2/Raw material3/Raw material4 |
|---|---|---|---|---|---|
| 66 | 60 | 32.6 | 187.9 | 44.1 (36% HCl) | 1:1.04:3.0:4.6 |
| 67 | 60 | 32.6 | 187.9 | 141 (30% H2SO4) | 1:1.04:3.0:4.6 |

*The concentration of the raw materials used in the actual synthesis will have a deviation of ±5 percentage point from the concentration listed in the table.
**The flow rate of the raw materials used in the actual synthesis will vary by ±2% from the flow rates listed in the table.

TABLE 22

Reaction temperature and results*

| Example | T1 (° C.) | T2 (° C.) | T3 (° C.) | T4 (° C.) | Reaction module features** | Total reaction time*** (min) | Purity (%) | Yield (%) |
|---|---|---|---|---|---|---|---|---|
| 66 | 30 | 90 | 110 | 120 | 0.5~1.5 m, 0.5~1.5 mm | 12 | 97 | 95.6 |
| 67 | 30 | 100 | 120 | 125 | 0.5~1.5 m, 0.5~1.5 mm | 12.5 | 96 | 96.6 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

Example 68-95

With procedures of Example 1~5, yields of substituted phenylhydrazine salts under different reaction conditions were investigated, the condition parameters and results are in the following table 23, 24 and 25. In the table, raw material 1 were acidic liquids of substituted aniline, raw material 2 were liquids of diazotization reagents, raw material 3 were liquids of reductants, and raw material 4 is HCl.

TABLE 23

Example 68-95 Raw material ratio*:

| Example | Raw material 1 | Raw material 2 | Raw material 2 concentration | Raw material 3 | Raw material 3 concentration | Raw material 4 concentration |
|---|---|---|---|---|---|---|
| 68 | 4-aminobenzoic acid | Mg(NO$_2$)$_2$ | 10% | Na$_2$SO$_3$ | 25% | 35% |
| 69 | 4-aminobenzenesulfonic acid | KNO$_2$ | 80% | K$_2$S$_2$O$_5$ | 23% | 25% |
| 70 | 4-aminobenzonitrile | NaNO$_2$ | 30% | NH$_4$HSO$_3$ | 75% | 32% |
| 71 | 4-nitroaniline | LiNO$_2$ | 45% | Li$_2$SO$_3$ | 30% | 30% |
| 72 | 3-nitroaniline | Ba(NO$_2$)$_2$ | 70% | Na$_2$S$_2$O$_4$ | 17% | 20% |
| 73 | 2-nitroaniline | Ca(NO$_2$)$_2$ | 35% | (NH$_4$)$_2$S$_2$O$_5$ | 65% | 35% |
| 74 | 2-methoxyaniline | NaNO$_2$ | 28% | Na$_2$SO$_3$/NaHSO$_3$ | 19% | 32% |
| 75 | 3-methoxyaniline | isoamyl nitrite | 95% | NH$_4$HSO$_3$/NH$_3$H$_2$O | 45% | 33% |
| 76 | 4-methoxyaniline | KNO$_2$ | 55% | K$_2$S$_2$O$_3$ | 55% | 26% |
| 77 | 2,4-difluoroaniline | nitrosylsulfuric acid | 15% | Na$_2$S$_2$O$_5$ | 35% | 29% |
| 78 | 4-(trifluoromethy)aniline | Mg(NO$_2$)$_2$ | 40% | K$_2$SO$_3$/K$_2$S$_2$O$_4$ | 10% | 35% |
| 79 | 4-chloro-2-fluoroaniline | Ba(NO$_2$)$_2$ | 65% | KHSO$_3$ | 20% | 15% |
| 80 | 2,4,6-trifluoroaniline | NaNO$_2$ | 33.5% | NH$_4$HSO$_3$/(NH$_4$)$_2$SO$_3$ | 50% | 20% |
| 81 | 2,4-dichloroaniline | n-butyl nitrite | 94% | K$_2$S$_2$O$_4$ | 40% | 30% |
| 82 | 2-chloroaniline | Mg(NO$_2$)$_2$ | 12% | Li$_2$S$_2$O$_4$ | 52% | 20% |
| 83 | 4-amino-3-fluorobenzonitrile | KNO$_2$ | 75% | Li$_2$S$_2$O$_5$ | 48% | 25% |
| 84 | 4-ethoxyaniline | NaNO$_2$ | 22% | (NH$_4$)$_2$SO$_3$ | 67% | 32% |
| 85 | 4-propoxyaniline | LiNO$_2$ | 60% | K$_2$SO$_3$ | 38% | 32% |
| 86 | 4-butoxyaniline | Ba(NO$_2$)$_2$ | 32% | NaHSO$_3$ | 29% | 32% |
| 87 | 2-ethylaniline | Ca(NO$_2$)$_2$ | 24% | LiHSO$_3$ | 32% | 32% |

TABLE 23-continued

Example 68-95 Raw material ratio*:

| Example | Raw material 1 | Raw material 2 | Raw material 2 concentration | Raw material 3 | Raw material 3 concentration | Raw material 4 concentration |
|---|---|---|---|---|---|---|
| 88 | 3-isopropylaniline | $NH_4NO_2$ | 32% | $(NH_4)_2S_2O_4$ | 62% | 32% |
| 89 | 4-butylaniline | isomayl nitrite | 88% | $Na_2S_2O_3$ | 28% | 37% |
| 90 | 4-vinylaniline | n-butyl nitrite | 85% | $Li_2S_2O_3$ | 43% | 32% |
| 91 | 4-allylaniline | nitrosylsulfuric acid | 17% | $(NH_4)_2S_2O_3$ | 72% | 32% |
| 92 | 4-(but-3-en-1-yl)aniline | $NaNO_2$ | 37% | $(NH_4)_2SO_3/(NH_4)_2S_2O_3$ | 57% | 32% |
| 93 | 2,3,4-trifluoroaniline | $Mg(NO_2)_2$ | 10% | $Na_2SO_3$ | 25% | 32% |
| 94 | 2,3,4,5-tetrafluoroaniline | $KNO_2$ | 80% | $K_2S_2O_5$ | 23% | 32% |
| 95 | 2,3,4,5-tetrachloroaniline | $NaNO_2$ | 30% | $NH_4HSO_3$ | 75% | 32% |

*The concentration of the raw materials used in the actual synthesis will have a deviation of ±5 percentage point from the concentration listed in the table.

TABLE 24

Example 68-95 Raw material flow rate and ratio*

| | Raw material flow rate (g/min) | | | | Raw material molar ratio Raw material1/Raw material2/Raw material3/Raw material4 |
|---|---|---|---|---|---|
| Example | Raw material1 | Raw material2 | Raw material3 | Raw material4 | |
| 68 | 8.6 | 7.0 | 34.36 | 5.2 | 1.00:1.20:6.0:5.0 |
| 69 | 5.6 | 1.3 | 41.1 | 6.3 | 1.00:1.03:5.0:4.3 |
| 70 | 76 | 22 | 59.2 | 68 | 1.00:1.12:4.0:6.0 |
| 71 | 10.5 | 3.1 | 18.8 | 11.2 | 1.00:1.15:3.5:5.5 |
| 72 | 9.6 | 3.2 | 32.3 | 8.9 | 1.00:1.04:3.9:4.9 |
| 73 | 5.2 | 4.5 | 13.4 | 8.3 | 1.00:1.1:5.0:8.0 |
| 74 | 70 | 24 | 269 | 78.7 | 1.00:1.08:4.9:6.9 |
| 75 | 25 | 7.2 | 71.4 | 44.2 | 1.00:1.12:7.0:8.0 |
| 76 | 16 | 4.0 | 30.4 | 14.6 | 1.00:1.05:2.0:5.2 |
| 77 | 40.5 | 36.5 | 154.4 | 40.9 | 1.00:1.15:6.5:6.5 |
| 78 | 76 | 34.8 | 477 | 73 | 1.00:1.05:5.3:7.0 |
| 79 | 65.4 | 36 | 288 | 194.7 | 1.00:1.02:6.0:8.0 |
| 80 | 18 | 2.6 | 17.5 | 18.3 | 1.00:1.06:3.5:5.0 |
| 81 | 60 | 5.4 | 12.6 | 18.3 | 1:1.1:28:6.0 |
| 82 | 70 | 53 | 161.5 | 82.1 | 1:1.06:3.4:4.5 |
| 83 | 64 | 13.5 | 132 | 84.7 | 1:1.03:3.6:5.8 |
| 84 | 40 | 13.5 | 120 | 29.7 | 1:1.06:3.0:4.3 |
| 85 | 40 | 13.5 | 120 | 29.7 | 1:1.07:8.0:4.3 |
| 86 | 40 | 13.5 | 120 | 29.7 | 1:1.05:3.0:4.3 |
| 87 | 40 | 13.5 | 120 | 29.7 | 1:1.04:3.0:3.0 |
| 88 | 40 | 13.5 | 120 | 29.7 | 1:1.01:3.0:10.0 |
| 89 | 40 | 13.5 | 120 | 29.7 | 1:1.04:3.0:4.3 |
| 90 | 40 | 13.5 | 120 | 29.7 | 1:1.04:3.0:4.3 |
| 91 | 40 | 13.5 | 120 | 29.7 | 1:1.01:2.5:4.3 |
| 92 | 40 | 13.5 | 120 | 29.7 | 1:1.04:3.0:4.3 |
| 93 | 40 | 13.5 | 120 | 29.7 | 1:1.06:3.0:4.3 |
| 94 | 40 | 13.5 | 120 | 29.7 | 1:1.10:3.0:4.3 |
| 95 | 40 | 13.5 | 120 | 29.7 | 1:1.08:3.0:4.3 |

*The flow rate of the raw materials used in the actual synthesis will vary by ±2% from the flow rates listed in the table.

TABLE 25

Example 68-95 Temperature* and Yield and Purity of poducts

| Example | T1 (° C.) | T2 (° C.) | T3 (° C.) | T4 (° C.) | Reaction module features** | Total reaction time*** (min) | Product | Purity (%) | Yield (%) |
|---|---|---|---|---|---|---|---|---|---|
| 68 | 2 | 99 | 120 | 120 | 0.5-1.0 m, 0.5-1.0 mm | 5 | 4-hydrazinylbenzoic acid hydrochloride | 99.6 | 95 |
| 69 | 25 | 80 | 110 | 130 | 2.0-3.5 m, 1.6-2.0 mm | 8 | 4-hydrazinylbenzenesulfonic acid hydrochloride | 99.3 | 96.7 |
| 70 | 10 | 50 | 100 | 100 | 2.0-3.5 m-2.0-3.0 mm | 7 | 4-hydrazinylbenzonitrile hydrochloride | 99 | 98 |

TABLE 25-continued

Example 68-95 Temperature* and Yield and Purity of poducts

| Example | T1 (° C.) | T2 (° C.) | T3 (° C.) | T4 (° C.) | Reaction module features** | Total reaction time*** (min) | Product | Purity (%) | Yield (%) |
|---|---|---|---|---|---|---|---|---|---|
| 71 | 45 | 100 | 115 | 115 | 3.0-4.0 m, 5.0-6.35 mm | 10.5 | (4-nitrophenyl)hydrazine hydrochloride | 99.5 | 96.2 |
| 72 | 55 | 107 | 40 | 50 | 4.0-5.0 m, 6.35-12.7 mm | 13 | (3-nitrophenyl)hydrazine hydrochloride | 95 | 95 |
| 73 | 18 | 90 | 60 | 70 | 2.0-3.5 m, 3.0-5.0 mm | 5.5 | (2-nitrophenyl)hydrazine hydrochloride | 99 | 94.2 |
| 74 | 28 | 105 | 105 | 115 | 3.5-4.5 m, 25.4-55 mm | 6 | (2-methoxyphenyl)hydrazine hydrochloride | 99.4 | 96 |
| 75 | 25 | 50 | 50 | 70 | 2.0-3.5 m, 2.3-3.3 mm | 6.5 | (3-methoxyphenyl)hydrazine hydrochloride | 99.2 | 94.5 |
| 76 | 40 | 85 | 78 | 58 | 0.5-1.0 m, 1.0-5.0 mm | 7.5 | (4-methoxyphenyl)hydrazine hydrochloride | 99.3 | 94.7 |
| 77 | 65 | 90 | 95 | 140 | 1.0-2.0 m, 1.0-3.0 mm | 8.5 | (2,4-difluorophenyl)hydrazine hydrochloride | 99.3 | 95 |
| 78 | 35 | 80 | 80 | 95 | 1.5-2.5 m, 0.5-4.5 mm | 9 | (4-(trifluoromethyl)phenyl)hydrazine hydrochloride | 99 | 97.3 |
| 79 | 45 | 89 | 60 | 85 | 2.0-3.5 m, 12.7-25.4 mm | 15.5 | (4-chloro-2-fluorophenyl)hydrazine hydrochloride | 97.2 | 97.2 |
| 80 | 31 | 76 | 85 | 95 | 2.5-4.0 m, 1.5-3.5 mm | 18 | (2,4,6-trifluorophenyl)hydrazine hydrochloride | 99 | 97 |
| 81 | 10 | 76 | 87 | 150 | 1.0-2.0 m, 1.0-3.0 mm | 17.5 | (2,4-dichlorophenyl)hydrazine hydrochloride | 98 | 98.2 |
| 82 | 32 | 87 | 95 | 98 | 1.5-2.5 m, 0.5-4.5 mm | 11.5 | (2-chlorophenyl)hydrazine hydrochloride | 97 | 94.1 |
| 83 | 25 | 65 | 92 | 95 | 2.0-3.5 m, 12.7-25.4 mm | 10 | 3-fluoro-4-hydrazinylbenzonitrile hydrochloride | 95.4 | 94.7 |
| 84 | 28 | 90 | 110 | 120 | 1.5-2.5 m, 0.5-4.5 mm | 7.5 | (4-ethoxyphenyl)hydrazine hydrochloride | 98 | 94.3 |
| 85 | 33 | 90 | 125 | 120 | 1.5-2.5 m, 0.5-4.5 mm | 12.5 | (4-propoxyphenyl)hydrazine hydrochloride | 97 | 95.8 |
| 86 | 25 | 90 | 110 | 120 | 1.5-2.5 m, 0.5-4.5 mm | 12 | (4-butoxyphenyl)hydrazine hydrochloride | 99 | 97.8 |
| 87 | 32 | 90 | 70 | 120 | 1.5-2.5 m, 0.5-4.5 mm | 11 | (2-ethylphenyl)hydrazine hydrochloride | 98 | 98.4 |
| 88 | 35 | 90 | 110 | 120 | 1.5-2.5 m, 0.5-4.5 mm | 9.5 | (3-isopropylphenyl)hydrazine hydrochloride | 97 | 99.4 |
| 89 | 30 | 90 | 110 | 120 | 1.5-2.5 m, 0.5-4.5 mm | 13.5 | (4-butylphenyl)hydrazine hydrochloride | 98 | 99.5 |
| 90 | 29 | 108 | 110 | 120 | 1.5-2.5 m, 0.5-4.5 mm | 14 | (4-vinylphenyl)hydrazine hydrochloride | 99 | 95.4 |
| 91 | 26 | 90 | 110 | 120 | 1.5-2.5 m, 0.5-4.5 mm | 14.5 | (4-allylphenyl)hydrazine hydrochloride | 97 | 94 |
| 92 | 27 | 90 | 118 | 120 | 1.5-2.5 m, 0.5-4.5mm | 15 | (4-(but-3-en-1-yl)phenyl)hydrazine hydrochloride | 99 | 94.4 |
| 93 | 30 | 90 | 110 | 120 | 1.5-2.5 m, 0.5-4.5 mm | 5 | (2,3,4-trifluorophenyl)hydrazine hydrochloride | 98.5 | 95 |
| 94 | 29 | 90 | 110 | 120 | 1.5-2.5 m, 0.5-4.5 mm | 8 | (2,3,4,5-tetrafluorophenyl)hydrazine hydrochloride | 97 | 95.9 |
| 95 | 30 | 90 | 110 | 120 | 1.5-2.5 m, 0.5-4.5 mm | 7 | (2,3,4,5-tetrachlorophenyl)hydrazine hydrochloride | 99 | 98.3 |

*The temperature in the actual synthesis temperature section will vary by ±3° C. from the temperature listed in the table.
**The length of the channel used in the actual reactor module features will vary by ±0.5 m from the channel length listed in the table, and the channel diameter will have a deviation of ±0.5 mm.
***The total reaction time in the actual synthesis will vary by ±15 s from the total reaction time listed in the table.

What is claimed is:

1. A continuous flow process for the synthesis of phenylhydrazine salts and substituted phenylhydrazine salts, wherein the continuous flow process comprises a plurality of reactions comprising diazotization, reduction, acidic hydrolysis and salifying;
the continuous flow process is carried out in an integrated reactor;
wherein the continuous flow process comprises the steps of:
adding raw materials including acidic liquids of aniline or substituted aniline, diazotization reagents, reductants and acids into an inlet of the integrated reactor continuously, and,
obtaining phenylhydrazine salts and substituted phenylhydrazine salts in an outlet of the integrated reactor;
wherein a total reaction time is no more than 20 min;
no additional purification steps are included in the continuous flow process;
wherein, the continuous flow process is a continuously uninterrupted operation with the raw materials continuously added into the integrated reactor and products continuously produced without interruption, staying or waiting.

2. The continuous flow process as described in claim 1, wherein the reaction formula of the synthesis process is as follows:

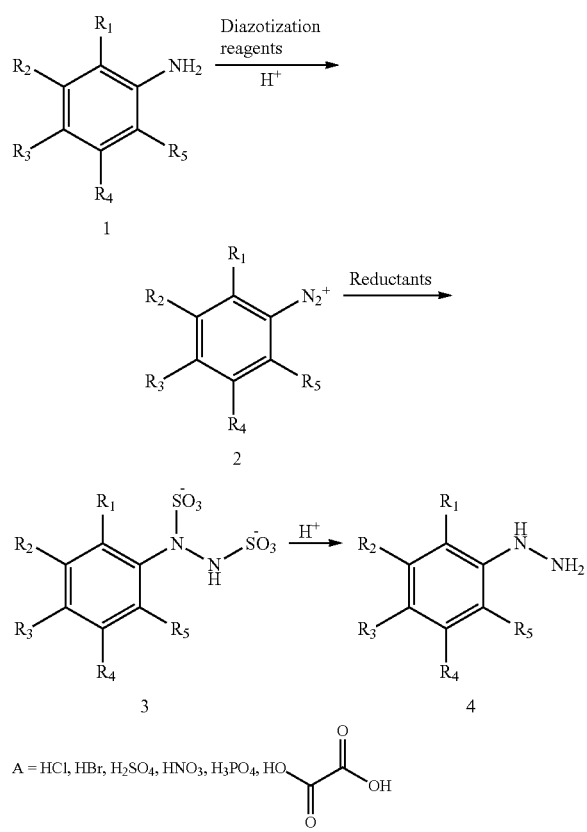

where:
R1 is selected from —H, —F, —Br, —CN, —NO2, —CF3, —SO3H, —COOH, C1-C4 alkoxy, C1-C4 saturated or unsaturated alkyl;
R2 is selected from —H, —F, —Br, —CN, —NO2, —CF3, —SO3H, —COOH, C1-C4 alkoxy, C1-C4 saturated or unsaturated alkyl;
R3 is selected from —H, —F, —Br, —CN, —NO2, —CF3, —SO3H, —COOH, C1-C4 alkoxy, C1-C4 saturated or unsaturated alkyl;
R4 is selected from —H, —F, —Br, —CN, —NO2, —CF3, —SO3H, —COOH, C1-C4 alkoxy, C1-C4 saturated or unsaturated alkyl;
R5 is selected from —H, —F, —Br, —CN, —NO2, —CF3, —SO3H, —COOH, C1-C4 alkoxy, C1-C4 saturated or unsaturated alkyl; and,
A is selected from HCl, HBr, H2SO4, HNO3, H3PO4, or HOOC—COOH.

3. The continuous flow process as described in claim 1, wherein the phenylhydrazine salts and the substituted phenylhydrazine salts are selected from phenylhydrazine hydrochloride, 4-hydrazinylbenzoic acid hydrochloride, 4-hydrazinylbenzenesulfonic acid hydrochloride, (2-fluorophenyl)hydrazine hydrochloride, (3-fluorophenyl)hydrazine hydrochloride, (4-fluorophenyl)hydrazine hydrochloride, (2,3-difluorophenyl)hydrazine hydrochloride, (2,4-difluorophenyl)hydrazine hydrochloride, (2,5-difluorophenyl)hydrazine hydrochloride, (2,6-difluorophenyl)hydrazine hydrochloride, (2,3,4-trifluorophenyl)hydrazine hydrochloride, (2,3,5-trifluorophenyl)hydrazine hydrochloride, (2,3,6-trifluorophenyl)hydrazine hydrochloride, (2,4,5-trifluorophenyl)hydrazine hydrochloride, (2,4,6-trifluorophenyl)hydrazine hydrochloride, (2,3,4,5-tetrafluorophenyl)hydrazine hydrochloride, (2,3,4,6-tetrafluorophenyl)hydrazine hydrochloride, (2,3,5,6-tetrafluorophenyl)hydrazine hydrochloride, (2-chlorophenyl)hydrazine hydrochloride (3-chlorophenyl)hydrazine hydrochloride, (2,3-dichlorophenyl)hydrazine hydrochloride, (2,4-dichlorophenyl)hydrazine hydrochloride, (2,5-dichlorophenyl)hydrazine hydrochloride, (2,6-dichlorophenyl)hydrazine hydrochloride, (2,3,4-trichlorophenyl)hydrazine hydrochloride, (2,3,5-trichlorophenyl)hydrazine hydrochloride, (2,3,6-trichlorophenyl)hydrazine hydrochloride, (2,4,5-trichlorophenyl)hydrazine hydrochloride, (2,4,6-trichlorophenyl)hydrazine hydrochloride, (2,3,4,5-tetrachlorophenyl)hydrazine hydrochloride, (2,3,4,6-tetrachlorophenyl)hydrazine hydrochloride, (2,3,5,6-tetrachlorophenyl)hydrazine hydrochloride, (2-bromophenyl)hydrazine hydrochloride, (3-bromophenyl)hydrazine hydrochloride, (4-bromophenyl)hydrazine hydrochloride, (2,3-dibromophenyl)hydrazine hydrochloride, (2,4-dibromophenyl)hydrazine hydrochloride, (2,5-dibromophenyl)hydrazine hydrochloride, (2,6-dibromophenyl)hydrazine hydrochloride, (2,3,4-tribromophenyl)hydrazine hydrochloride, (2,3,5-tribromophenyl)hydrazine hydrochloride, (2,3,6-tribromophenyl)hydrazine hydrochloride, (2,4,5-tribromophenyl)hydrazine hydrochloride, (2,4,6-tribromophenyl)hydrazine hydrochloride, (2,3,4,5-tetrabromophenyl)hydrazine hydrochloride, (2,3,4,6-tetrabromophenyl)hydrazine hydrochloride, (2,3,5,6-tetrabromophenyl)hydrazine hydrochloride, (2-methoxyphenyl)hydrazine hydrochloride, (3-methoxyphenyl)hydrazine hydrochloride, (4-methoxyphenyl)hydrazine hydrochloride, (2,3-dimethoxyphenyl)hydrazine hydrochloride, (2,4-dimethoxyphenyl)hydrazine hydrochloride, (2,5-dimethoxyphenyl)hydrazine hydrochloride, (2,6-dimethoxyphenyl)hydrazine hydrochloride, (3,4-dimethoxyphenyl)hydrazine hydrochloride, (3,5-dimethoxyphenyl)hydrazine hydrochloride, (2-ethylphenyl)hydrazine hydrochloride, (3-ethylphenyl)hydrazine hydrochloride, (4-ethylphenyl)hydrazine hydrochloride, (2,3-diethylphenyl)hydrazine hydrochloride, (2,4-diethylphenyl)hydrazine hydrochloride, (2,5-diethylphenyl)hydrazine hydrochloride, (2,6-diethylphenyl)hydrazine hydrochloride, (2-(trifluoromethyl)phenyl)hydrazine hydrochloride, (3-(trifluoromethyl)phenyl)hydrazine hydrochloride, (4-(trifluoromethyl)phenyl)hydrazine hydrochloride, (2,3-bis(trifluoromethyl)phenyl)hydrazine hydrochloride, (2,4-bis(trifluoromethyl)phenyl)hydrazine hydrochloride, (2,5-bis(trifluoromethyl)phenyl)hydrazine hydrochloride, (2,6-bis(trifluoromethyl)phenyl)hydrazine hydrochloride, (2,4,6-tris(trifluoromethyl)phenyl)hydrazine hydrochloride, 2-hydrazinylbenzonitrile hydrochloride, 3-hydrazinylbenzonitrile hydrochloride, 4-hydrazinylbenzonitrile hydrochloride, 3-hydrazinylphthalonitrile hydrochloride, 4-hydrazinylisophthalonitrile hydrochloride, 2-hydrazinylterephthalonitrile hydrochloride, 2-hydrazinylisophthalonitrile hydrochloride, (2-fluoro-3-methoxyphenyl)hydrazine hydrochloride, (2-fluoro-4-methoxyphenyl)hydrazine hydrochloride, (2-fluoro-5-methoxyphenyl)hydrazine hydrochloride, (2-fluoro-6-methoxyphenyl)hydrazine hydrochloride, (3-fluoro-2-methoxyphenyl)hydrazine hydrochloride, (3-fluoro-4-methoxyphenyl)hydrazine hydrochloride, (3-fluoro-5-methoxyphenyl)hydrazine hydrochloride, (5-fluoro-2-methoxyphenyl)hydrazine hydrochloride, (4-fluoro-2-methoxyphenyl)hydrazine hydrochloride, (4-fluoro-3-methoxyphenyl)hydrazine hydrochloride, (2-choloro-3-methoxyphenyl)hydrazine hydrochloride, (2-choloro-4-methoxyphenyl)hydrazine hydrochloride, (2-choloro-5- methoxyphenyl)hydrazine hydrochloride, (2-choloro-6-methoxyphenyl)hydrazine hydrochloride, (3-choloro-2-methoxyphenyl)hydrazine hydrochloride, (3-choloro-4-methoxyphenyl)hydrazine hydrochloride, (3-choloro-5-methoxyphenyl)hydrazine hydrochloride, (5-choloro-2-methoxyphenyl)hydrazine hydrochloride, (4-choloro-2-methoxyphenyl)hydrazine hydrochloride, (4-choloro-3-methoxyphenyl)hydrazine hydrochloride, (2-nitrophenyl)hydrazine hydrochloride, (3-nitrophenyl)hydrazine hydrochloride, (4-nitrophenyl)hydrazine hydrochloride, (2-methoxy-3-nitrophenyl)hydrazine hydrochloride, (2-methoxy-4-nitrophenyl)hydrazine hydrochloride, (2-methoxy-5-nitrophenyl)hydrazine hydrochloride, (2-methoxy-6-nitrophenyl)hydrazine hydrochloride, (3-methoxy-2-nitrophenyl)hydrazine hydrochloride, (4-methoxy-2-nitrophenyl)hydrazine hydrochloride, (5-methoxy-2-nitrophenyl)hydrazine hydrochloride, (3-methoxy-5-nitrophenyl)hydrazine hydrochloride, (3-methoxy-4-nitrophenyl)hydrazine hydrochloride, (4-methoxy-3-nitrophenyl)hydrazine hydrochloride, (4-bromo-2-fluorophenyl)hydrazine hydrochloride, 2-hydrazinylbenzoic acid hydrochloride, 3-hydrazinylbenzoic acid hydrochloride, (4-chloro-2-fluorophenyl)hydrazine hydrochloride, 3-fluoro-4-hydrazinylbenzonitrile hydrochloride, (4-ethoxyphenyl)hydrazine hydrochloride, (4-propoxyphenyl)hydrazine hydrochloride, (4-butoxyphenyl)hydrazine hydrochloride, (3-isopropylphenyl)hydrazine hydrochloride, (4-propylphenyl)hydrazine hydrochloride, (4-vinylphenyl)hydrazine hydrochloride, (4-allylphenyl)hydrazine hydrochloride, (4-(but-3-en-1-yl)phenyl)hydrazine hydrochloride; phenylhydrazine hydrobromide, 4-hydrazinylbenzoic acid hydrobromide, 4-hydrazinylbenzenesulfonic acid hydrobromide, (2-fluorophenyl)hydrazine hydrobromide, (3-fluorophenyl)hydrazine hydrobromide, (4-fluorophenyl)hydrazine hydrobromide, (2,3-difluorophenyl)hydrazine hydrobromide, (2,4-difluorophenyl)hydrazine hydrobromide, (2,5-difluorophenyl)hydrazine hydrobromide, (2,6-difluorophenyl)hydrazine hydrobromide, (2,3,4-trifluorophenyl)hydrazine hydrobromide, (2,3,5-trifluorophenyl)hydrazine hydrobromide, (2,3,6-trifluorophenyl) hydrazine hydrobromide, (2,4,5-trifluorophenyl)hydrazine hydrobromide, (2,4,6-trifluorophenyl)hydrazine hydrobromide, (2,3,4,5-tetrafluorophenyl)hydrazine hydrobromide, (2,3,4,6-tetrafluorophenyl)hydrazine hydrobromide, (2,3,5,6-tetrafluorophenyl)hydrazine hydrobromide, (2-chlorophenyl)hydrazine hydrobromide, (3-chlorophenyl)hydrazine hydrobromide, (2,3-dichlorophenyl)hydrazine hydrobromide, (2,4-dichlorophenyl)hydrazine hydrobromide, (2,5-dichlorophenyl)hydrazine hydrobromide, (2,6-dichlorophenyl)hydrazine hydrobromide, (2,3,4-trichlorophenyl) hydrazine hydrobromide, (2,3,5-trichlorophenyl)hydrazine hydrobromide, (2,3,6-trichlorophenyl)hydrazine hydrobromide, (2,4,5-trichlorophenyl)hydrazine hydrobromide, (2,4,6-trichlorophenyl)hydrazine hydrobromide, (2,3,4,5-tetrachlorophenyl)hydrazine hydrobromide, (2,3,4,6-tetrachlorophenyl)hydrazine hydrobromide, (2,3,5,6-tetrachlorophenyl)hydrazine hydrobromide, (2-bromophenyl)hydrazine hydrobromide, (3-bromophenyl)hydrazine hydrobromide, (4-bromophenyl)hydrazine hydrobromide, (2,3-dibromophenyl)hydrazine hydrobromide, (2,4-dibromophenyl)hydrazine hydrobromide, (2,5-dibromophenyl)hydrazine hydrobromide, (2,6-dibromophenyl)hydrazine hydrobromide, (2,3,4-tribromophenyl)hydrazine hydrobromide, (2,3,5-tribromophenyl)hydrazine hydrobromide, (2,3,6-tribromophenyl)hydrazine hydrobromide, (2,4,5-tribromophenyl)hydrazine hydrobromide, (2,4,6-tribromophenyl)hydrazine hydrobromide, (2,3,4,5-tetrabromophenyl)hydrazine hydrobromide, (2,3,4,6-tetrabromophenyl)hydrazine hydrobromide, (2,3,5,6-tetrabromophenyl)hydrazine hydrobromide, (2-methoxyphenyl)hydrazine hydrobromide, (3-methoxyphenyl)hydrazine hydrobromide, (4-methoxyphenyl)hydrazine hydrobromide, (2,3-dimethoxyphenyl)hydrazine hydrobromide, (2,4-dimethoxyphenyl)hydrazine hydrobromide, (2,5-dimethoxyphenyl)hydrazine hydrobromide, (2,6-dimethoxyphenyl)hydrazine hydrobromide, (3,4-dimethoxyphenyl)hydrazine hydrobromide, (3,5-dimethoxyphenyl)hydrazine hydrobromide, (2-ethylphenyl)hydrazine hydrobromide, (3-ethylphenyl)hydrazine hydrobromide, (4-ethylphenyl)hydrazine hydrobromide, (2,3-diethylphenyl)hydrazine hydrobromide, (2,4-diethylphenyl)hydrazine hydrobromide, (2,5-diethylphenyl)hydrazine hydrobromide, (2,6-diethylphenyl)hydrazine hydrobromide, (2-(trifluoromethyl)phenyl)hydrazine hydrobromide, (3-(trifluoromethyl)phenyl)hydrazine hydrobromide, (4-(trifluoromethyl)phenyl)hydrazine hydrobromide, (2,3-bis(trifluoromethyl)phenyl)hydrazine hydrobromide, (2,4-bis(trifluoromethyl)phenyl)hydrazine hydrobromide, (2,5-bis(trifluoromethyl)phenyl)hydrazine hydrobromide, (2,6-bis(trifluoromethyl)phenyl)hydrazine hydrobromide, (2,4,6-tris(trifluoromethyl)phenyl)hydrazine hydrobromide, 2-hydrazinylbenzonitrile hydrobromide, 3-hydrazinylbenzonitrile hydrobromide, 4-hydrazinylbenzonitrile hydrobromide, 3-hydrazinylphthalonitrile hydrobromide, 4-hydrazinylisophthalonitrile hydrobromide, 2-hydrazinylterephthalonitrile hydrobromide, 2-hydrazinylisophthalonitrile hydrobromide, (2-fluoro-3-methoxyphenyl)hydrazine hydrobromide, (2-fluoro-4-methoxyphenyl)hydrazine hydrobromide, (2-fluoro-5-methoxyphenyl) hydrazine hydrobromide, (2-fluoro-6-methoxyphenyl) hydrazine hydrobromide, (3-fluoro-2-methoxyphenyl) hydrazine hydrobromide, (3-fluoro-4-methoxyphenyl) hydrazine hydrobromide, (3-fluoro-5-methoxyphenyl) hydrazine hydrobromide, (5-fluoro-2-methoxyphenyl) hydrazine hydrobromide, (4-fluoro-2-methoxyphenyl) hydrazine hydrobromide, (4-fluoro-3-methoxyphenyl) hydrazine hydrobromide, (2-choloro-3-methoxyphenyl) hydrazine hydrobromide, (2-choloro-4-methoxyphenyl) hydrazine hydrobromide, (2-choloro-5-methoxyphenyl) hydrazine hydrobromide, (2-choloro-6-methoxyphenyl) hydrazine hydrobromide, (3-choloro-2-methoxyphenyl) hydrazine hydrobromide, (3-choloro-4-methoxyphenyl) hydrazine hydrobromide, (3-choloro-5-methoxyphenyl) hydrazine hydrobromide, (5-choloro-2-methoxyphenyl) hydrazine hydrobromide, (4-choloro-2-methoxyphenyl) hydrazine hydrobromide, (4-choloro-3-methoxyphenyl) hydrazine hydrobromide, (2-nitrophenyl)hydrazine hydrobromide, (3-nitrophenyl)hydrazine hydrobromide, (4-nitrophenyl)hydrazine hydrobromide, (2-methoxy-3-nitrophenyl)hydrazine hydrobromide, (2-methoxy-4-nitrophenyl)hydrazine hydrobromide, (2-methoxy-5-nitrophenyl)hydrazine hydrobromide, (2-methoxy-6-nitrophenyl)hydrazine hydrobromide, (3-methoxy-2-nitrophenyl)hydrazine hydrobromide, (4-methoxy-2-nitrophenyl)hydrazine hydrobromide, (5-methoxy-2-nitrophenyl)hydrazine hydrobromide, (3-methoxy-5-nitrophenyl)hydrazine hydrobromide, (3-methoxy-4-nitrophenyl)hydrazine hydrobromide, (4-methoxy-3-nitrophenyl)hydrazine hydrobromide, (4-bromo-2-fluorophenyl)hydrazine hydrobromide, 2-hydrazinylbenzoic acid hydrobromide, 3-hydrazinylbenzoic acid hydrobromide, (4-chloro-2-fluorophenyl)hydrazine hydrobromide, 3-fluoro-4-hydrazinylbenzonitrile hydrobromide, (4-ethoxyphenyl)hydrazine hydrobromide, (4-propoxyphenyl)hydrazine hydrobromide, (4-butoxyphenyl)hydrazine hydrobromide, (3-isopropylphenyl)hydrazine hydrobromide, (4-propylphenyl)hydrazine hydrobromide, (4-vinylphenyl)hydrazine hydrobromide, (4-allylphenyl)hydrazine hydrobromide, (4-(but-3-en-1-yl)phenyl)hydrazine hydrobromide; phenylhydrazine sulfate, 4-hydrazinylbenzoic acid sulfate, 4-hydrazinylbenzenesulfonic acid sulfate, (2-fluorophenyl)hydrazine sulfate, (3-fluorophenyl)hydrazine sulfate, (4-fluorophenyl)hydrazine sulfate, (2,3-difluorophenyl)hydrazine sulfate, (2,4-difluorophenyl)hydrazine sulfate, (2,5-difluorophenyl)hydrazine sulfate, (2,6-difluorophenyl)hydrazine sulfate, (2,3,4-trifluorophenyl)hydrazine sulfate, (2,3,5-trifluorophenyl)hydrazine sulfate, (2,3,6-trifluorophenyl)hydrazine sulfate, (2,4,5-trifluorophenyl)hydrazine sulfate, (2,4,6-trifluorophenyl)hydrazine sulfate, (2,3,4,5-tetrafluorophenyl)hydrazine sulfate, (2,3,4,6-tetrafluorophenyl)hydrazine sulfate, (2,3,5,6-tetrafluorophenyl)hydrazine sulfate, (2-chlorophenyl)hydrazine sulfate, (3-chlorophenyl)hydrazine sulfate, (2,3-dichlorophenyl)hydrazine sulfate, (2,4-dichlorophenyl)hydrazine sulfate, (2,5-dichlorophenyl)hydrazine sulfate, (2,5-dichlorophenyl)hydrazine sulfate, (2,3,4-trichlorophenyl)hydrazine sulfate, (2,3,5-trichlorophenyl)hydrazine sulfate, (2,3,6-trichlorophenyl)hydrazine sulfate, (2,4,5-trichlorophenyl)hydrazine sulfate, (2,4,6-trichlorophenyl)hydrazine sulfate, (2,3,4,5-tetrachlorophenyl)hydrazine sulfate, (2,3,4,6-tetrachlorophenyl)hydrazine sulfate, (2,3,5,6-tetrachlorophenyl)hydrazine sulfate, (2-bromophenyl)hydrazine sulfate, (3-bromophenyl)hydrazine sulfate, (4-bromophenyl)hydrazine sulfate, (2,3-dibromophenyl)hydrazine sulfate, (2,4-dibromophenyl)hydrazine sulfate, (2,5-dibromophenyl)hydrazine sulfate, (2,6-dibromophenyl)hydrazine sulfate, (2,3,4-tribromophenyl)hydrazine sulfate, (2,3,5-tribromophenyl)hydrazine sulfate, (2,3,6-tribromophenyl)hydrazine sulfate, (2,4,5-tribromophenyl)hydrazine sulfate, (2,4,6-tribromophenyl)hydrazine sulfate, (2,3,4,5-tetrabromophenyl)hydrazine sulfate, (2,3,4,6-tetrabromophenyl)hydrazine sulfate, (2,3,5,6-tetrabromophenyl)hydrazine sulfate, (2-methoxyphenyl)hydrazine sulfate, (3-methoxyphenyl)hydrazine sulfate, (4-methoxyphenyl)hydrazine sulfate, (2,3-dimethoxyphenyl)hydrazine sulfate, (2,4-dimethoxyphenyl)hydrazine sulfate, (2,5-dimethoxyphenyl)hydrazine sulfate, (2,5-dimethoxyphenyl)hydrazine sulfate, (3,4-dimethoxyphenyl)hydrazine sulfate, (3,5-dimethoxyphenyl)hydrazine sulfate, (2-ethylphenyl)hydrazine sulfate, (3-ethylphenyl)hydrazine sulfate, (4-ethylphenyl)hydrazine sulfate, (2,3-diethylphenyl)hydrazine sulfate, (2,4-diethylphenyl)hydrazine sulfate, (2,5-diethylphenyl)hydrazine sulfate, (2,6-diethylphenyl)hydrazine sulfate, (2-(trifluoromethyl)phenyl)hydrazine sulfate, (3-(trifluoromethyl)phenyl)hydrazine sulfate, (4-(trifluoromethyl)phenyl)hydrazine sulfate, (2,3-bis(trifluoromethyl)phenyl)hydrazine sulfate, (2,4-bis(trifluoromethyl)phenyl)hydrazine sulfate, (2,5-bis(trifluoromethyl)phenyl)hydrazine sulfate, (2,6-bis(trifluoromethyl)phenyl)hydrazine sulfate, (2,4,6-tris(trifluoromethyl)phenyl)hydrazine sulfate, 2-hydrazinylbenzonitrile sulfate, 3-hydrazinylbenzonitrile sulfate, 4-hydrazinylbenzonitrile sulfate, 3-hydrazinylphthalonitrile sulfate, 4-hydrazinylisophthalonitrile sulfate, 2-hydrazinylterephthalonitrile sulfate, 2-hydrazinylisophthalonitrile sulfate, (2-fluoro-3-methoxyphenyl)hydrazine sulfate, (2-fluoro-4-methoxyphenyl)hydrazine sulfate, (2-fluoro-5-methoxyphenyl)hydrazine sulfate, (2-fluoro-6-methoxyphenyl)hydrazine sulfate, (3-fluoro-2-methoxyphenyl)hydrazine sulfate, (3-fluoro-4-methoxyphenyl)hydrazine sulfate, (3-fluoro-5-methoxyphenyl)hydrazine sulfate, (5-fluoro-2-methoxyphenyl)hydrazine sulfate, (4-fluoro-2-methoxyphenyl)hydrazine sulfate, (4-fluoro-3-methoxyphenyl)hydrazine sulfate, (2-choloro-3-methoxyphenyl)hydrazine sulfate, (2-choloro-4-methoxyphenyl)hydrazine sulfate, (2-choloro-5-methoxyphenyl)hydrazine sulfate, (2-choloro-6-methoxyphenyl)hydrazine sulfate, (3-choloro-2-methoxyphenyl)hydrazine sulfate, (3-choloro-4-methoxyphenyl)hydrazine sulfate, (3-choloro-5-methoxyphenyl)hydrazine sulfate, (5-choloro-2-methoxyphenyl)hydrazine sulfate, (4-choloro-2-methoxyphenyl)hydrazine sulfate, (4-choloro-3-methoxyphenyl)hydrazine sulfate, (2-nitrophenyl)hydrazine sulfate, (3-nitrophenyl)hydrazine sulfate, (4-nitrophenyl)hydrazine sulfate, (2-methoxy-3-nitrophenyl)hydrazine sulfate, (2-methoxy-4-nitrophenyl)hydrazine sulfate, (2-methoxy-5-nitrophenyl)hydrazine sulfate, (2-methoxy-6-nitrophenyl)hydrazine sulfate, (3-methoxy-2-nitrophenyl)hydrazine sulfate, (4-methoxy-2-nitrophenyl)hydrazine sulfate, (5-methoxy-2-nitrophenyl)hydrazine sulfate, (3-methoxy-5-nitrophenyl)hydrazine sulfate, (3-methoxy-4-nitrophenyl)hydrazine sulfate, (4-methoxy-3-nitrophenyl)hydrazine sulfate, (4-bromo-2-fluorophenyl)hydrazine sulfate, 2-hydrazinylbenzoic acid sulfate, 3-hydrazinylbenzoic acid sulfate, (4-chloro-2-fluorophenyl)hydrazine sulfate, 3-fluoro-4-hydrazinylbenzonitrile sulfate, (4-ethoxyphenyl)hydrazine sulfate, (4-propoxyphenyl)hydrazine sulfate, (4-butoxyphenyl)hydrazine sulfate, (3-isopropylphenyl)hydrazine sulfate, (4-propylphenyl)hydrazine sulfate, (4-vinylphenyl)hydrazine sulfate, (4-allylphenyl)hydrazine sulfate, (4-(but-3-en-1-yl)phenyl)hydrazine sulfate; phenylhydrazine oxalate, 4-hydrazinylbenzoic acid oxalate, 4-hydrazinylbenzenesulfonic acid oxalate, (2-fluorophenyl)hydrazine oxalate, (3-fluorophenyl)hydrazine oxalate, (4-fluorophenyl)hydrazine oxalate, (2,3-difluorophenyl)hydrazine oxalate, (2,4-difluorophenyl)hydrazine oxalate, (2,5-difluorophenyl)hydrazine oxalate, (2,5-difluorophenyl)hydrazine oxalate, (2,3,4-trifluorophenyl)hydrazine oxalate, (2,3,5-trifluorophenyl)hydrazine oxalate, (2,3,6-trifluorophenyl)hydrazine oxalate, (2,4,5-trifluorophenyl)hydrazine oxalate, (2,4,6-trifluorophenyl)hydrazine oxalate, (2,3,4,5-tetrafluorophenyl)hydrazine oxalate, (2,3,4,6-tetrafluorophenyl)hydrazine oxalate, (2,3,5,6-tetrafluorophenyl)hydrazine oxalate, (2-chlorophenyl)hydrazine oxalate, (3-chlorophenyl)hydrazine oxalate, (2,3-dichlorophenyl)hydrazine oxalate, (2,4-dichlorophenyl)hydrazine oxalate, (2,5-dichlorophenyl)hydrazine oxalate, (2,6-dichlorophenyl)hydrazine oxalate, (2,3,4-trichlorophenyl)hydrazine oxalate, (2,3,5-trichlorophenyl)hydrazine oxalate, (2,3,6-trichlorophenyl)hydrazine oxalate, (2,4,5-trichlorophenyl)hydrazine oxalate, (2,4,6-trichlorophenyl)hydrazine oxalate, (2,3,4,5-tetrachlorophenyl)hydrazine oxalate, (2,3,4,6-tetrachlorophenyl)hydrazine oxalate, (2,3,5,6-tetrachlorophenyl)hydrazine oxalate, (2-bromophenyl)hydrazine oxalate, (3-bromophenyl)hydrazine oxalate, (4-bromophenyl)hydrazine oxalate, (2,3-dibromophenyl)hydrazine oxalate, (2,4-dibromophenyl)hydrazine oxalate, (2,5-dibromophenyl)hydrazine oxalate, (2,6-dibromophenyl)hydrazine oxalate, (2,3,4-tribromophenyl)hydrazine oxalate, (2,3,5-tribromophenyl)hydrazine oxalate, (2,3,6-tribromophenyl)hydrazine oxalate, (2,4,5-tribromophenyl)hydrazine oxalate, (2,4,6-tribromophenyl)hydrazine oxalate, (2,3,4,5-tetrabromophenyl)hydrazine oxalate, (2,3,4,6-tetrabromophenyl)hydrazine oxalate, (2,3,5,6-tetrabromophenyl)hydrazine oxalate, (2-methoxyphenyl)hydrazine oxalate, (3-methoxyphenyl)hydrazine oxalate, (4-methoxyphenyl)hydrazine oxalate, (2,3-dimethoxyphenyl)hydrazine oxalate, (2,4-dimethoxyphenyl)hydrazine oxalate, (2,5-dimethoxyphenyl)hydrazine oxalate, (2,5-dimethoxyphenyl)hydrazine oxalate, (3,4-dimethoxyphenyl) hydrazine oxalate, (3,5-dimethoxyphenyl)hydrazine oxalate, (2-ethylphenyl)hydrazine oxalate, (3-ethylphenyl) hydrazine oxalate, (4-ethylphenyl)hydrazine oxalate, (2,3-diethylphenyl)hydrazine oxalate, (2,4-diethylphenyl)hydrazine oxalate, (2,5-diethylphenyl)hydrazine oxalate, (2,6-diethylphenyl)hydrazine oxalate, (2-(trifluoromethyl) phenyl)hydrazine oxalate, (3-(trifluoromethyl)phenyl) hydrazine oxalate, (4-(trifluoromethyl)phenyl)hydrazine oxalate, (2,3-bis(trifluoromethyl)phenyl)hydrazine oxalate, (2,4-bis(trifluoromethyl)phenyl)hydrazine oxalate, (2,5-bis(trifluoromethyl)phenyl)hydrazine oxalate, (2,6-bis(trifluoromethyl)phenyl)hydrazine oxalate, (2,4,6-tris(trifluoromethyl)phenyl)hydrazine oxalate, 2-hydrazinylbenzonitrile oxalate, 3-hydrazinylbenzonitrile oxalate, 4-hydrazinylbenzonitrile oxalate, 3-hydrazinylphthalonitrile oxalate, 4-hydrazinylisophthalonitrile oxalate, 2-hydrazinylterephthalonitrile oxalate, 2-hydrazinylisophthalonitrile oxalate, (2-fluoro-3-methoxyphenyl)hydrazine oxalate, (2-fluoro-4-methoxyphenyl)hydrazine oxalate, (2-fluoro-5-methoxyphenyl)hydrazine oxalate, (2-fluoro-6-methoxyphenyl)hydrazine oxalate, (3-fluoro-2-methoxyphenyl)hydrazine oxalate, (3-fluoro-4-methoxyphenyl)hydrazine oxalate, (3-fluoro-5-methoxyphenyl)hydrazine oxalate, (5-fluoro-2-methoxyphenyl)hydrazine oxalate, (4-fluoro-2-methoxyphenyl)hydrazine oxalate, (4-fluoro-3-methoxyphenyl)hydrazine oxalate, (2-choloro-3-methoxyphenyl)hydrazine oxalate, (2-choloro-4-methoxyphenyl)hydrazine oxalate, (2-choloro-5-methoxyphenyl)hydrazine oxalate, (2-choloro-6-methoxyphenyl)hydrazine oxalate, (3-choloro-2-methoxyphenyl)hydrazine oxalate, (3-choloro-4-methoxyphenyl)hydrazine oxalate, (3-choloro-5-methoxyphenyl) hydrazine oxalate, (5-choloro-2-methoxyphenyl)hydrazine oxalate, (4-choloro-2-methoxyphenyl)hydrazine oxalate, (4-choloro-3-methoxyphenyl)hydrazine oxalate, (2-nitrophenyl)hydrazine oxalate, (3-nitrophenyl)hydrazine oxalate, (4-nitrophenyl)hydrazine oxalate, (2-methoxy-3-nitrophenyl)hydrazine oxalate, (2-methoxy-4-nitrophenyl)hydrazine oxalate, (2-methoxy-5-nitrophenyl)hydrazine oxalate, (2-methoxy-5-nitrophenyl)hydrazine oxalate, (3-methoxy-2-nitrophenyl)hydrazine oxalate, (4-methoxy-2-nitrophenyl)hydrazine oxalate, (5-methoxy-2-nitrophenyl)hydrazine oxalate, (3-methoxy-5-nitrophenyl)hydrazine oxalate, (3-methoxy-4-nitrophenyl)hydrazine oxalate, (4-methoxy-3-nitrophenyl)hydrazine oxalate, (4-bromo-2-fluorophenyl) hydrazine oxalate, 2-hydrazinylbenzoic acid oxalate, 3-hydrazinylbenzoic acid oxalate, (4-chloro-2-fluorophenyl) hydrazine oxalate, 3-fluoro-4-hydrazinylbenzonitrile oxalate, (4-ethoxyphenyl)hydrazine oxalate, (4-propoxyphenyl)hydrazine oxalate, (4-butoxyphenyl)hydrazine oxalate, (3-isopropylphenyl)hydrazine oxalate, (4-propylphenyl)hydrazine oxalate, (4-vinylphenyl)hydrazine oxalate, (4-allylphenyl)hydrazine oxalate, (4-(but-3-en-1-yl) phenyl)hydrazine oxalate; phenylhydrazine nitrate, 4-hydrazinylbenzoic acid nitrate, 4-hydrazinylbenzenesulfonic acid nitrate, (2-fluorophenyl)hydrazine nitrate, (3-fluorophenyl)hydrazine nitrate, (4-fluorophenyl)hydrazine nitrate, (2,3-difluorophenyl)hydrazine nitrate, (2,4-difluorophenyl) hydrazine nitrate, (2,5-difluorophenyl)hydrazine nitrate, (2,6-difluorophenyl)hydrazine nitrate, (2,3,4-trifluorophenyl)hydrazine nitrate, (2,3,5-trifluorophenyl)hydrazine nitrate, (2,3,6-trifluorophenyl)hydrazine nitrate, (2,4,5-trifluorophenyl)hydrazine nitrate, (2,4,6-trifluorophenyl)hydrazine nitrate, (2,3,4,5-tetrafluorophenyl)hydrazine nitrate, (2,3,4,5-tetrafluorophenyl)hydrazine nitrate, (2,3,5,6-tetrafluorophenyl)hydrazine nitrate, (2-chlorophenyl)hydrazine nitrate, (3-chlorophenyl)hydrazine nitrate, (2,3-dichlorophenyl)hydrazine nitrate, (2,4-dichlorophenyl)hydrazine nitrate, (2,5-dichlorophenyl)hydrazine nitrate, (2,6-dichlorophenyl)hydrazine nitrate, (2,3,4-trichlorophenyl)hydrazine nitrate, (2,3,5-trichlorophenyl)hydrazine nitrate, (2,3,6-trichlorophenyl)hydrazine nitrate, (2,4,5-trichlorophenyl) hydrazine nitrate, (2,4,6-trichlorophenyl)hydrazine nitrate, (2,3,4,5-tetrachlorophenyl)hydrazine nitrate, (2,3,4,6-tetrachlorophenyl)hydrazine nitrate, (2,3,5,6-tetrachlorophenyl) hydrazine nitrate, (2-bromophenyl)hydrazine nitrate, (3-bromophenyl)hydrazine nitrate, (4-bromophenyl)hydrazine nitrate, (2,3-dibromophenyl)hydrazine nitrate, (2,4-dibromophenyl)hydrazine nitrate, (2,5-dibromophenyl)hydrazine nitrate, (2,6-dibromophenyl)hydrazine nitrate, (2,3,4-tribromophenyl)hydrazine nitrate, (2,3,5-tribromophenyl)hydrazine nitrate, (2,3,6-tribromophenyl)hydrazine nitrate, (2,4,5-tribromophenyl)hydrazine nitrate, (2,4,6-tribromophenyl) hydrazine nitrate, (2,3,4,5-tetrabromophenyl)hydrazine nitrate, (2,3,4,6-tetrabromophenyl)hydrazine nitrate, (2,3,5,6-tetrabromophenyl)hydrazine nitrate, (2-methoxyphenyl) hydrazine nitrate, (3-methoxyphenyl)hydrazine nitrate, (4-methoxyphenyl)hydrazine nitrate, (2,3-dimethoxyphenyl)hydrazine nitrate, (2,4-dimethoxyphenyl)hydrazine nitrate, (2,5-dimethoxyphenyl)hydrazine nitrate, (2,6-dimethoxyphenyl)hydrazine nitrate, (3,4-dimethoxyphenyl)hydrazine nitrate, (3,5-dimethoxyphenyl)hydrazine nitrate, (2-ethylphenyl)hydrazine nitrate, (3-ethylphenyl)hydrazine nitrate, (4-ethylphenyl)hydrazine nitrate, (2,3-diethylphenyl)hydrazine nitrate, (2,4-diethylphenyl)hydrazine nitrate, (2,5-diethylphenyl)hydrazine nitrate, (2,6-diethylphenyl)hydrazine nitrate, (2-(trifluoromethyl)phenyl)hydrazine nitrate, (3-(trifluoromethyl)phenyl)hydrazine nitrate, (4-(trifluoromethyl)phenyl)hydrazine nitrate, (2,3-bis(trifluoromethyl)phenyl)hydrazine nitrate, (2,4-bis(trifluoromethyl) phenyl)hydrazine nitrate, (2,5-bis(trifluoromethyl)phenyl) hydrazine nitrate, (2,6-bis(trifluoromethyl)phenyl)hydrazine nitrate, (2,4,6-tris(trifluoromethyl)phenyl)hydrazine nitrate, 2-hydrazinylbenzonitrile nitrate, 3-hydrazinylbenzonitrile nitrate, 4-hydrazinylbenzonitrile nitrate, 3-hydrazinylphthalonitrile nitrate, 4-hydrazinylisophthalonitrile nitrate, 2-hydrazinylterephthalonitrile nitrate, 2-hydrazinylisophthalonitrile nitrate, (2-fluoro-3-methoxyphenyl)hydrazine nitrate, (2-fluoro-4-methoxyphenyl)hydrazine nitrate, (2-fluoro-5-methoxyphenyl)hydrazine nitrate, (2-fluoro-6-methoxyphenyl)hydrazine nitrate, (3-fluoro-2-methoxyphenyl)hydrazine nitrate, (3-fluoro-4-methoxyphenyl)hydrazine nitrate, (3-fluoro-5-methoxyphenyl)hydrazine nitrate, (5-fluoro-2-methoxyphenyl)hydrazine nitrate, (4-fluoro-2-methoxyphenyl)hydrazine nitrate, (4-fluoro-3-methoxyphenyl)hydrazine nitrate, (2-choloro-3-methoxyphenyl)hydrazine nitrate, (2-choloro-4-methoxyphenyl)hydrazine nitrate, (2-choloro-5-methoxyphenyl)hydrazine nitrate, (2-choloro-6-methoxyphenyl)hydrazine nitrate, (3-choloro-2-methoxyphenyl)hydrazine nitrate, (3-choloro-4-methoxyphenyl)hydrazine nitrate, (3-choloro-5-methoxyphenyl)hydrazine nitrate, (5-choloro-2-methoxyphenyl)hydrazine nitrate, (4-choloro-2-methoxyphenyl)hydrazine nitrate, (4-choloro-3-methoxyphenyl)hydrazine nitrate, (2-nitrophenyl)hydrazine nitrate, (3-nitrophenyl)hydrazine nitrate, (4-nitrophenyl)hydrazine nitrate, (2-methoxy-3-nitrophenyl)hydrazine nitrate, (2-methoxy-21-nitrophenyl)hydrazine nitrate, (2-methoxy-5-nitrophenyl)hydrazine nitrate, (2-methoxy-6-nitrophenyl) hydrazine nitrate, (3-methoxy-2-nitrophenyl)hydrazine nitrate, (4-methoxy-2-nitrophenyl)hydrazine nitrate, (5-methoxy-2-nitrophenyl)hydrazine nitrate, (3-methoxy-5-nitrophenyl)hydrazine nitrate, (3-methoxy-4-nitrophenyl) hydrazine nitrate, (4-methoxy-3-nitrophenyl)hydrazine nitrate, (4-bromo-2-fluorophenyl)hydrazine nitrate, 2-hydrazinylbenzoic acid nitrate, 3-hydrazinylbenzoic acid nitrate, (4-chloro-2-fluorophenyl)hydrazine nitrate, 3-fluoro-4-hydrazinylbenzonitrile nitrate, (4-ethoxyphenyl)hydrazine nitrate, (4-propoxyphenyl)hydrazine nitrate, (4-butoxyphenyl)hydrazine nitrate, (3-isopropylphenyl)hydrazine nitrate, (4-propylphenyl)hydrazine nitrate, (4-vinylphenyl)hydrazine nitrate, (4-allylphenyl)hydrazine nitrate, (4-(but-3-en-1-yl)phenyl)hydrazine nitrate; phenylhydrazine phosphate, 4-hydrazinylbenzoic acid phosphate, 4-hydrazinylbenzenesulfonic acid phosphate, (2-fluorophenyl)hydrazine phosphate, (3-fluorophenyl)hydrazine phosphate, (4-fluorophenyl)hydrazine phosphate, (2,3-difluorophenyl)hydrazine phosphate, (2,4-difluorophenyl)hydrazine phosphate, (2,5-difluorophenyl)hydrazine phosphate, (2,6-difluorophenyl)hydrazine phosphate, (2,3,4-trifluorophenyl)hydrazine phosphate, (2,3,5-trifluorophenyl)hydrazine phosphate, (2,3,6-trifluorophenyl)hydrazine phosphate, (2,4,5-trifluorophenyl)hydrazine phosphate, (2,4,6-trifluorophenyl)hydrazine phosphate, (2,3,4,5-tetrafluorophenyl)hydrazine phosphate, (2,3,4,6-tetrafluorophenyl)hydrazine phosphate, (2,3,5,6-tetrafluorophenyl)hydrazine phosphate, (2-chlorophenyl)hydrazine phosphate, (3-chlorophenyl)hydrazine phosphate, (2,3-dichlorophenyl)hydrazine phosphate, (2,4-dichlorophenyl)hydrazine phosphate, (2,5-dichlorophenyl)hydrazine phosphate, (2,6-dichlorophenyl)hydrazine phosphate, (2,3,4-trichlorophenyl)hydrazine phosphate, (2,3,5-trichlorophenyl)hydrazine phosphate, (2,3,6-trichlorophenyl)hydrazine phosphate, (2,4,5-trichlorophenyl)hydrazine phosphate, (2,4,6-trichlorophenyl)hydrazine phosphate, (2,3,4,5-tetrachlorophenyl)hydrazine phosphate, (2,3,4,6-tetrachlorophenyl)hydrazine phosphate, (2,3,5,6-tetrachlorophenyl)hydrazine phosphate, (2-bromophenyl)hydrazine phosphate, (3-bromophenyl)hydrazine phosphate, (4-bromophenyl)hydrazine phosphate, (2,3-dibromophenyl)hydrazine phosphate, (2,4-dibromophenyl)hydrazine phosphate, (2,5-dibromophenyl)hydrazine phosphate, (2,6-dibromophenyl)hydrazine phosphate, (2,3,4-tribromophenyl)hydrazine phosphate, (2,3,5-tribromophenyl)hydrazine phosphate, (2,3,6-tribromophenyl)hydrazine phosphate, (2,4,5-tribromophenyl)hydrazine phosphate, (2,4,6-tribromophenyl)hydrazine phosphate, (2,3,4,5-tetrabromophenyl)hydrazine phosphate, (2,3,4,6-tetrabromophenyl)hydrazine phosphate, (2,3,5,6-tetrabromophenyl)hydrazine phosphate, (2-methoxyphenyl)hydrazine phosphate, (3-methoxyphenyl)hydrazine phosphate, (4-methoxyphenyl)hydrazine phosphate, (2,3-dimethoxyphenyl)hydrazine phosphate, (2,4-dimethoxyphenyl)hydrazine phosphate, (2,5-dimethoxyphenyl)hydrazine phosphate, (2,6-dimethoxyphenyl)hydrazine phosphate, (3,4-dimethoxyphenyl)hydrazine phosphate, (3,5-dimethoxyphenyl)hydrazine phosphate, (2-ethylphenyl)hydrazine phosphate, (3-ethylphenyl)hydrazine phosphate, (4-ethylphenyl)hydrazine phosphate, (2,3-diethylphenyl)hydrazine phosphate, (2,4-diethylphenyl)hydrazine phosphate, (2,5-diethylphenyl)hydrazine phosphate, (2,6-diethylphenyl)hydrazine phosphate, (2-(trifluoromethyl)phenyl)hydrazine phosphate, (3-(trifluoromethyl)phenyl)hydrazine phosphate, (4-(trifluoromethyl)phenyl)hydrazine phosphate, (2,3-bis(trifluoromethyl)phenyl)hydrazine phosphate, (2,4-bis(trifluoromethyl)phenyl)hydrazine phosphate, (2,5-bis(trifluoromethyl)phenyl)hydrazine phosphate, (2,6-bis(trifluoromethyl)phenyl)hydrazine phosphate, (2,4,6-tris(trifluoromethyl)phenyl)hydrazine phosphate, 2-hydrazinylbenzonitrile phosphate, 3-hydrazinylbenzonitrile phosphate, 4-hydrazinylbenzonitrile phosphate, 3-hydrazinylphthalonitrile phosphate, 4-hydrazinylisophthalonitrile phosphate, 2-hydrazinylterephthalonitrile phosphate, 2-hydrazinylisophthalonitrile phosphate, (2-fluoro-3-methoxyphenyl)hydrazine phosphate, (2-fluoro-4-methoxyphenyl)hydrazine phosphate, (2-fluoro-5-methoxyphenyl)hydrazine phosphate, (2-fluoro-6-methoxyphenyl)hydrazine phosphate, (3-fluoro-2-methoxyphenyl)hydrazine phosphate, (3-fluoro-4-methoxyphenyl)hydrazine phosphate, (3-fluoro-5-methoxyphenyl)hydrazine phosphate, (5-fluoro-2-methoxyphenyl)hydrazine phosphate, (4-fluoro-2-methoxyphenyl)hydrazine phosphate, (4-fluoro-3-methoxyphenyl)hydrazine phosphate, (2-choloro-3-methoxyphenyl)hydrazine phosphate, (2-choloro-4-methoxyphenyl)hydrazine phosphate, (2-choloro-5-methoxyphenyl)hydrazine phosphate, (2-choloro-6-methoxyphenyl)hydrazine phosphate, (3-choloro-2-methoxyphenyl)hydrazine phosphate, (3-choloro-4-methoxyphenyl)hydrazine phosphate, (3-choloro-5-methoxyphenyl)hydrazine phosphate, (5-choloro-2-methoxyphenyl)hydrazine phosphate, (4-choloro-2-methoxyphenyl)hydrazine phosphate, (4-choloro-3-methoxyphenyl)hydrazine phosphate, (2-nitrophenyl)hydrazine phosphate, (3-nitrophenyl)hydrazine phosphate, (4-nitrophenyl)hydrazine phosphate, (2-methoxy-3-nitrophenyl)hydrazine phosphate, (2-methoxy-4-nitrophenyl)hydrazine phosphate, (2-methoxy-5-nitrophenyl)hydrazine phosphate, (2-methoxy-5-nitrophenyl)hydrazine phosphate, (3-methoxy-2-nitrophenyl)hydrazine phosphate, (4-methoxy-2-nitrophenyl)hydrazine phosphate, (5-methoxy-2-nitrophenyl)hydrazine phosphate, (3-methoxy-5-nitrophenyl)hydrazine phosphate, (3-methoxy-4-nitrophenyl)hydrazine phosphate, (4-methoxy-3-nitrophenyl)hydrazine phosphate, (4-bromo-2-fluorophenyl)hydrazine phosphate, 2-hydrazinylbenzoic acid phosphate, 3-hydrazinylbenzoic acid phosphate, (4-chloro-2-fluorophenyl)hydrazine phosphate, 3-fluoro-4-hydrazinylbenzonitrile phosphate, (4-ethoxyphenyl)hydrazine phosphate, (4-propoxyphenyl)hydrazine phosphate, (4-butoxyphenyl)hydrazine phosphate, (3-isopropylphenyl)hydrazine phosphate, (4-propylphenyl)hydrazine phosphate, (4-vinylphenyl)hydrazine phosphate, (4-allylphenyl)hydrazine phosphate, (4-(but-3-en-1-yl)phenyl)hydrazine phosphate.

4. The continuous flow process as described in claim 1, wherein the reaction process of the synthesis process does not contain diazoamino compounds, and the outlet products do not contain diazoamino compounds, reduction reaction intermediates and reduction reaction products and the structural formula of the diazoamino compounds is as follows:

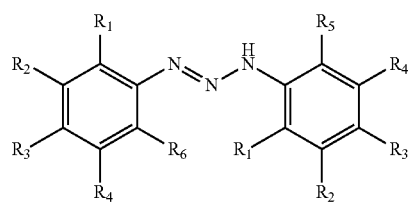

wherein the structural formula of the reduction reaction intermediates anions are as follows:

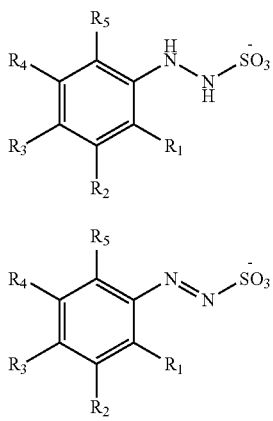

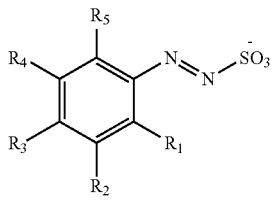

wherein the structural formula of anions of the reduction reaction products are as follows:

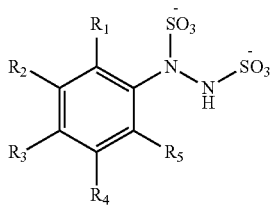

where, the cations are selected from any metal cation or NH4+;
R1 is —SO3H;
R2 is —COOH;
R3 is —CF3;
R4 is C1-C4 alkoxy;
R5 is C1-C4 alkoxy.

5. The continuous flow process as described in claim 1, wherein the total reaction time is 2~20 min.

6. The continuous flow process as described in claim 1, wherein the total reaction time is 7~11 min.

7. The continuous flow process as described in claim 1, wherein the molar ratio of aniline or substituted phenylamine to diazotization reagents is 1:0.9~1.2.

8. The continuous flow process as described in claim 1, wherein the molar ratio of aniline or substituted phenylamine to reductants is 1:2.0~8.0.

9. The continuous flow process as described in claim 1, wherein the molar ratio of aniline or substituted phenylamine to acids is 1:3.0~10.0.

10. The continuous flow process as described in claim 1, wherein the temperature of the diazotization reaction is 2~80° C.

11. The continuous flow process as described in claim 1, wherein the temperature of the reduction reaction 40~130° C.

12. The continuous flow process as described in claim 1, wherein the temperature of acidic hydrolysis and salifying is 40~130° C.

13. The continuous flow process as described in claim 1, wherein the integrated reactor adopts modular structure, and contains multiple temperature zones, each of which independently contains more than one reactor modules or reactor module groups, and the reactor module group is composed of multiple reactor modules in series or in parallel, and each temperature zone is connected to each other.

14. The continuous flow process as described in claim 13, wherein the reactor module is any reactor that can realize continuous flow process; the reactor is any one or any kinds of micro-reactor, series coil reactor, tubular reactor.

15. The continuous flow process as described in claim 13, wherein the reactor modules, the reactor module groups, each reactor module and reactor module groups are connected in series or parallel with each other.

16. The continuous flow process as described in claim 13, wherein the continuous flow synthesis process is carried out in an integrated reactor with four temperature zones, continuous flow synthesis process consists of the following steps:

(a) under acidic conditions, aniline or substituted phenylamine is transported into temperature zone mixing with liquid of diazotization reagent, where diazotization reaction is completed to generate diazoate salt; (b) the reductants aqueous solution is transported to the temperature zone II for pre-heating, and then mixes with the diazoate salt solution generated by the temperature zone I in the temperature zone III, and flows through the temperature zone III until the reaction is complete; (c) the reaction liquid flowing out of zone III mixes with acid enters zone IV, and flows through zone IV until the reaction is complete and phenylhydrazine salt or substituted phenylhydrazine salt is obtained.

17. The continuous flow process as described in claim 16, wherein the temperature of the zone I is 2~80° C.

18. The continuous flow process as described in claim 16, wherein the temperature of the zone II is 30~120° C.

19. The continuous flow process as described in claim 16, wherein the temperature of the zone III is 40~130° C.

20. The continuous flow process as described in claim 16, wherein the temperature of the zones IV is 40~130° C.

* * * * *